US012697387B2

(12) United States Patent
Feucht et al.

(10) Patent No.: US 12,697,387 B2
(45) Date of Patent: Aug. 4, 2026

(54) CHIMERIC ANTIGEN RECEPTORS TARGETING CD19 AND USE THEREOF

(71) Applicants: MEMORIAL SLOAN-KETTERING CANCER CENTER, New York, NY (US); SLOAN-KETTERING INSTITUTE FOR CANCER RESEARCH, New York, NY (US); MEMORIAL HOSPITAL FOR CANCER AND ALLIED DISEASES, New York, NY (US); MILLENNIUM PHARMACEUTICALS, INC., Cambridge, MA (US)

(72) Inventors: Judith Feucht, Tuebingen (DE); Jorge Mansilla-Soto, Forest Hills, NY (US); Isabelle Rivière, New York, NY (US); Michel Sadelain, New York, NY (US); Loic Vincent, Cambridge, MA (US); Gary Shapiro, Cambridge, MA (US); Mei Rosa Ng, Cambridge, MA (US); Dan Tavares, Cambridge, MA (US); Xingyue He, Cambridge, MA (US)

(73) Assignees: MEMORIAL SLOAN-KETTERING CANCER CENTER, New York, NY (US); SLOAN-KETTERING INSTITUTE FOR CANCER RESEARCH, New York, NY (US); MEMORIAL HOSPITAL FOR CANCER AND ALLIED DISEASES, New York, NY (US); MILLENNIUM PHARMACEUTICALS, INC., Cambridge, MA (US)

( * ) Notice: Subject to any disclaimer, the term of this patent is extended or adjusted under 35 U.S.C. 154(b) by 752 days.

(21) Appl. No.: 18/049,151

(22) Filed: Oct. 24, 2022

(65) Prior Publication Data

US 2023/0346938 A1 Nov. 2, 2023

Related U.S. Application Data

(63) Continuation of application No. PCT/US2021/029138, filed on Apr. 26, 2021.

(60) Provisional application No. 63/015,362, filed on Apr. 24, 2020, provisional application No. 63/073,133, filed on Sep. 1, 2020.

(51) Int. Cl.
| | |
|---|---|
| *A61K 40/00* | (2025.01) |
| *A61K 40/11* | (2025.01) |
| *A61K 40/15* | (2025.01) |
| *A61K 40/31* | (2025.01) |
| *A61K 40/32* | (2025.01) |
| *A61K 40/42* | (2025.01) |
| *A61P 35/00* | (2006.01) |
| *C07K 14/705* | (2006.01) |
| *C07K 16/28* | (2006.01) |

(52) U.S. Cl.
CPC .............. *A61K 40/31* (2025.01); *A61K 40/11* (2025.01); *A61K 40/15* (2025.01); *A61K 40/32* (2025.01); *A61K 40/4211* (2025.01); *A61P 35/00* (2018.01); *C07K 14/7051* (2013.01); *C07K 14/70521* (2013.01); *C07K 16/2803* (2013.01); *A61K 2239/48* (2023.05); *C07K 2317/622* (2013.01)

(58) Field of Classification Search
CPC ........ A61K 40/31; A61K 40/11; A61K 40/15; A61K 40/32; A61K 40/4211; A61K 2239/48; A61P 35/00; C07K 14/7051; C07K 14/70521; C07K 16/2803; C07K 2317/622
See application file for complete search history.

(56) References Cited

U.S. PATENT DOCUMENTS

| | | | |
|---|---|---|---|
| 5,399,346 A | | 3/1995 | Anderson et al. |
| 2002/0086014 A1 | | 7/2002 | Korman et al. |
| 2017/0044259 A1 | | 2/2017 | Tipton et al. |
| 2019/0330337 A1 | | 10/2019 | Pulé et al. |

FOREIGN PATENT DOCUMENTS

| | | | |
|---|---|---|---|
| WO | WO 2009 036379 A2 | 3/2009 |
| WO | WO 2010 105256 A1 | 9/2010 |
| WO | WO 2012 009568 A2 | 1/2012 |
| WO | WO 2014/087010 A1 | 6/2014 |
| WO | WO 2017/172981 A2 | 10/2017 |
| WO | WO2017/180989 A2 | 10/2017 |
| WO | WO 2019/232503 A1 | 12/2019 |
| WO | WO 2019/241315 A1 | 12/2019 |

OTHER PUBLICATIONS

Rabia et al (Biochem Eng J. Sep. 15, 2018; 137: 365-374) (Year: 2018).*
Chen et al (JEM 176:855-866, 1992 (Year: 1992).*
Altschul et al., "Gapped BLAST and PSI-BLAST: a new generation of protein database search programs," Nucleic Acids Res., 25(17):3389-3402 (1997).
Altschul, et al., "Basic Local Alignment Search Tool," J. Mol. Biol., 215:403-410 (1990).
Anderson, "Prospects for Human Gene Therapy," Science 226:401-409 (1984).
Blömer et al., "Highly Efficient and Sustained Gene Transfer in Adult Neurons with a Lentivirus Vector," Journal of Virology 71:6641-6649 (1997).
Bregni, et al., "Human Peripheral Blood Hematopoietic Progenitors Are Optimal Targets of Retroviral-Mediated Gene Transfer," Blood 80:1418-1422 (1992).

(Continued)

*Primary Examiner* — Lei Yao
(74) *Attorney, Agent, or Firm* — Baker Botts L.L.P.

(57) ABSTRACT

The presently disclosed subject matter provides chimeric antigen receptors (CARs) that specifically target CD19 and cells comprising such CD19-targeted CARs. The presently disclosed subject matter further provides uses of the CD19-targeted CARs for treatment, e.g., for treating blood cancer.

46 Claims, 28 Drawing Sheets

Specification includes a Sequence Listing.

(56)                    References Cited

OTHER PUBLICATIONS

Brigham et al., "Rapid Communication: In vivo Transfection of Murine Lungs with a Functioning Prokaryotic Gene Using a Liposome Vehicle," Am. J. Med. Sci. 298:278-281 (1989).

Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy 8:423-430 (1997).

Chothia et al., "Conformations of immunoglobulin hypervariable regions," Nature vol. 342, 877-883 (1989).

Cornetta et al., "Gene Transfer into Primates and Prospects for Gene Therapy in Humans," Progress in Nucleic Acid Research and Molecular Biology 36:311-322 (1987).

Danos et al., "Safe and efficient generation of recombinant retroviruses with amphotropic and ecotropic host ranges," PNAS USA 85:6460-6464 (1988).

Eglitis et al., "Retroviral Vectors for Introduction of Genes into Mammalian Cells," BioTechniques 6(7):608-614 (1988).

Estep et al., "High throughput solution-based measurement of antibody-antigen affinity and epitope binning," Mabs 5(2), 270-278 (2013).

Eyquem et al., "Targeting CAR to the TRAC locus with a CRISPR/Cas9 enhances tumour rejection," Nature 543, 113-117 (2017).

Felgner et al., "Lipofection: A highly efficient, lipid-mediated DNA-transfection Procedure," PNAS USA, 84:7413-7417 (1987).

Feucht et al., "Calibration of CAR activation potential directs alternative T cell fates and therapeutic potency," Nature Medicine, 25(1): 82-88 (2019).

Friedmann, "Progress toward Human Gene Therapy," Science 244(4910):1275-1281 (1989).

Gade et al., "Targeted elimination of prostate cancer by genetically directed human T lymphocytes," Cancer Res 65, 9080-9088 (2005).

Giavridis et al., "CAR T cell—induced cytokine release syndrome is mediated by macrophages and abated by IL-1 blockade," Nature Medicine 24 No. 6, 731-738; DOI: 10.1038/s41591-018-0041-7 (2018).

Hamieh et al., "CAR T cell trogocytosis and cooperative killing regulate tumour antigen escape," Nature, 568(7750): 112-116 (2019).

Hollyman et al., "Manufacturing Validation of Biologically Functional T Cells Targeted to CD19 Antigen for Autologous Adoptive Cell Therapy," J. Immunotherapy, 32(2):169-180 (2009).

Hughes et al., "Retroviral Gene Transfer to Primitive Normal and Leukemic Hematopoietic Cells Using Clinically Applicable Procedures," J. Clin. Invest. 89:1817-1824 (1992).

International Search Report and Written Opinion dated Oct. 13, 2021 corresponding to International Patent Application No. PCT/US2021/029138.

Johnson, "Gene Therapy for Cystic Fibrosis," Chest 107:77S-83S (1995).

Kido et al., "Use of a retroviral vector with an internal opsin promoter to direct gene expression to retinal photoreceptor cells," Current Eye Research 15:833-844 (1996).

Le Gal La Salle et al., "An Adenovirus Vector for Gene Transfer into Neurons and Glia in the Brain," Science 259(5097): 988-990 (1993).

MacCallum et al., "Antibody-antigen interactions: contact analysis and binding site topography," J. Mol. Biol., 262:732-745 (1996).

Makabe et al., "Thermodynamic consequences of mutations in vernier zone residues of a humanized anti-human epidermal growth factor receptor murine antibody, 528," Journal of Biological Chemistry, 283: 1156-1166 (2008).

Miller, "Retrovirus Packaging Cells," Human Gene Therapy 1:5-14 (1990).

Miller et al., "Improved Retroviral Vectors for Gene Transfer and Expression," Biotechniques 7(9):980-990 (1989).

Miller et al., "Redesign of Retrovirus Packaging Cell Lines to Avoid Recombination Leading to Helper Virus Production," Mol. Cell. Biol. 6(8):2895-2902 (1986).

Miller et al., "Generation of Helper-Free Amphotropic Retroviruses That Transduce a Dominant-Acting, Methotrexate-Resistant Dihydrofolate Reductase Gene," Mol. Cell. Biol. 5(3):431-437 (1985).

Miyoshi et al., "Stable and efficient gene transfer into the retina using an HIV-based lentiviral vector," PNAS USA 94:10319-10323 (1997).

Moen, "Directions in Gene Therapy," Blood Cells 17:407-416 (1991).

Myers et al., "Optimal alignments in linear space," Bioinformatics., 4(1), 11-17 (1988).

Naldini et al., "In Vivo Gene Delivery and Stable Transduction of Nondividing Cells by a Lentiviral Vector," Science 272(5259):263-267 (1996).

Needleman et al., "A General Method Applicable to the Search for Similarities in the Amino Acid Sequence of Two Proteins," J. Mol. Biol. 48:443-453 (1970).

Ono et al., "Plasmid DNAs directly injected into mouse brain with lipofectin can be incorporated and expressed by brain cells," Neuroscience Letters, 117:259-263 (1990).

Przybylowski et al., "Production scale-up and validation of packaging cell clearance of clinical-grade retroviral vector stocks produced in Cell Factories," Gene Therapy, 13(1):95-100 (2006).

Rosenberg et al., "Gene Transfer into Humans," N. Engl. J. Med 323(9):570-578 (1990).

Sharp, "Gene Therapy," The Lancet 337:1277-1278 (1991).

Shen et al., Anal. Chem. 80(6):1910-1917 (2008).

Siegel et al., High efficiency recovery and epitope-specific sorting of an scFv yeast display library, J Immunol Methods 286(1-2), 141-153 (2004).

Straubinger et al., "Liposomes as Carriers for Intracellular Delivery of Nucleic Acids," Methods in Enzymology, 101:512-527 (1983).

Tolstoshev et al., "Gene expression using retroviral vectors," Current Opinion in Biotechnology 1:55-61 (1990).

UniProtKB Accession No. A0A3D8QFM8_9EURO, Defect at low temperature protein 1. Jan. 16, 2019 [online]. [Retrieved on Sep. 17, 2021]. Retrieved from the internet: <URL: https://www.uniprot.org/uniprot/A0A3D8QFM8> entire sequence.

Wolff et al., "Direct Gene Transfer into Mouse Muscle in Vivo," Science 247(4949):1465-1468 (1990).

Wu et al., "Targeting Genes: Delivery and Persistent Expression of a Foreign Gene Driven by Mammalian Regulatory Elements in Vivo," Journal of Biological Chemistry 264(29):16985-16987 (1989).

Wu et al., "Receptor-mediated Gene Delivery and Expression in Vivo," Journal of Biological Chemistry, 263(29):14621-14624 (1988).

Xu et al., "Correction of the enzyme deficiency in hematopoietic cells of Gaucher patients using a clinically acceptable retroviral supernatant transduction protocol," Exp. Hemat. 22:223-230 (1994).

Zhao et al., "Structural Design of Engineered Costimulation Determines Tumor Rejection Kinetics and Persistence of CAR T Cells," Cancer Cell 28, 415-428 (2015).

Brudno et al., "Safety and feasibility of anti-CD19 CAR T cells with fully human binding domains in patients with B-cell lymphoma," Nature Medicine, 26(2):270-280 (2020).

Extended European Search Report dated Apr. 24, 2024 in Application No. EP 21793613.

* cited by examiner

Protein Sequence:

CD19ss: Highlighted in red
His: Highlighted in blue
HSA: Highlighted in purple
Tev Site: Highlighted in green >CD19_ECD_C10HisTev-GS_HSA_mat

SEQ ID NO: 77

```
MPPPRRLLFFLFLTPMEVRPEEPLVVKVEEGDNAVLQCLKGTSDGPTQQLTWSRESPLKPFLKLSLGLPGLGIHMRPLAIWLFIFNVSQQMGGFYLC
QPGPPSEKAWQPGWTVNVEGSGELFRWNVSDLGGLGCGLKNRSSEGPSSPSGKLMSPKLYWAKDRPEIWEGEPPCLPPRDSLNQSLSQDLT
MAPGSTLWLSCGVPPDSVSRGPLSWTHVHPKGPKSLLSLELKDDRPARDMWVMETGLLLPRATAQDAGKYYCHRGNLTMSFHLEITARPVLWH
WLLRTGGWKHHHHHHHHDYDIPTTENLYFQGGGGSGGGGSGGGGSGGGGSDAHKSEVAHRFKDLGEENFKALVLIAFAQYLQQCPFEDH
VKLVNEVTEFAKTCVADESAENCDKSLHTLFGDKLCTVATLRETYGEMADCCAKQEPERNECFLQHKDDNPNLPRLVRPEVDVMCTAFHDNEETF
LKKYLYEIARRHPYFYAPELLFFAKRYKAAFTECCQAADKAACLLPKLDELRDEGKASSAKQRLKCASLQKFGERAFKAWAVARLSQRFPKAEFAE
VSKLVTDLTKVHTECCHGDLLECADDRADLAKYICENQDSISSKLKECCEKPLLEKSHCIAEVENDEMPADLPSLAADFVESKDVCKNYAEAKDVFL
GMFLYEYARRHPDYSVVLLLRLAKTYETTLEKCCAAADPHECYAKVFDEFKPLVEEPQNLIKQNCELFEQLGEYKFQNALLVRYTKKVPQVSTPTLV
EVSRNLGKVGSKCCKHPEAKRMPCAEDYLSWVLNQLCVLHEKTPVSDRVTKCCTESLVNRRPCFSALEVDETYVPKEFNAETTFHADICTLSEKE
RQIKKQTALVELVKHKPKATKEQLKAVMDDFAAFVEKCCKADDKETCFAEEGKKLVAASQAALGL
```

FIG. 6

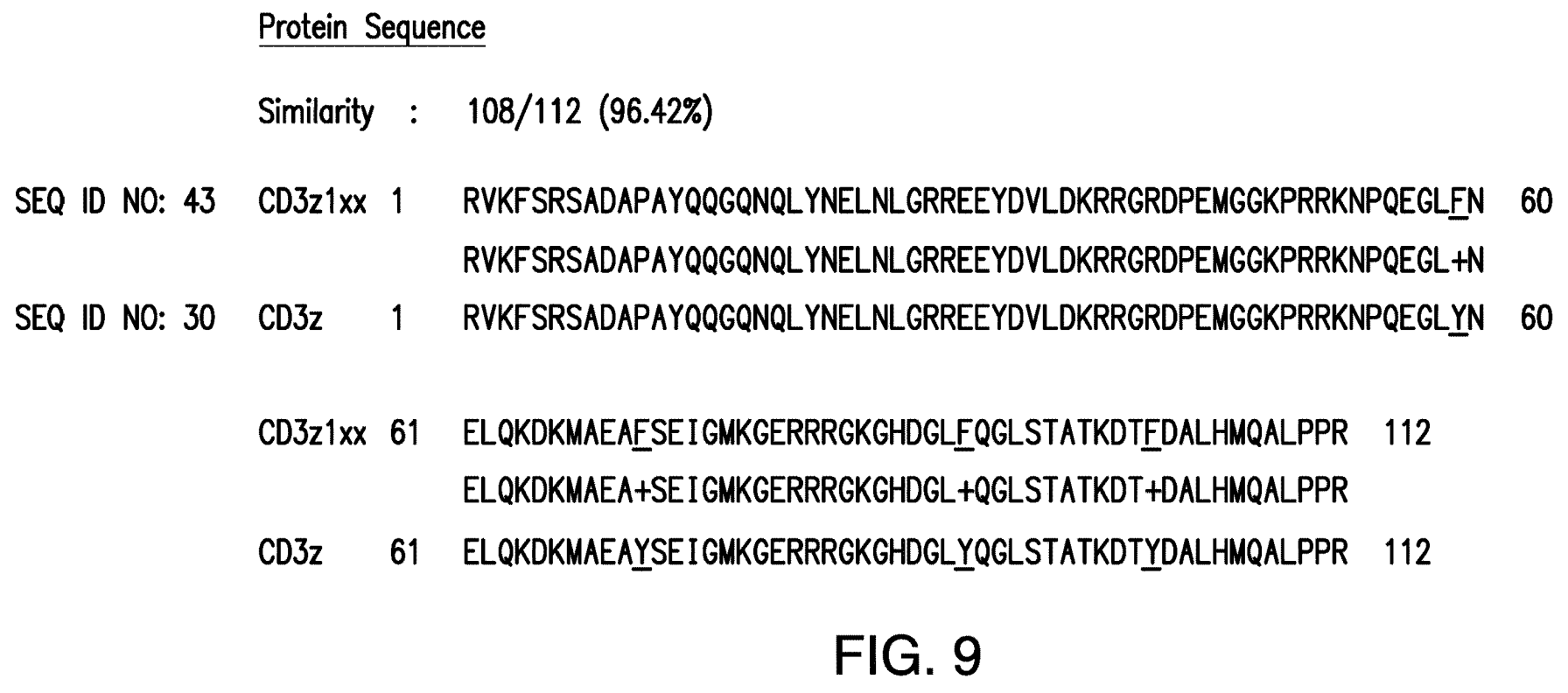

Protein Sequence

Similarity : 108/112 (96.42%)

| | | | |
|---|---|---|---|
| SEQ ID NO: 43 | CD3z1xx | 1 | RVKFSRSADAPAYQQGGQNQLYNELNLGRREEYDVLDKRRGRDPEMGGKPRRKNPQEGLFN   60 |
| | | | RVKFSRSADAPAYQQGGQNQLYNELNLGRREEYDVLDKRRGRDPEMGGKPRRKNPQEGL+N |
| SEQ ID NO: 30 | CD3z | 1 | RVKFSRSADAPAYQQGGQNQLYNELNLGRREEYDVLDKRRGRDPEMGGKPRRKNPQEGLYN   60 |
| | CD3z1xx | 61 | ELQKDKMAEAFSEIGMKGERRRGKGHDGLFQGLSTATKDTFDALHMQALPPR   112 |
| | | | ELQKDKMAEA+SEIGMKGERRRGKGHDGL+QGLSTATKDT+DALHMQALPPR |
| | CD3z | 61 | ELQKDKMAEAYSEIGMKGERRRGKGHDGLYQGLSTATKDTYDALHMQALPPR   112 |

FIG. 9

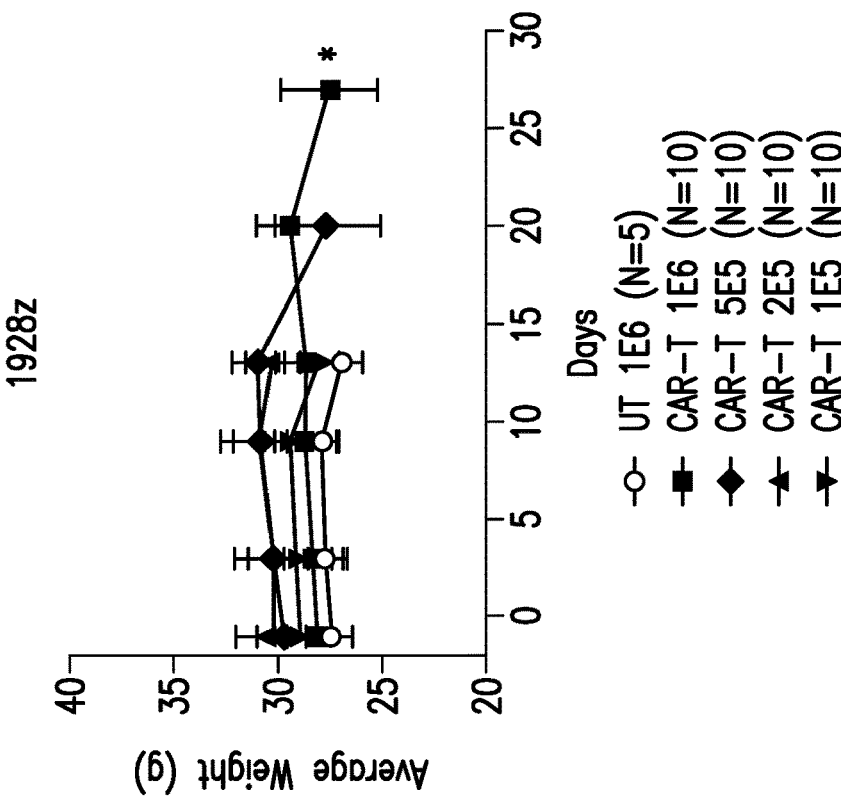
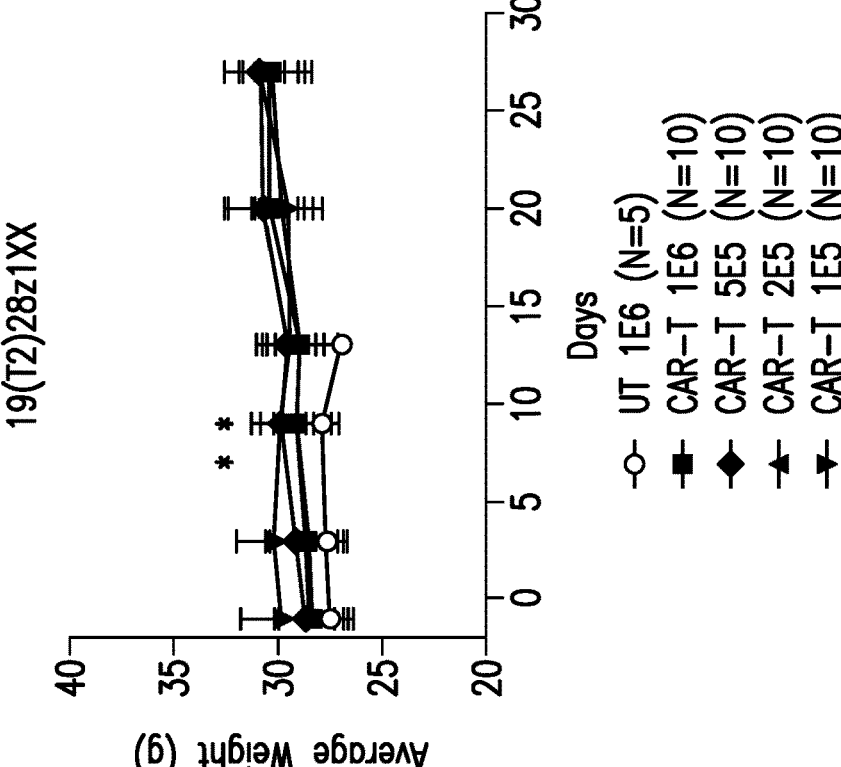
FIG. 18

CHIMERIC ANTIGEN RECEPTORS TARGETING CD19 AND USE THEREOF

1. CROSS-REFERENCE TO RELATED APPLICATIONS

This application is a continuation application of International Patent Application No. PCT/US21/29138, filed on Apr. 26, 2021, which claims priority to U.S. Provisional Patent Application Ser. No. 63/015,362, filed Apr. 24, 2020, and U.S. Provisional Patent Application Ser. No. 63/073, 133, filed Sep. 1, 2020, the contents of each of which are incorporated by reference in their entirety, and to each of which priority is claimed.

SEQUENCE LISTING

The instant application contains a Sequence Listing which has been submitted electronically in XML format and is hereby incorporated by reference in its entirety. Said XML, copy, created on Oct. 24, 2022, is named 087108.0114.xml and is 108,575 bytes in size.

2. TECHNICAL FIELD

The presently disclosed subject matter provides methods for treating neoplasm (e.g., cancer) using cells comprising a chimeric antigen receptor (CAR) that specifically targets CD19.

3. BACKGROUND

Cell-based immunotherapy is a therapy with curative potential for the treatment of cancer. T-cells and other immune cells may be modified to target tumor antigens through the introduction of genetic material coding for artificial or synthetic receptors for antigen, termed Chimeric Antigen Receptors (CARs), specific to selected antigens. Targeted T-cell therapy using CARs has shown recent clinical success in treating hematologic malignancies.

T-cells expressing CD19-specific CARs with binding domains from murine monoclonal antibodies have been shown to treat B-cell malignancies. T-cell mediated immune responses specific for murine scFv antigen-binding domain of the CAR can develop in human patients and result in premature elimination of CAR T-cells increasing the risk of tumor relapse. Thus, there are needs for improved CD19-targeted CARs with reduced toxicity and immunogenicity and/or improved safety and efficacy.

4. SUMMARY OF THE INVENTION

The presently disclosed subject matter provides CD19-targeted chimeric antigen receptors (CARs), cells comprising the CD19-targeted CARs, and uses of the cells for treatments, e.g., for treating a neoplasm.

In certain embodiments, the CAR comprises an extracellular antigen-binding domain that specifically binds to CD19, a transmembrane domain, and an intracellular signaling domain. In certain embodiments, the extracellular antigen-binding domain comprises a single-chain variable fragment (scFv), a Fab, or a F(ab)$_2$. In certain embodiments, the extracellular antigen-binding domain comprises a scFv. In certain embodiments, the scFv is a human scFv. In certain embodiments, the extracellular antigen-binding domain comprises (a) a heavy chain variable region comprising a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and/or (b) a light chain variable region comprising:

i) a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 13 or a conservative modification thereof;

ii) a CDR1 comprising the amino acid sequence set forth in SEQ ID NO: 16 or a conservative modification thereof, a CDR2 comprising the amino acid sequence set forth in SEQ ID NO: 12 or a conservative modification thereof, and a CDR3 comprising the amino acid sequence set forth in SEQ ID NO: 17 or a conservative modification thereof;

iii) a CDR1 comprising the amino acid sequence set forth in SEQ ID NO: 11 or a conservative modification thereof, a CDR2 comprising the amino acid sequence set forth in SEQ ID NO: 20 or a conservative modification thereof, and a CDR3 comprising the amino acid sequence set forth in SEQ ID NO: 21 or a conservative modification thereof;

iv) a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 57 or a conservative modification thereof;

v) a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 59 or a conservative modification thereof;

vi) a CDR1 comprising the amino acid sequence set forth in SEQ ID NO: 16 or a conservative modification thereof, a CDR2 comprising the amino acid sequence set forth in SEQ ID NO: 12 or a conservative modification thereof, and a CDR3 comprising the amino acid sequence set forth in SEQ ID NO: 61 or a conservative modification thereof;

vii) a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 63 or a conservative modification thereof; or viii) a CDR1 comprising the amino acid sequence set forth in SEQ ID NO: 11 or a conservative modification thereof, a CDR2 comprising the amino acid sequence set forth in SEQ ID NO: 65 or a conservative modification thereof, and a CDR3 comprising the amino acid sequence set forth in SEQ ID NO: 66 or a conservative modification thereof.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9.

In certain embodiments, the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 13.

In certain embodiments, the light chain variable region comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 17.

In certain embodiments, the light chain variable region comprises a CDR1 comprising the amino acid sequence set forth in SEQ ID NO: 11, a CDR2 comprising the amino acid sequence set forth in SEQ ID NO: 20, and a CDR3 comprising the amino acid sequence set forth in SEQ ID NO: 21.

In certain embodiments, the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 57.

In certain embodiments, the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 59.

In certain embodiments, the light chain variable region comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 61.

In certain embodiments, the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 63.

In certain embodiments, the light chain variable region comprises a CDR1 comprising the amino acid sequence set forth in SEQ ID NO: 11, a CDR2 comprising the amino acid sequence set forth in SEQ ID NO: 65, and a CDR3 comprising the amino acid sequence set forth in SEQ ID NO: 66.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 13.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 17.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 11, a CDR2 comprising the amino acid sequence set forth in SEQ ID NO: 20, and a CDR3 comprising the amino acid sequence set forth in SEQ ID NO: 21.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 57.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 59.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 61.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 63.

In certain embodiments, the heavy chain variable region comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the light chain variable region comprises a CDR1 comprising the amino acid sequence set forth in SEQ ID NO: 11, a CDR2 comprising the amino acid sequence set forth in SEQ ID NO: 65, and a CDR3 comprising the amino acid sequence set forth in SEQ ID NO: 66.

In certain embodiments, the heavy chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% identical or homologous to the amino acid sequence set forth in SEQ ID NO: 10. In certain embodiments, the heavy chain variable region comprises the amino acid sequence set forth in SEQ ID NO: 10.

In certain embodiments, the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 14, SEQ ID NO: 18, SEQ ID NO: 22, SEQ ID NO: 58, SEQ ID NO: 60, SEQ ID NO: 62, SEQ ID NO: 64, or SEQ ID NO: 67. In certain embodiments, the light chain variable region comprises the amino acid sequence set forth in SEQ ID NO: 14, SEQ ID NO: 18, SEQ ID NO: 22 SEQ ID NO: 58, SEQ ID NO: 60, SEQ ID NO: 62, SEQ ID NO: 64, or SEQ ID NO: 67. In certain embodiments, the light chain variable region comprises the amino acid sequence set forth in SEQ ID NO: 14, SEQ ID NO: 18, or SEQ ID NO: 22.

In certain embodiments, the heavy chain variable region comprising an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 10; and the light chain variable region comprises an amino acid sequence that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98% or about 99% identical or homologous to the amino acid sequence set forth in SEQ ID NO: 14, SEQ ID NO: 18, SEQ ID NO: 22, SEQ ID NO: 58, SEQ ID NO: 60, SEQ ID NO: 62, SEQ ID NO: 64, or SEQ ID NO: 67. In certain embodiments, the heavy chain variable region comprises the amino acid sequence set forth in SEQ ID NO: 10; and the light chain variable region comprises the amino acid sequence set forth in SEQ ID NO: 14, SEQ ID NO: 18, SEQ ID NO: 22, SEQ ID NO: 58, SEQ ID NO: 60, SEQ ID NO: 62, SEQ ID NO: 64, or SEQ ID NO: 67. In certain embodiments, the heavy chain variable region comprises the amino acid sequence set forth in SEQ ID NO: 10; and the light chain variable region comprises the amino acid sequence set forth in SEQ ID NO: 14, SEQ ID NO: 18, or SEQ ID NO: 22.

In certain embodiments, the heavy chain variable region comprises the amino acid sequence set forth in SEQ ID NO: 10, and the light chain variable region comprises the amino acid sequence set forth in SEQ ID NO: 14.

In certain embodiments, the heavy chain variable region comprises the amino acid sequence set forth in SEQ ID NO: 10, and the light chain variable region comprises the amino acid sequence set forth in SEQ ID NO: 18.

In certain embodiments, the heavy chain variable region comprises the amino acid sequence set forth in SEQ ID NO: 10, and the light chain variable region comprises the amino acid sequence set forth in SEQ ID NO: 22.

In certain embodiments, the heavy chain variable region comprises the amino acid sequence set forth in SEQ ID NO: 10, and the light chain variable region comprises the amino acid sequence set forth in SEQ ID NO: 58.

In certain embodiments, the heavy chain variable region comprises the amino acid sequence set forth in SEQ ID NO: 10, and the light chain variable region comprises the amino acid sequence set forth in SEQ ID NO: 60.

In certain embodiments, the heavy chain variable region comprises the amino acid sequence set forth in SEQ ID NO: 10, and the light chain variable region comprises the amino acid sequence set forth in SEQ ID NO: 62.

In certain embodiments, the heavy chain variable region comprises the amino acid sequence set forth in SEQ ID NO: 10, and the light chain variable region comprises the amino acid sequence set forth in SEQ ID NO: 64.

In certain embodiments, the heavy chain variable region comprises the amino acid sequence set forth in SEQ ID NO: 10, and the light chain variable region comprises the amino acid sequence set forth in SEQ ID NO: 67.

In certain embodiments, the extracellular antigen-binding domain comprises a linker between the heavy chain variable region and the light chain variable region. In certain embodiments, the linker consists of the amino acid sequence set forth in SEQ ID NO: 1, SEQ ID NO: 2, SEQ ID NO: 3, or SEQ ID NO: 4. In certain embodiments, the heavy chain variable region and the light chain variable region are positioned from the N- to the C-terminus: $V_L$-$V_H$.

In certain embodiments, the extracellular antigen-binding domain comprises or is a scFv, which comprises or consists of the amino acid sequence set forth in SEQ ID NO: 15, SEQ ID NO: 19, or SEQ ID NO: 23.

In certain embodiments, the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, or a BTLA polypeptide. In certain embodiments, the transmembrane domain comprises a CD28 polypeptide.

In certain embodiments, the intracellular signaling domain comprises a CD3 polypeptide. In certain embodiments, the CD3ζ polypeptide is a modified CD3ζ polypeptide. In certain embodiments, the modified CD3ζ polypeptide comprises a native ITAM1, an ITAM2 variant consisting of two loss-of-function mutations, and an ITAM3 consisting of two loss-of-function mutations. In certain embodiments, the native ITAM1 consists of the amino acid sequence set forth in SEQ ID NO: 31. In certain embodiments, the ITAM2 variant consists of the amino acid sequence set forth in SEQ ID NO: 37. In certain embodiments, the ITAM3 variant consists of the amino acid sequence set forth in SEQ ID NO: 41. In certain embodiments, the modified CD3ζ polypeptide comprising or consists of the amino acid sequence set forth in SEQ ID NO: 43.

In certain embodiments, the intracellular signaling domain further comprises at least one co-stimulatory signaling region. In certain embodiments, the at least one co-stimulatory signaling region comprises a CD28 polypeptide, a 4-1BB poly4peptide, an OX40 polypeptide, an ICOS polypeptide, a DAP-10 polypeptide, or a combination thereof. In certain embodiments, the at least one co-stimulatory signaling region comprises an intracellular domain of CD28 or a portion thereof, an intracellular domain of 4-1BB or a portion thereof, an intracellular domain of OX40 or a portion thereof, an intracellular domain of ICOS or a portion thereof, or an intracellular domain of DAP-10 or a portion thereof. In certain embodiments, the at least one co-stimulatory signaling region comprises a CD28 polypeptide.

In certain embodiments, the CAR is expressed from a vector. In certain embodiments, the vector is a retroviral vector.

The presently disclosed subject matter further provides cells comprising the CARs disclosed herein. In certain embodiments, the cell is transduced with the CAR. In certain embodiments, the CAR is constitutively expressed on the surface of the cell. In certain embodiments, the cell is an immunoresponsive cell. In certain embodiments, the cell is a cell of the lymphoid lineage or a cell of the myeloid lineage. In certain embodiments, the cell is selected from the group consisting of a T cell, a Natural Killer (NK) cell, a stem cell from which lymphoid cells may be differentiated, and a stem cell from which myeloid cells may be differentiated. In certain embodiments, the cell is a T cell. In certain embodiments, the T cell is selected from the group consisting of helper T cells, cytotoxic T cells, memory T cells, regulatory T cells, tumor-infiltrating lymphocyte (TIL), Natural Killer T cells, mucosal associated invariant T cells, and γδ T cells. In certain embodiments, the cell is a NK cell. In certain embodiments, the NK cell is derived from a stem cell. In certain embodiments, the stem cell is a pluripotent stem cell. In certain embodiments, the pluripotent stem cell is an embryoid stem cell or an induced pluripotent stem cell.

Furthermore, the presently disclosed subject matter provides nucleic acid molecules encoding the CAR disclosed herein. In certain embodiments, the nucleic acid molecule further comprises a promoter that is operably linked to the CAR. The promoter can be endogenous or exogenous. In certain embodiments, the promoter is an exogenous promoter. In certain embodiments, the exogenous promoter is selected from the group consisting of an elongation factor (EF)-1 promoter, a cytomegalovirus immediate-early promoter (CMV) promoter, a simian virus 40 early promoter (SV40) promoter, a phosphoglycerate kinase (PGK) promoter, a metallothionein promoter, and Ubiquitin C promoter. In certain embodiments, the promoter is an endogenous promoter. In certain embodiments, the endogenous promoter is selected from a TCR alpha promoter, a TCR beta promoter, and a beta 2-microglobulin promoter. In certain embodiments, the promoter is an inducible promoter. In certain embodiments, the inducible promoter is selected from the group consisting of a NFAT transcriptional response element (TRE) promoter, a CD69 promoter, a CD25 promoter, an IL-2 promoter, a 4-1BB promoter, a PD1 promoter, and a LAG3 promoter.

The presently disclosed subject matter also provides vectors comprising the nucleic acid molecule disclosed herein. In certain embodiments, the vector is a retroviral vector.

The presently disclosed subject matter further provides cells expressing the nucleic acid molecule disclosed herein. In certain embodiments, the cell is a T cell or Natural Killer (NK) cell.

The presently disclosed subject matter provides compositions comprising the cell disclosed herein. In certain embodiments, the composition is a pharmaceutical composition further comprising a pharmaceutically acceptable carrier. In certain embodiments, the composition comprises between about $1\times10^6$ and about $5\times10^8$ cells. In certain embodiments, the composition comprises between about $1\times10^6$ and about $1\times10^8$ cells. In certain embodiments, the composition comprises between about $1\times10^6$ and about $5\times10^7$ cells. In certain embodiments, the composition comprises about $2.5\times10^7$ cells.

The presently disclosed subject matter further provides various methods of using the presently disclosed cells. The presently disclosed subject matter provides methods of reducing tumor burden in a subject. In certain embodiments, the method comprises administering to the subject the cell or the composition disclosed herein. In certain embodiments, the method reduces the number of tumor cells, reduces tumor size, and/or eradicates the tumor in the subject.

The presently disclosed subject matter provides methods of increasing or lengthening survival of a subject having a neoplasm. In certain embodiments, the method comprises administering to the subject the cell or the composition disclosed herein.

The presently disclosed subject matter provides methods of treating and/or preventing a neoplasm in a subject. In certain embodiments, the method comprises administering to the subject the cell or the composition disclosed herein.

The presently disclosed cells and compositions can be used in a therapy. In certain embodiments, the presently disclosed cells and compositions are used in treating and/or preventing a neoplasm in a subject. In certain embodiments, the presently disclosed cells and compositions are used in increasing or lengthening survival of a subject having a neoplasm. In certain embodiments, the presently disclosed cells and compositions are used in treating and/or preventing a neoplasm in a subject.

In certain embodiments, the tumor and/or neoplasm is associated with CD19. In certain embodiments, the tumor and/or neoplasm is a blood cancer. In certain embodiments, the blood cancer is selected from the group consisting of multiple myeloma, leukemia, and lymphomas. In certain embodiments, the leukemia is selected from the group consisting of include acute myeloid leukemia (AML), chronic myeloid leukemia (CML), acute lymphocytic leukemia (ALL), chronic lymphocytic leukemia (CLL), acute promyelocytic leukemia (APL), mixed-phenotype acute leukemia (MLL), hairy cell leukemia, and B cell prolymphocytic leukemia. In certain embodiments, the lymphoma is Hodgkin's lymphoma or non-Hodgkin's lymphoma. In certain embodiments, the tumor and/or neoplasm is a B cell malignancy. In certain embodiments, the B cell malignancy is selected from the group consisting of B cell non-Hodgkin lymphomas (NHL), B cell Hodgkin's lymphomas, B cell acute lymphocytic leukemia (ALL), B cell chronic lymphocytic leukemia (CLL), multiple myeloma (MM), CLL with Richter's transformation, and CNS lymphoma. In certain embodiments, the tumor and/or neoplasm is B cell lymphoma. In certain embodiments, the B cell lymphoma is relapsed or refractory (R/R) B cell lymphoma. In certain embodiments, the subject is a human subject.

Furthermore, the presently disclosed subject matter provides methods for producing a cell comprising the CAR disclosed herein. In certain embodiments, the method comprises introducing into the cell a nucleic acid molecule that encodes the CAR disclosed herein.

Furthermore, the presently disclosed subject matter provides kits for reducing tumor burden in a subject, treating and/or preventing a neoplasm in a subject, and/or increasing or lengthening survival of a subject having a neoplasm. In certain embodiments, the kit comprises the cell disclosed herein. In certain embodiments, the kit further comprises written instructions for using the cell for reducing tumor burden in a subject, treating and/or preventing a neoplasm in a subject, and/or increasing or lengthening survival of a subject having a neoplasm.

5. BRIEF DESCRIPTION OF THE DRAWINGS

FIGS. 1A and 1B depict cytotoxicity of T cells comprising CD19-targeted CARs against CD19-expressing cells. FIG. 1A shows the killing against CD19-expressing Raji cancer cell lines. FIG. 1B shows the killing against CD19 knock-out Raji cells. Positive control is 1928z-1XX CAR.

FIGS. 2A and 2B depict cytotoxicity of T cells comprising CD19-targeted CARs against CD19-expressing cells measured by flow based killing assessment. FIG. 2A shows the killing against CD19-expressing Raji cancer cell lines. FIG. 2B shows the killing against CD19 knock-out Raji cells. Positive control is 1928z-1XX CAR.

FIGS. 3A and 3B depict IL-2 cytokine secretion by T cells comprising CD19-targeted CARs. FIG. 3A shows IL-2 cytokine secretion by T cells comprising CD19-targeted CARs co-cultured with CD19-expressing Raji cancer cell lines. FIG. 3B shows IL-2 cytokine secretion by T cells comprising CD19-targeted CARs co-cultured with CD19 knock-out Raji cells. Positive control is 1928z-1XX CAR.

FIGS. 4A and 4B depict IFN-γ cytokine secretion by T cells comprising CD19-targeted CARs. FIG. 4A shows IFN-γ cytokine secretion by T cells comprising CD19-targeted CARs co-cultured with CD19-expressing Raji cancer cell lines. FIG. 4B shows IFN-γ cytokine secretion by T cells comprising CD19-targeted CARs co-cultured with CD19 knock-out Raji cells. Positive control is 1928z-1XX CAR.

FIG. 6 shows the amino acid sequence of the CD19-HSA-His10.

Figure 7:
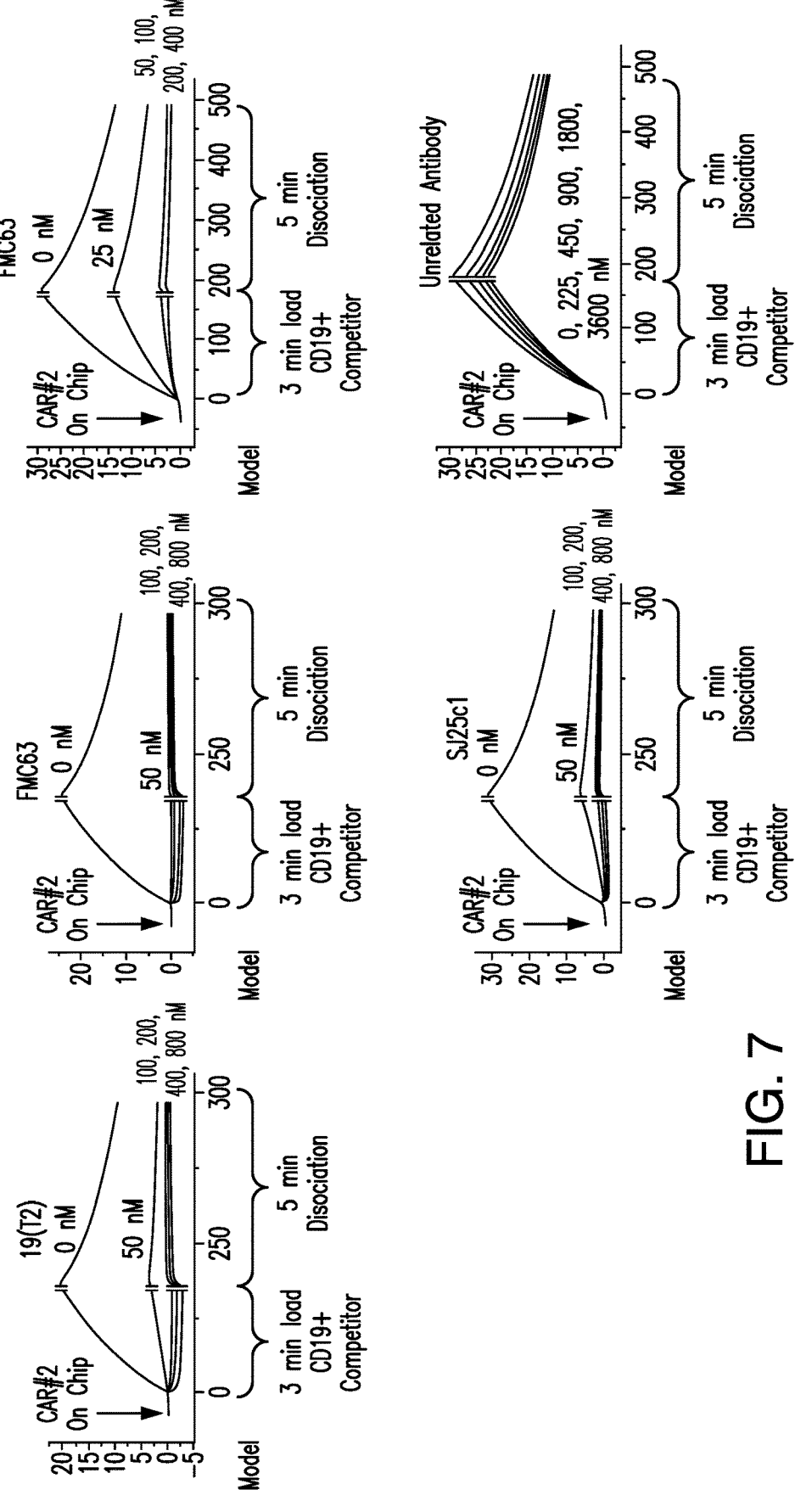

FIG. 7 shows binding data of #2 scFv, SJ25c1 scFv, and FMC63 scFv. The relative competition for a common epitope in the soluble CD19 antigen was evaluated in a Biacore surface plasmon resonance (SPR) assay. A mixture of soluble CD19-specific antibodies (FMC63 or SJ25c1) and CD19 antigen was flowed onto a chip containing #2 scFv to determine whether #2 scFv cross competes with the same epitope as SJ25c1 scFv, and FMC63 scFv. 19(T2) represents "#2 scFv".

Figure 8:
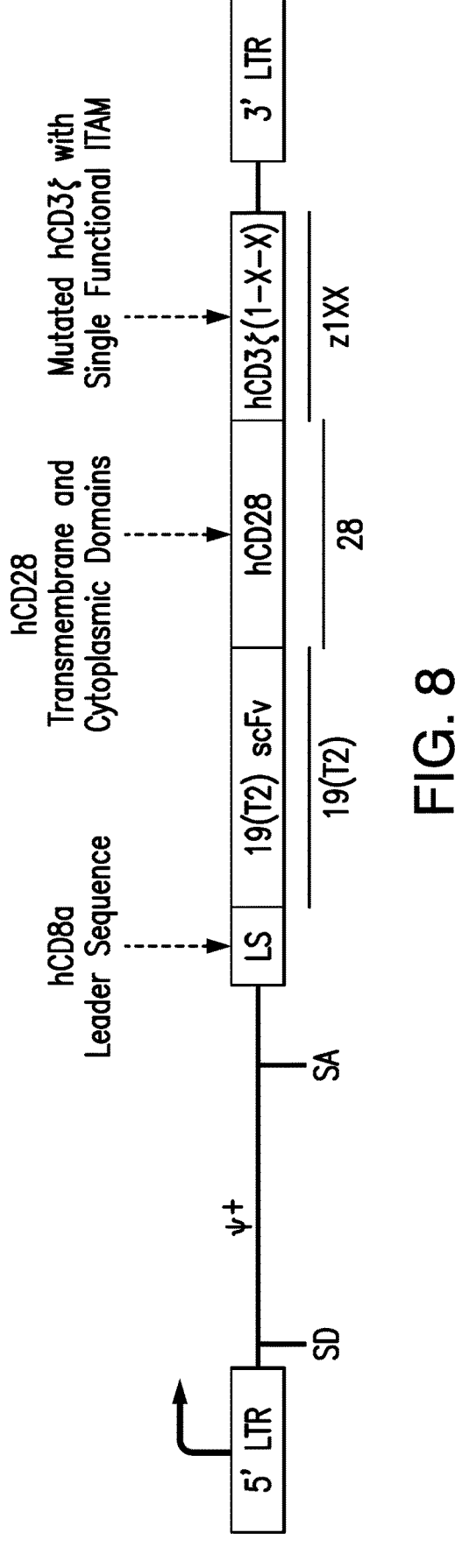

FIG. 8 depicts the gamma-retroviral vector comprising the #2 CAR. "19(T2)" represents "#2". The #2 CAR comprises the CD19-specific T2 (19(T2)) scFv (or "#2 scFv"), a CD8 alpha leader peptide, a CD28 gene fragment, and a modified CD3ζ intracellular signaling domain. The CD28 gene fragment includes its extracellular hinge, transmembrane, and intracellular domains. The modified CD3ζ chain has one functional wild-type and two mutated immunoreceptor tyrosine-based activation motifs (ITAMs), termed "1XX". The amino acid sequence of the modified CD3ζ intracellular signaling domain is set forth in SEQ ID NO: 43. The alignment of the amino acid sequence of the CD3-1XX to the CD3ζ-wild type is presented in FIG. 9. The amino acid differences between the two sequences are marked.

FIG. 9 depicts the alignment of the amino acid sequence of the CD30XX to the CD3ζ-wild type.

Figure 10:
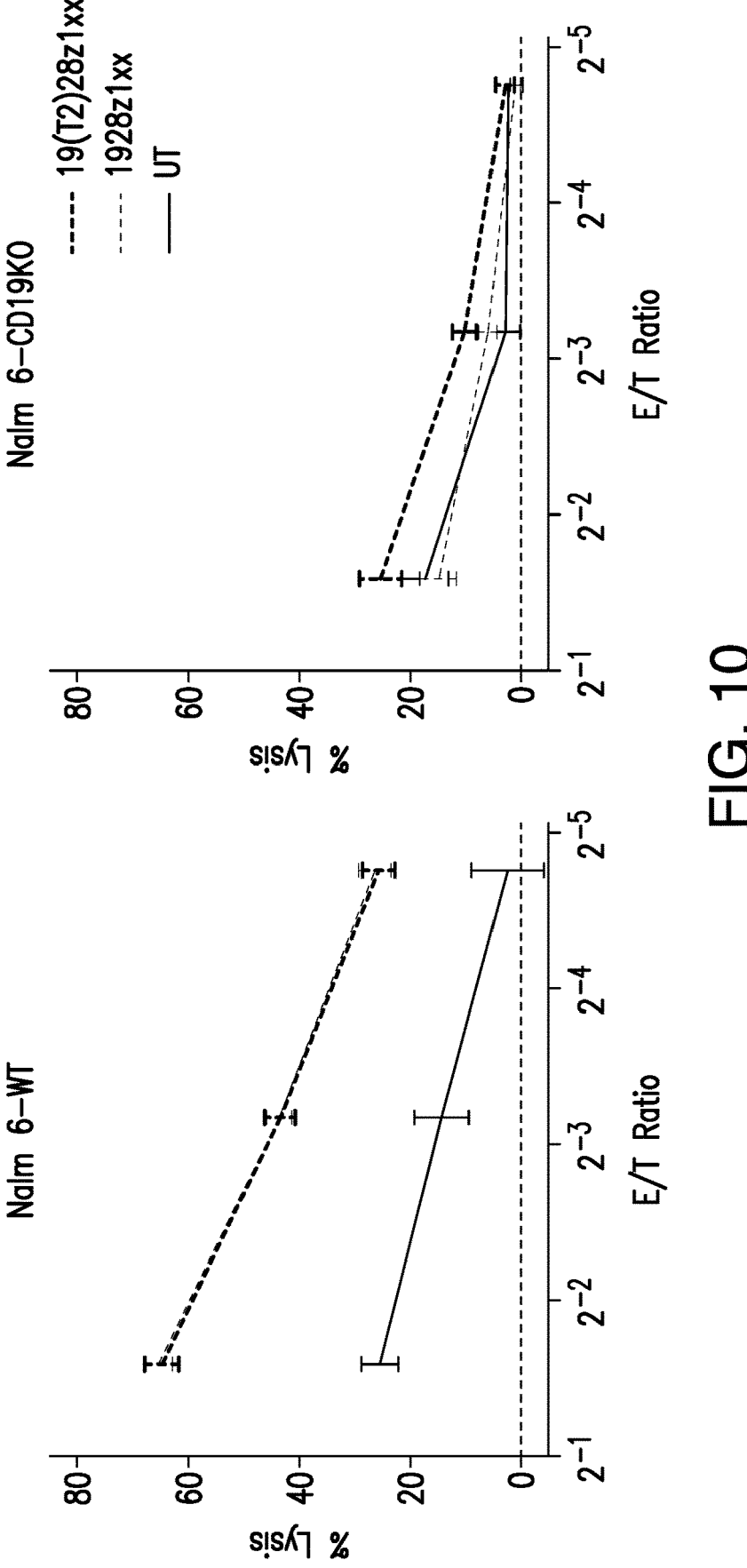

FIG. 10 depicts in vitro cytotoxic activity of #2 CAR-T cells and 1928z-1XX CAR T cells. "19(T2)28z1xx" represents "#2 CAR".

Figure 11:
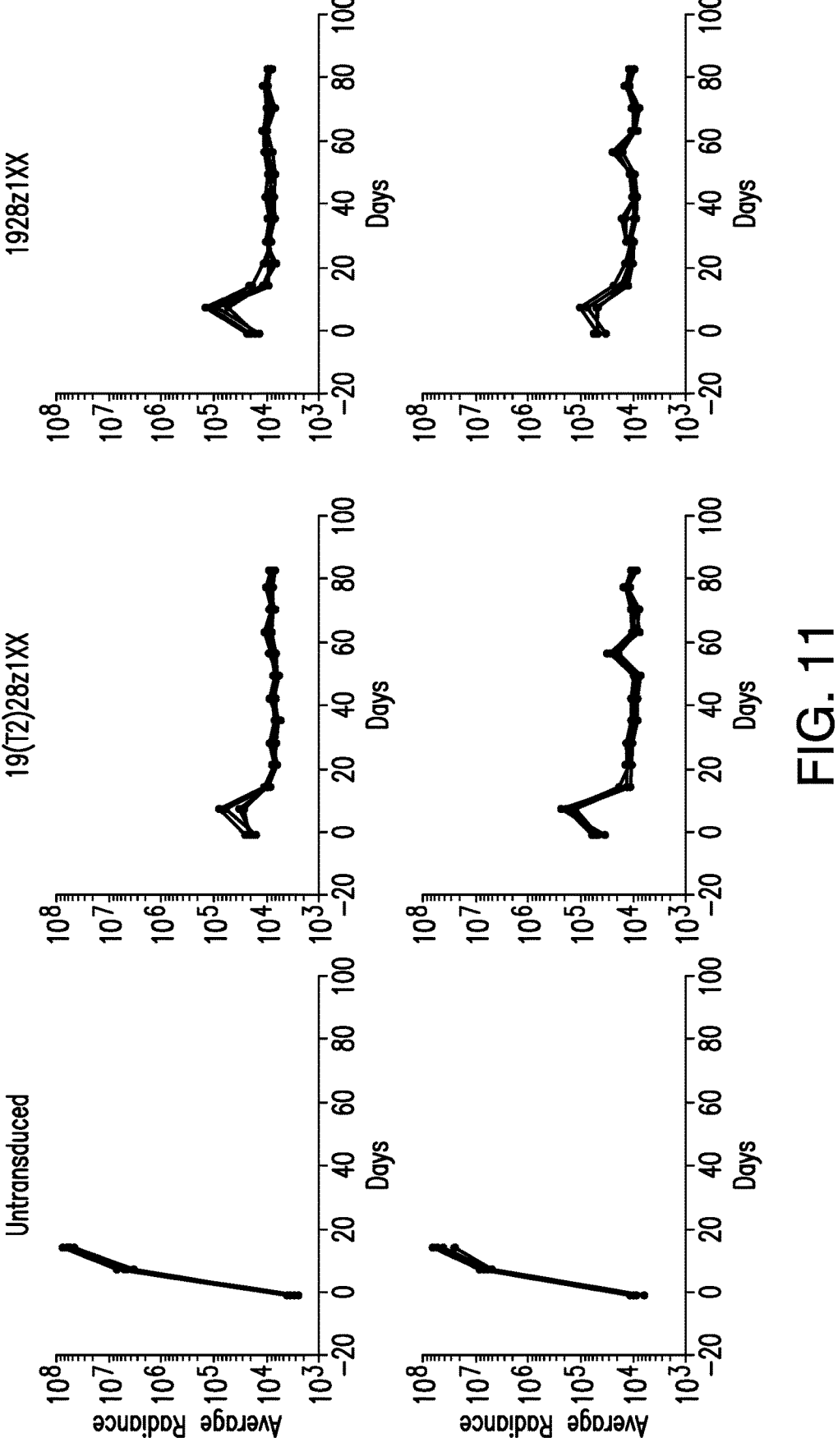

FIG. 11 depicts tumor elimination by #2 CAR T cells and 1928z-1XX CAR T cells. "19(T2)28z1xx" represents "#2 CAR".

Figure 12:
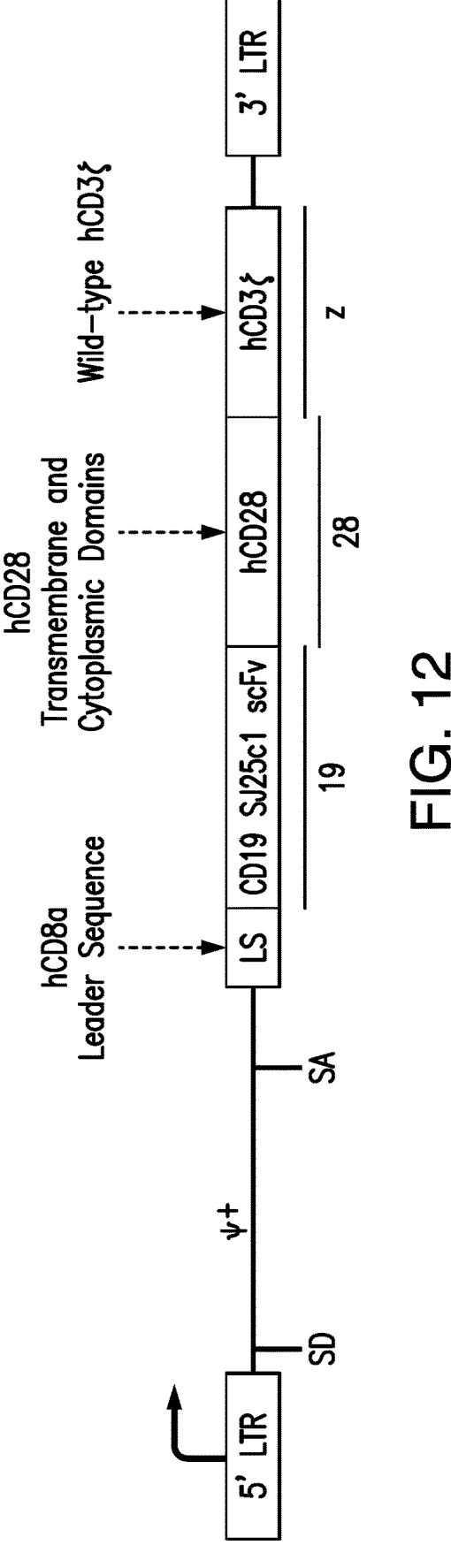

FIG. 12 depicts the gamma-retroviral vector comprising the 1928z CAR. The amino acid sequence for the wild-type hCD3ζ is shown in FIG. 9 as SEQ ID NO: 30.

Figure 13:
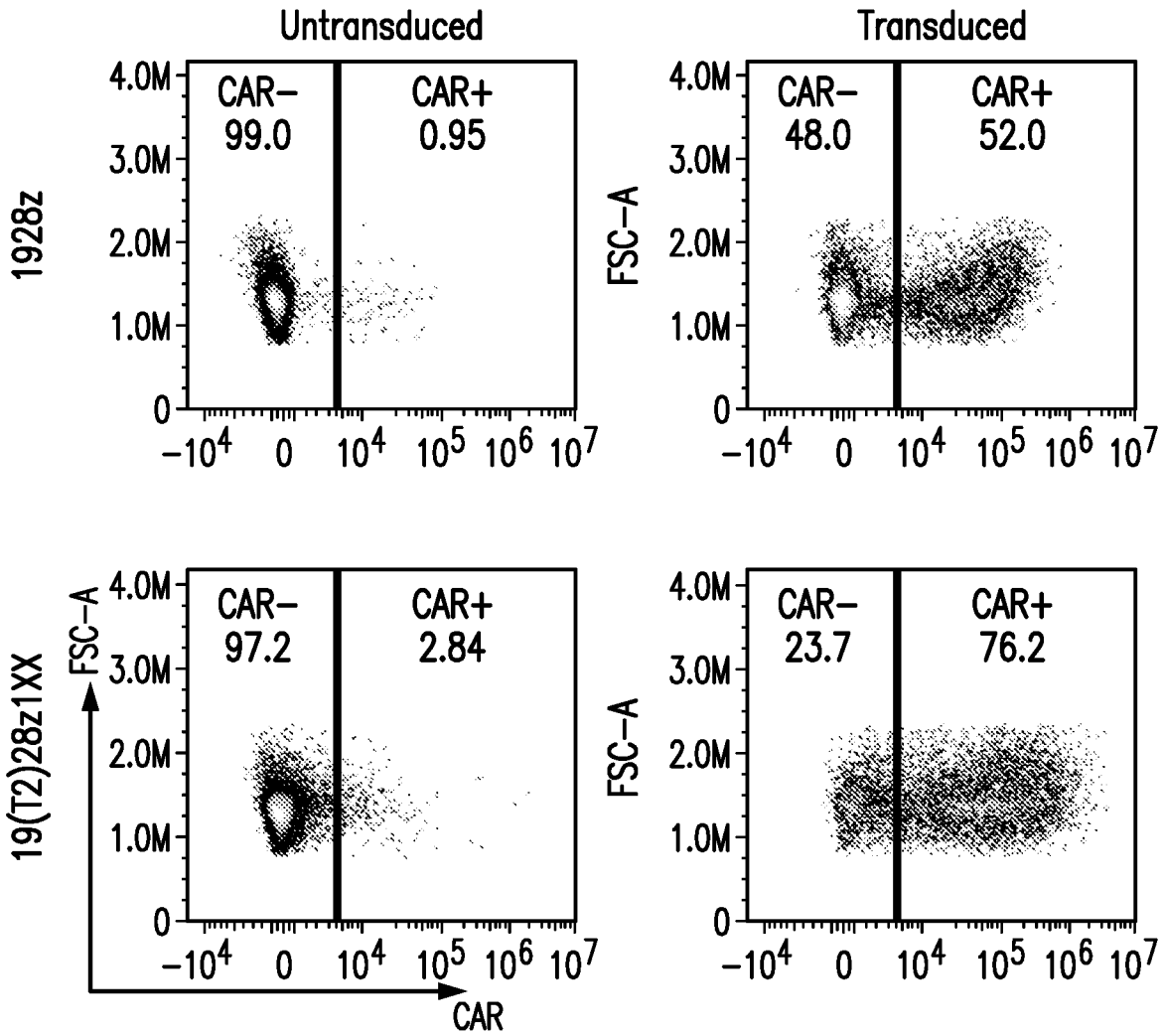

FIG. 13 depicts the CAR expression in the γ-retrovirally transduced CD4+ and CD8⁺ T cells. "19(T2)28z1XX" represents "#2 CAR".

Figure 14:
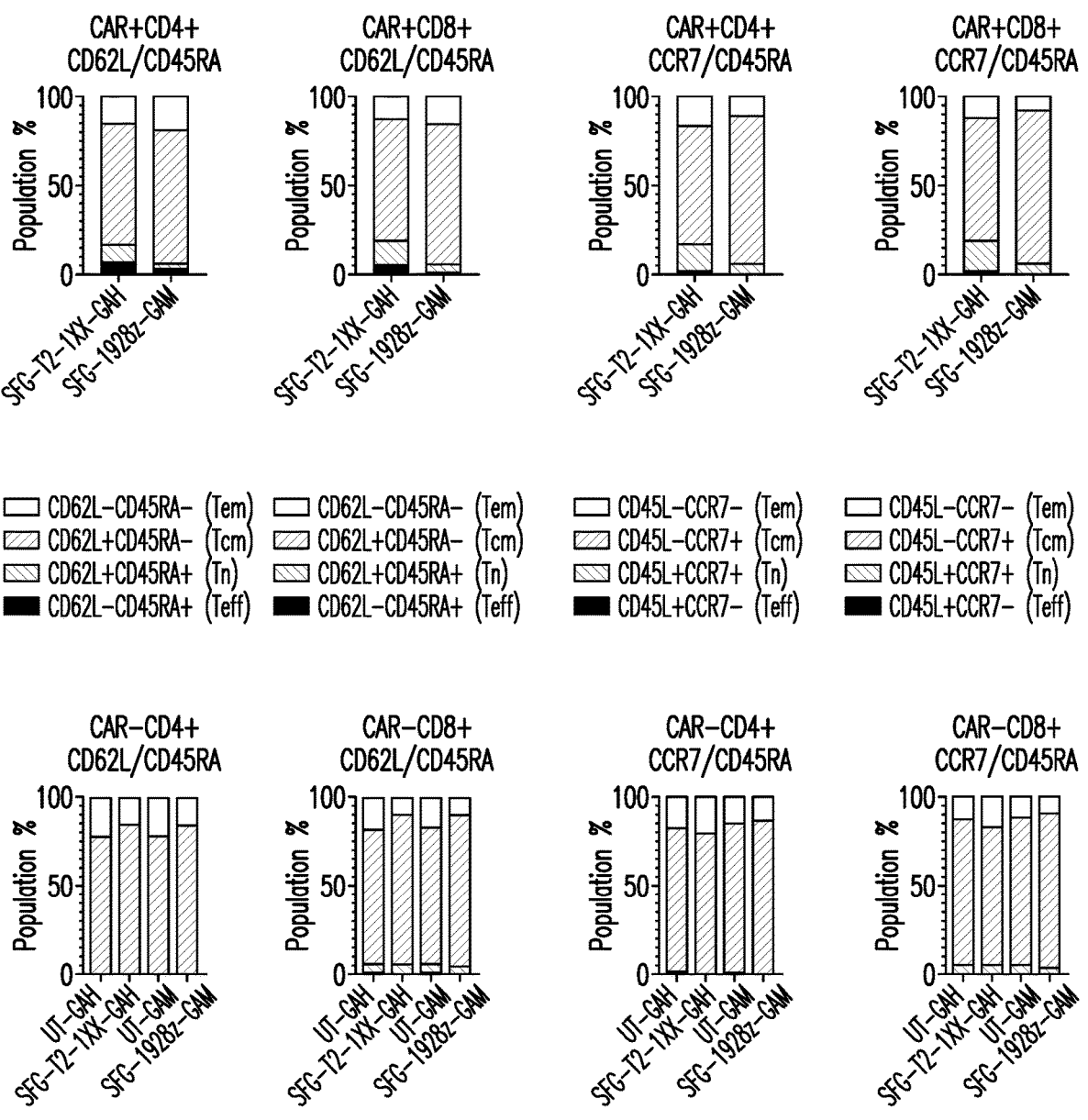
Figure 14:
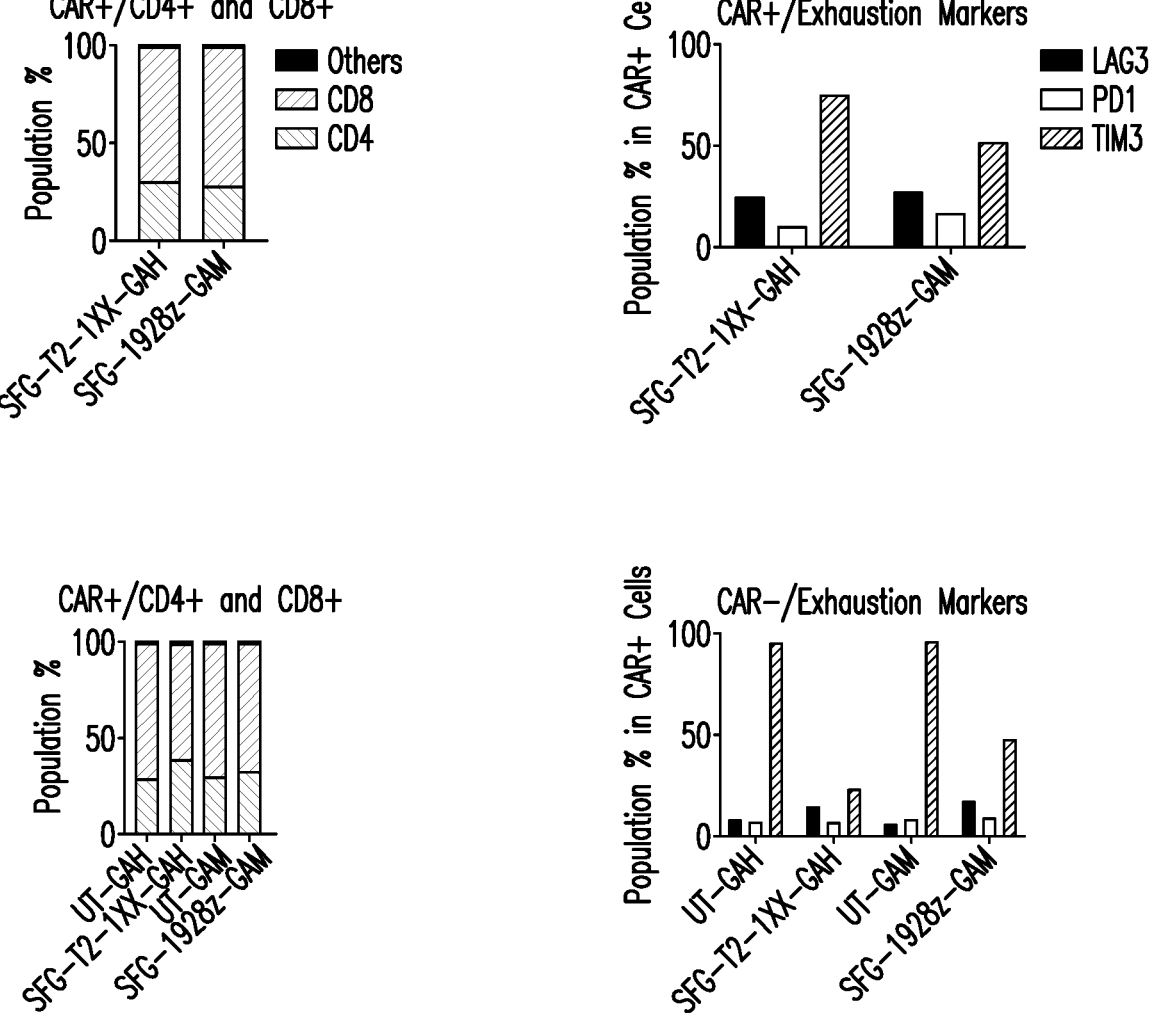

FIG. 14 depicts the phenotypes 1928z CAR T cells and #2 CAR T cells. "19(T2)28z1XX" represents "#2 CAR".

Figure 15:
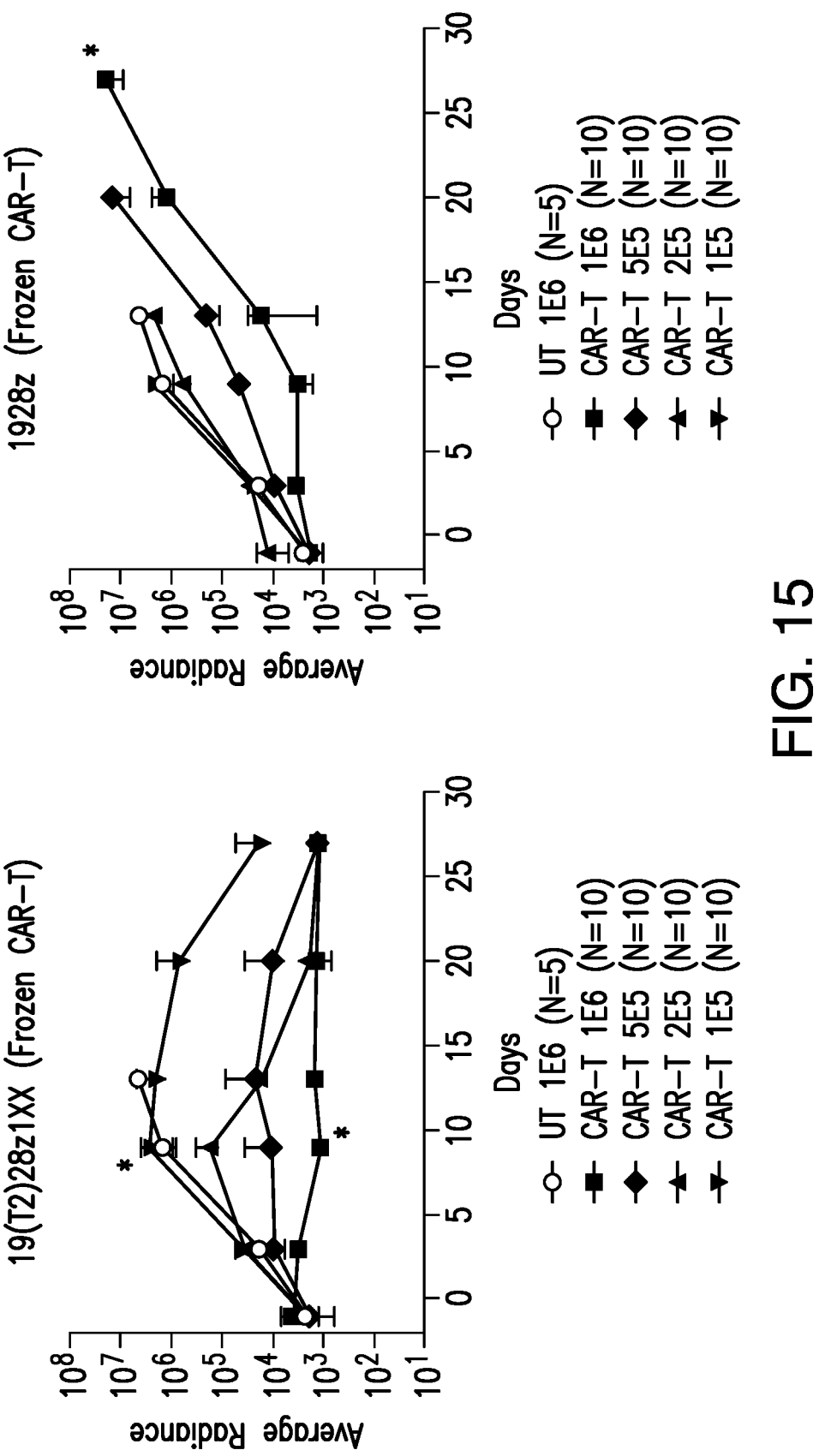

FIG. 15 depicts kinetics of tumor eradication by #2 CAR T cells and 1928z CAR T cells. "19(T2)28z1XX" represents "#2 CAR". Each curve represents the tumor burden in one mouse.

Figure 16:
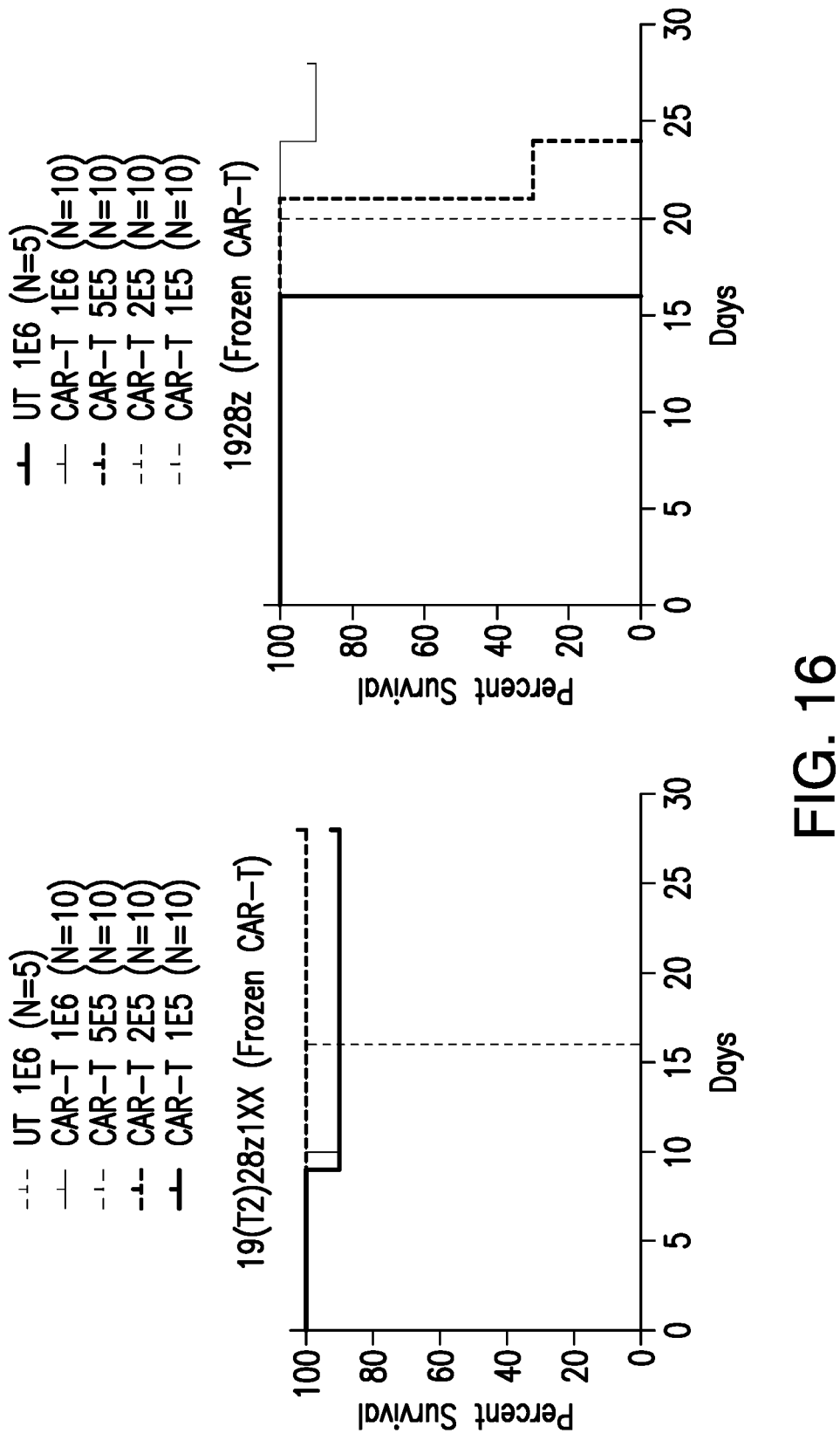

FIG. 16 depicts the survival of NALM6 leukemia-bearing mice post i.v. infusion of #2 CAR T cells or 1928z CAR T cells. "19(T2)28z1XX" represents "#2 CAR".

Figure 17:
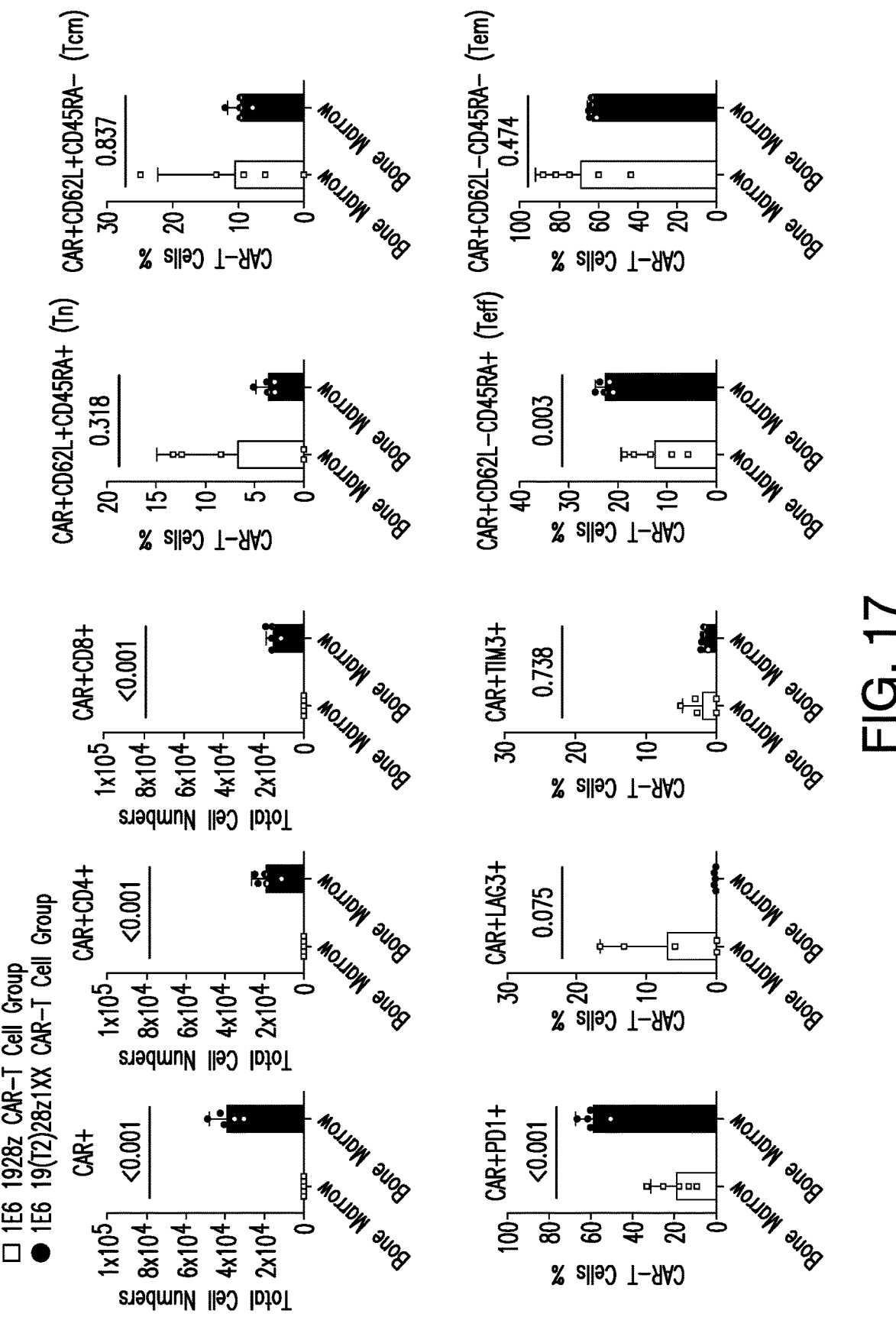

FIG. 17 depicts quantification and phenotyping of CAR T cells in the bone marrow of mice treated with #2 CAR T cells or 1928z CAR T cells (Day 17). All data are mean±s.e.m. and a two-tailed unpaired Student's t-test was used to calculate the p-values. "19(T2)28z1XX" represents "#2 CAR".

FIG. 18 depicts body weights of mice after treatment with #2 CAR T cells or 1928z CART cells. "19(T2)28z1XX" represents "#2 CAR". An asterisk indicates the timepoints when unscheduled death occurred. Shorter curves represent the loss of all mice at the indicated timepoint.

Figure 19:
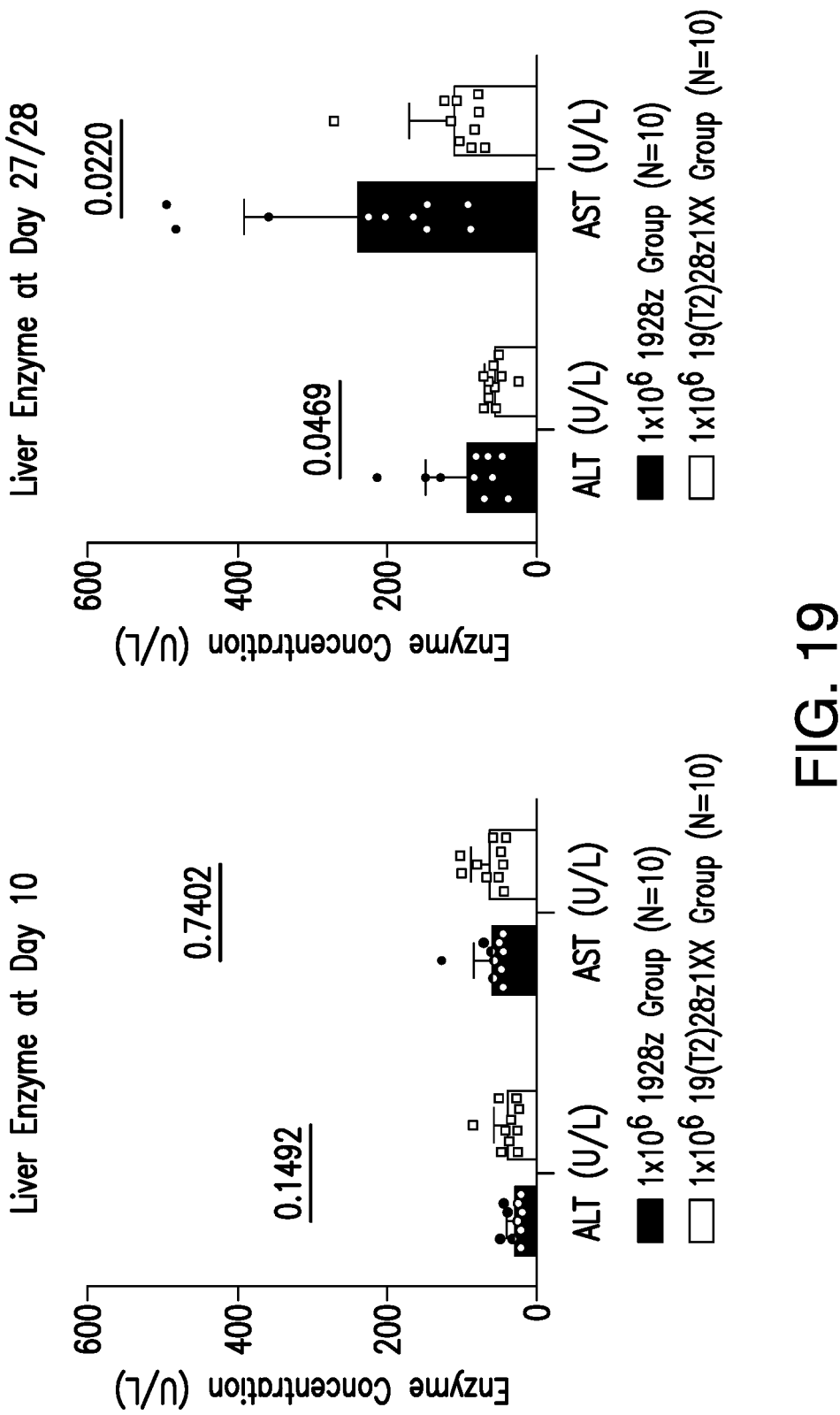

FIG. 19 depicts quantification of liver enzymes in the serum of mice treated with $1 \times 10^6$ CART cells at day 10 and day 27/28 post-infusion. Statistical comparisons were determined between two cohorts for the same day. All data are mean±s.e.m.; a two-tailed unpaired Student's t-test was used to calculate for p-values. "19(T2)28z1XX" represents "#2 CAR".

Figure 20:
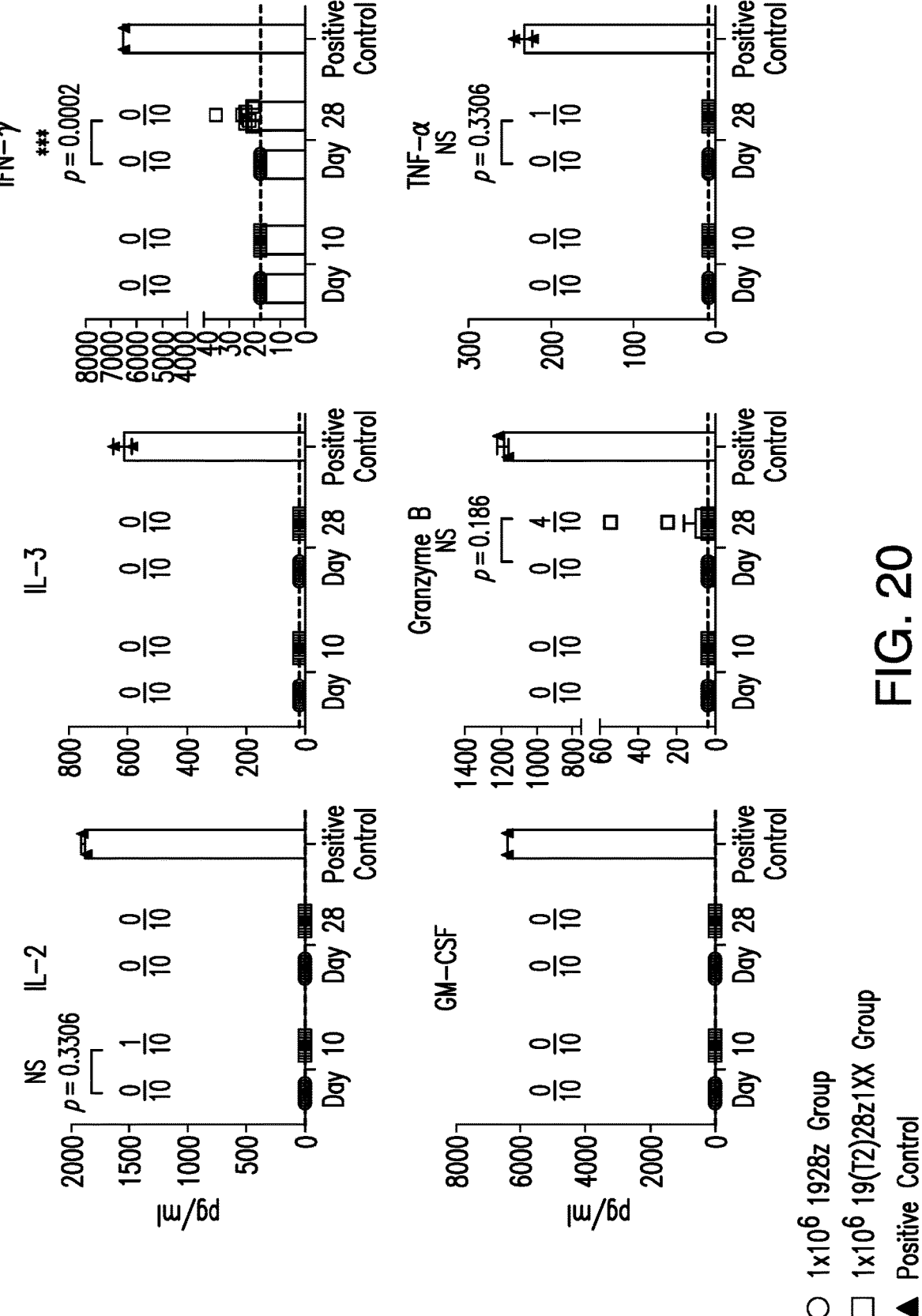

FIG. 20 depicts quantification of human cytokine levels in mice treated with $1 \times 10^6$ #2 CAR T cells or 1928z CAR T cells on day 10 and day 27/28 post-infusion. All data are mean±s.e.m.; a two-tailed unpaired Student's t-test was used to calculate the p-values. "19(T2)28z1XX" represents "#2 CAR".

Figure 21:
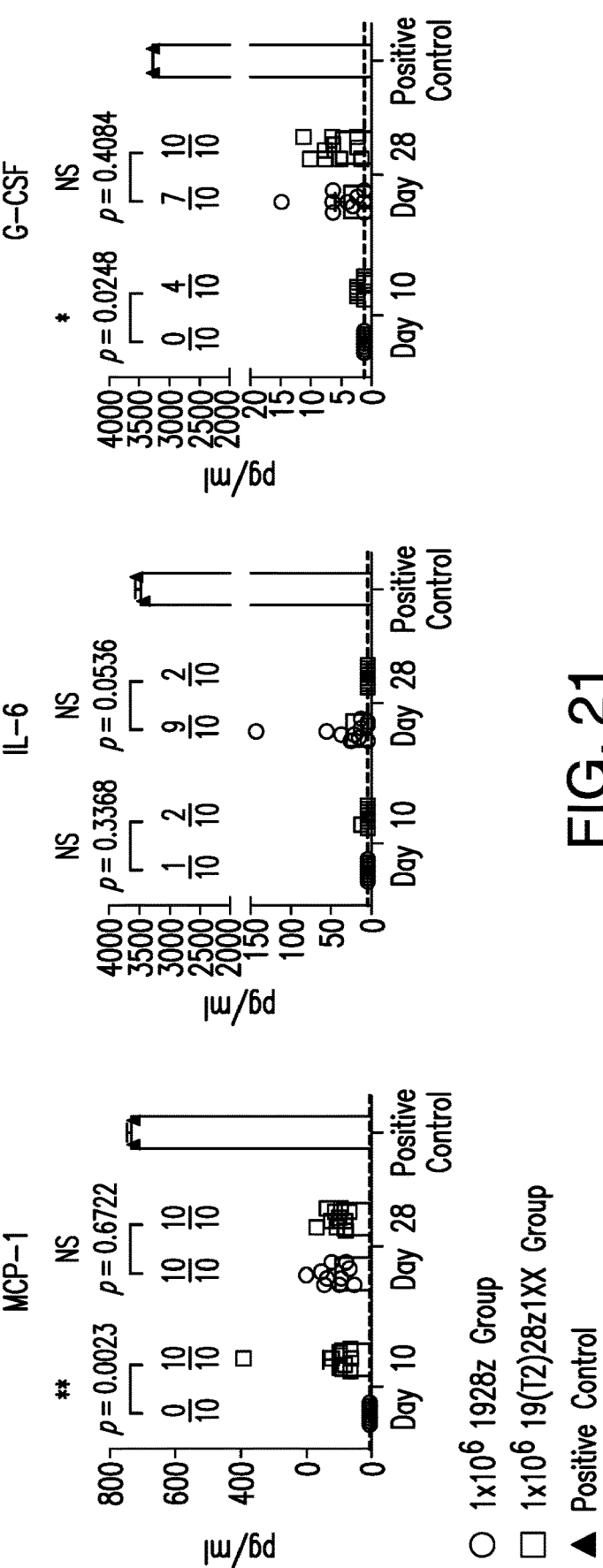

FIG. 21 quantification of mouse cytokine levels in mice treated with $1 \times 10^6$ #2 CAR T cells or 1928z CAR T cells on day 10 and day 27/28 post-infusion. All data are mean±s.e.m.; a two-tailed unpaired Student's t-test was used to calculate the p-values. "19(T2)28z1XX" represents "#2 CAR".

Figure 22:
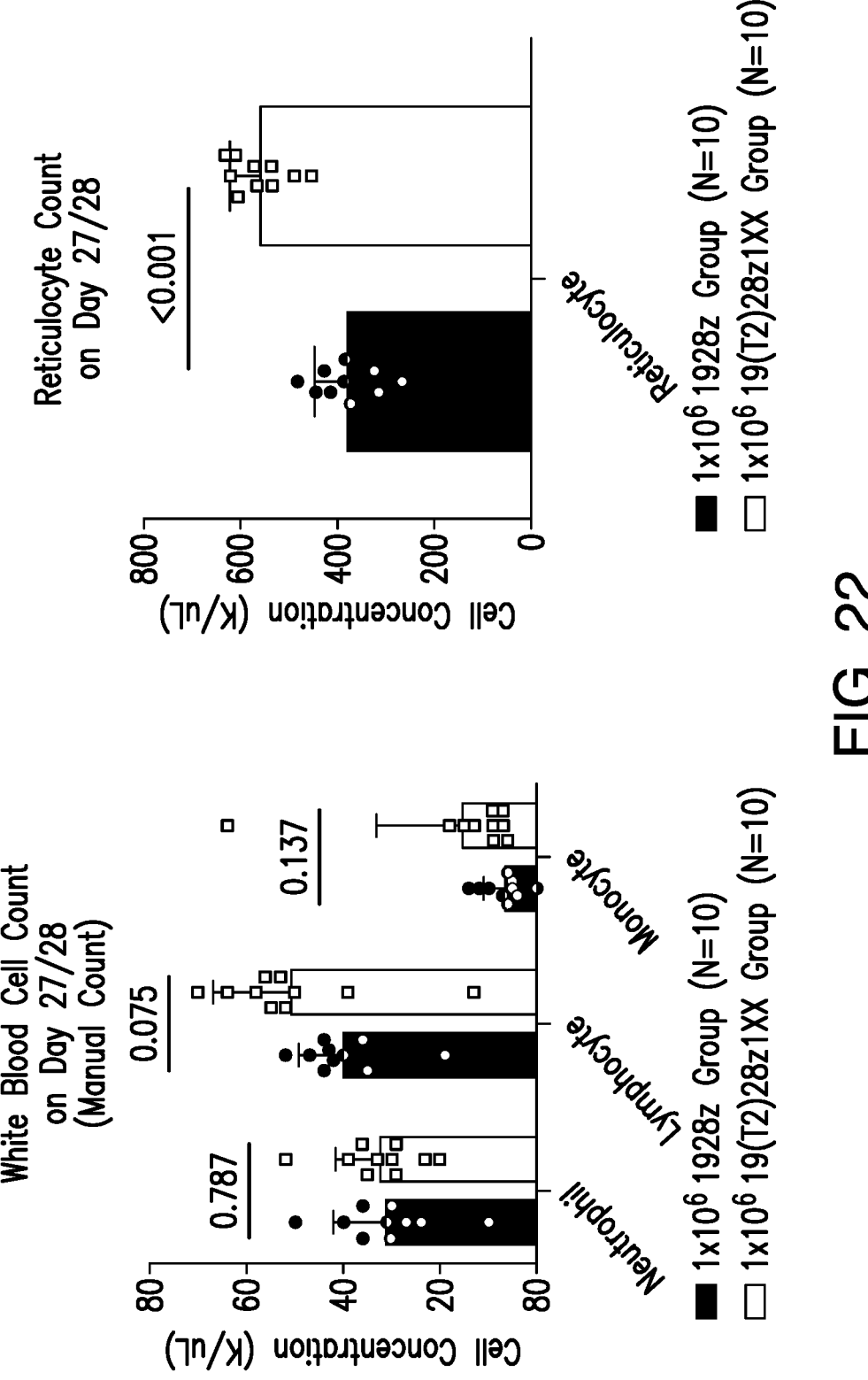

FIG. 22 depicts quantification of essential blood cells in mice treated with #2 CAR T cells and 1928z CAR T cells at day 27/28 post-infusion. All data are mean±s.e.m.; a two-tailed unpaired Student's t-test was used to calculate the p-values. "19(T2)28z1XX" represents "#2 CAR".

Figure 23:
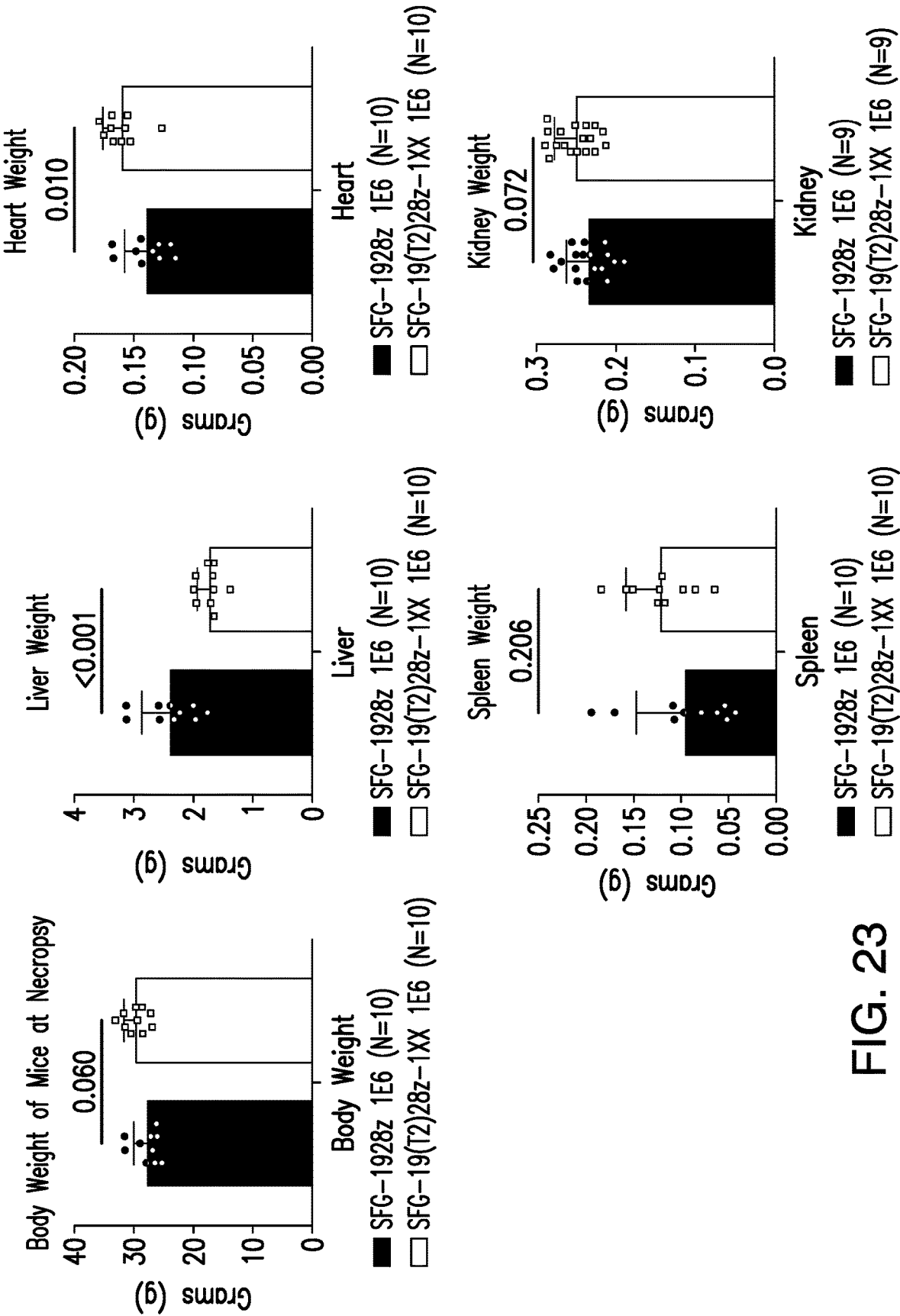

FIG. 23 depicts comparison of the body and critical organ weights of mice treated with #2 CAR T cells and 1928z CAR T cells at day 27/28 post-infusion. The number of mice per group is indicated in the graph legend. All data are mean±s.e.m.; a two-tailed unpaired Student's t-test was used to calculate for the p-values. "19(T2)28z1XX" represents "#2 CAR".

Figure 24:
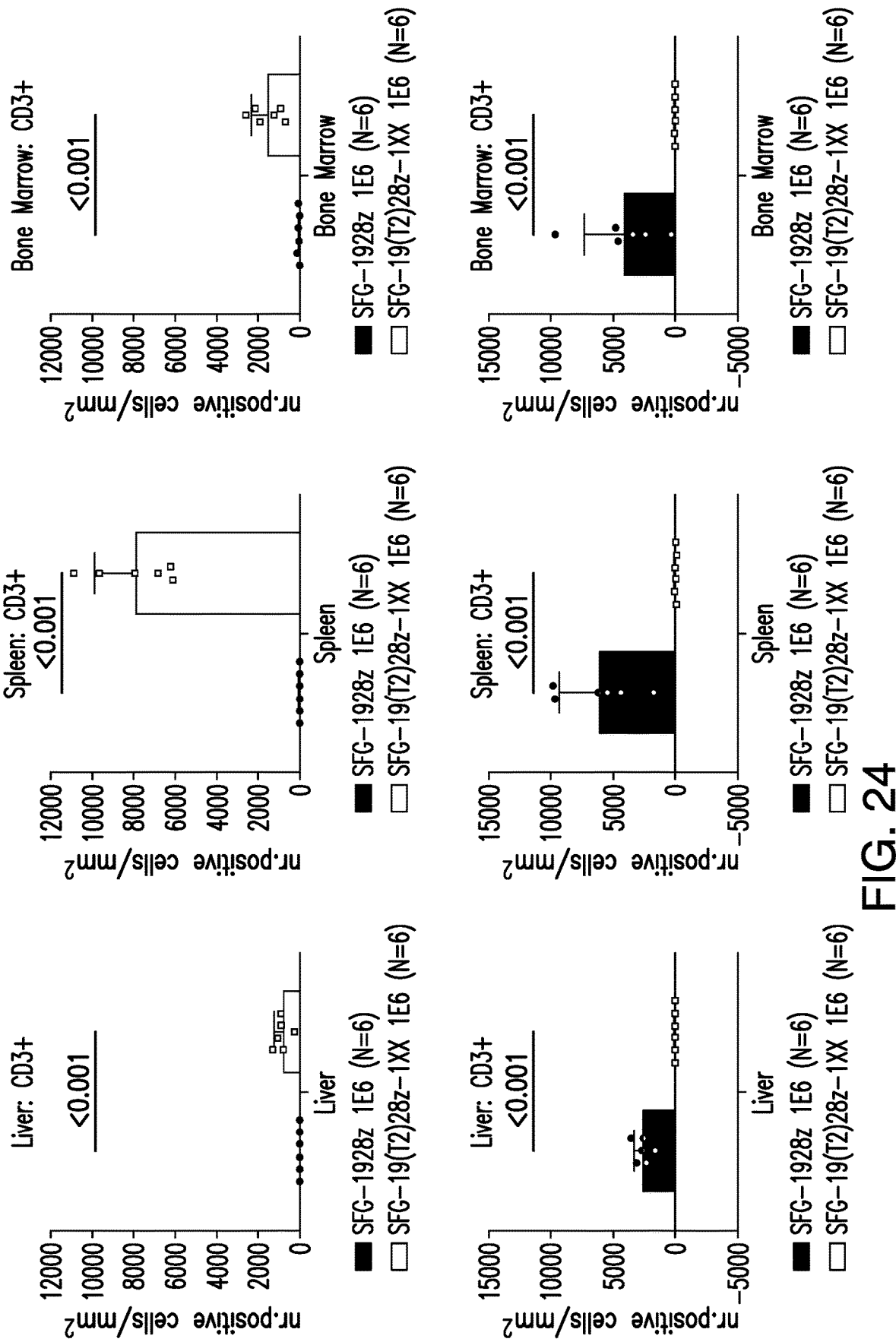

FIG. 24 depicts quantification of lymphocytes and tumor infiltration in the liver, spleen, and bone marrow of mice treated with CAR T cells. All data are mean±s.e.m.; a two-tailed unpaired Student's t-test was used to calculate for the p-values. "19(T2)28z1XX" represents "#2 CAR".

Figure 25:
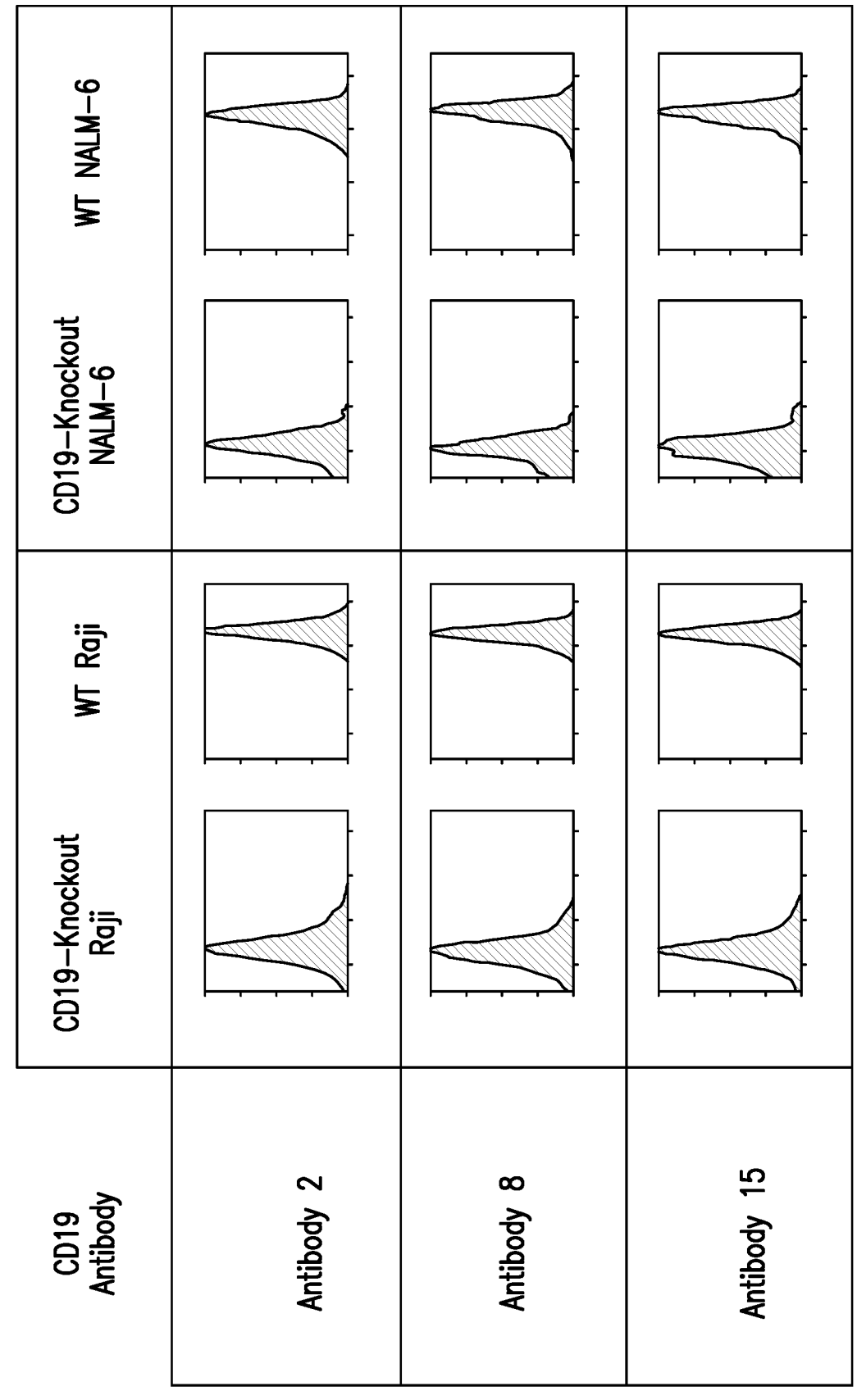

FIG. 25 depicts exemplary flow cytometry chromatograms of anti-CD19 antibodies binding to CD19 expressing Raji and NALM-6 cells wild type and CD19 knockout.

Figure 26A:
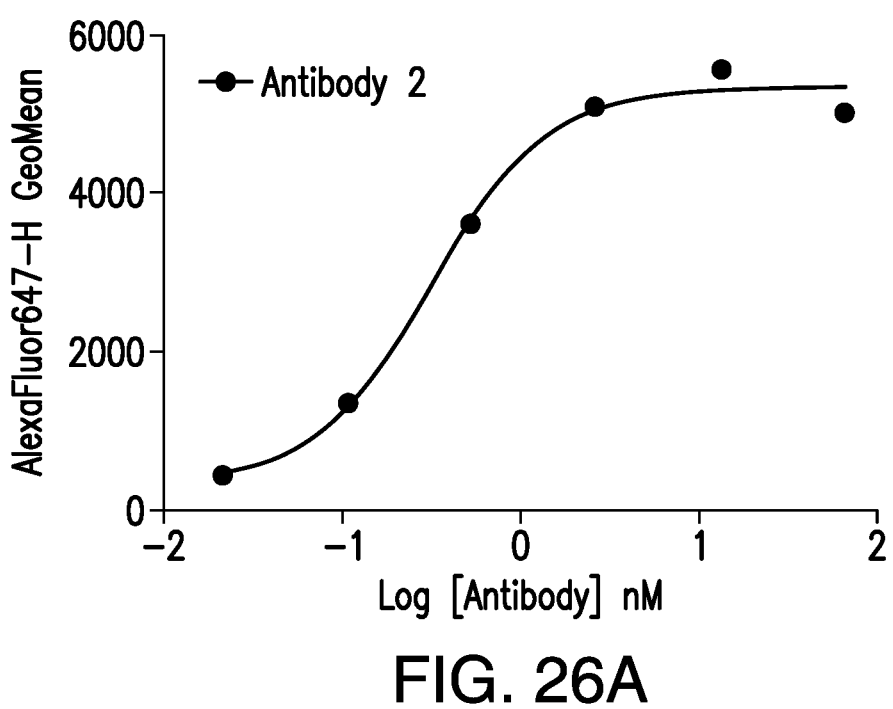
Figure 26B:
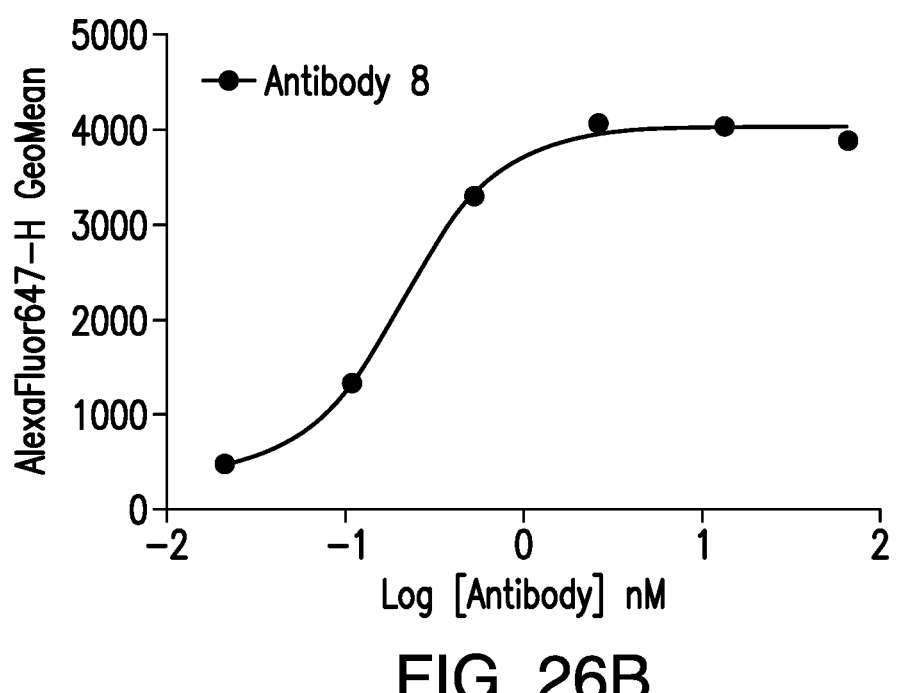
Figure 26C:
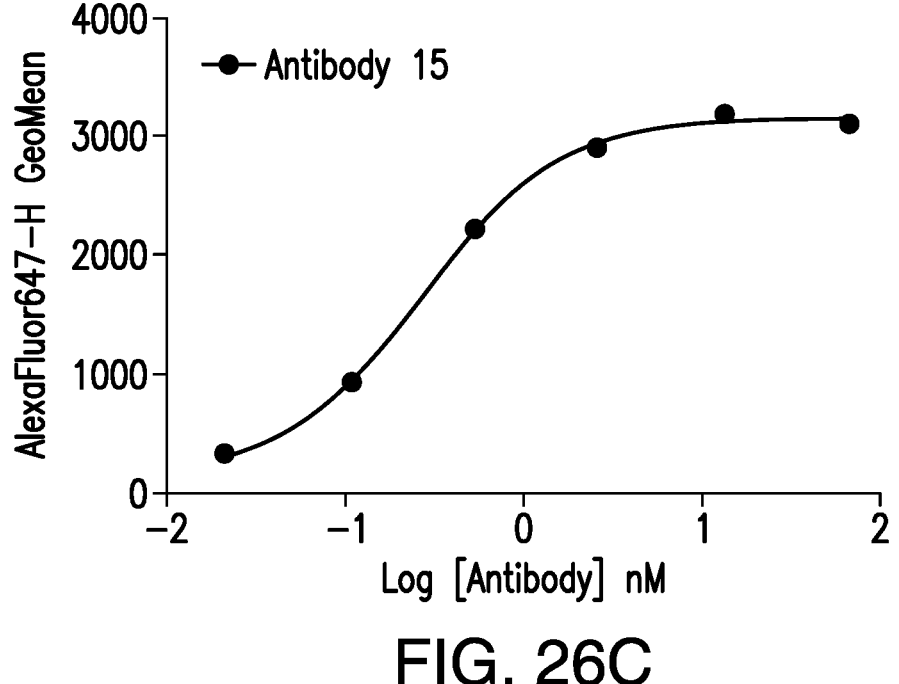

FIGS. 26A-26C depict exemplary binding curves of anti-CD19 antibodies binding CD19 on NALM-6 cells.

6. DETAILED DESCRIPTION

The presently disclosed subject matter provides chimeric antigen receptors (CARs) that specifically target CD19 and cells comprising such CD19-targeted CARs. The cells can be immunoresponsive cells, e.g., genetically modified immunoresponsive cells (e.g., T-cells or NK cells). The presently disclosed subject matter further provides uses of the cells and compositions comprising thereof for treatments, e.g., for treating a neoplasm. The presently disclosed CD19-targeted CARs shown to be safer and/or more potent than other CD19-targeted CARs, e.g., as evidenced by their greater persistence (see Examples 6 and 7). This greater persistence was also shown not to pose safety risk. Accordingly, the presently disclosed CD19-targeted CAR T cells may be used at a lower dose than most CD19-targeted CAR T cells that are used in current immunotherapy. The presently disclosed CD19-targeted CAR T cells are expected to be safer, e.g., and thus, fewer side effects, including, but not limited to, less incidence of cytokine release syndrome (CRS), and Neurotoxicity (NT).

Non-limiting embodiments of the present disclosure are described by the present specification and Examples.

For purposes of clarity of disclosure and not by way of limitation, the detailed description is divided into the following subsections:

5.1. Definitions;
5.2. CD19;
5.3. Chimeric Antigen Receptors (CARs);
5.4. Cells;
5.5. Nucleic Acid Molecules and Vectors;
5.6. Formulations and Administration; and
5.7. Methods of Treatment 5.1 Definitions Unless defined otherwise, all technical and scientific terms used herein have the meaning commonly understood by a person skilled in the art to which the presently disclosed subject matter belongs.

As used herein, the term "about" or "approximately" refers to within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. As used herein, the term "immunoresponsive cell" refers to a cell that functions in an immune response or a progenitor, or progeny thereof. In certain embodiments, the immunoresponsive cell is a cell of lymphoid lineage. Non-limiting examples of cells of lymphoid lineage include T-cells, Natural Killer (NK) cells, B cells, and stem cells from which lymphoid cells may be differentiated. In certain embodiments, the immunoresponsive cell is a cell of myeloid lineage.

As used herein, the term "activates an immunoresponsive cell" refers to induction of signal transduction or changes in protein expression in the cell resulting in initiation of an immune response. For example, when CD3 chains cluster in response to ligand binding and immunoreceptor tyrosine-based inhibition motifs (ITAMs) a signal transduction cascade is produced. In certain embodiments, when a CAR binds to an antigen, a formation of an immunological synapse occurs that includes clustering of many molecules near the bound receptor (e.g. CD4 or CD8, CD3$\gamma$/$\delta$/$\epsilon$/$\zeta$, etc.). This clustering of membrane bound signaling molecules allows for ITAM motifs contained within the CD3 chains to become phosphorylated. This phosphorylation in turn initiates a T-cell activation pathway ultimately activating transcription factors, such as NF-$\kappa$B and AP-1. These transcription factors induce global gene expression of the T-cell to increase IL-2 production for proliferation and expression of master regulator T-cell proteins in order to initiate a T-cell mediated immune response.

As used herein, the term "stimulates an immunoresponsive cell" refers to a signal that results in a robust and sustained immune response. In certain embodiments, this occurs after immunoresponsive cell (e.g., T-cell) activation or concomitantly mediated through receptors including, but not limited to, CD28, 4-1BB, OX40, CD40 and ICOS. Receiving multiple stimulatory signals can be important to mount a robust and long-term T-cell mediated immune response. T-cells can quickly become inhibited and unresponsive to antigen. While the effects of these co-stimulatory signals may vary, they generally result in increased gene expression in order to generate long lived, proliferative, and anti-apoptotic T-cells that robustly respond to antigen for complete and sustained eradication.

As used herein, "complementarity determining regions" or "CDRs" are defined as the complementarity determining region amino acid sequences of an antibody which are the hypervariable regions of immunoglobulin heavy and light chains. In certain embodiments, a "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283: 1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. In some embodiments, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions. Generally, antibodies comprise three heavy chain and three light chain CDRs or CDR regions in the variable region. CDRs provide the majority of contact residues for the binding of the antibody to the antigen or epitope. In certain embodiments, the CDRs regions are delineated using the Kabat numbering system.

As used herein, the term "single-chain variable fragment" or "scFv" refers to a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker.

In certain embodiments, the linker comprises or consists of the amino acid sequence set forth in SEQ ID NO: 1, which is provided below:

[SEQ ID NO: 1]
GGGGSGGGGSGGGGS

In certain embodiments, the linker comprises or consists of the amino acid sequence set forth in SEQ ID NO: 2, which is provided below:

[SEQ ID NO: 2]
GGGGSGGGGSGGGSGGGGS

In certain embodiments, the linker comprises or consists of the amino acid sequence set forth in SEQ ID NO: 3, which is provided below:

[SEQ ID NO: 3]
GGGGSGGGGSGGGGSGGGSGGGGS

In certain embodiments, the linker comprises or consists of the amino acid sequence set forth in SEQ ID NO: 4, which is provided below:

[SEQ ID NO: 4]
GGGGSGGGGSGGGGSGGGGSGGGGSGGGGS

As used herein, the term "substantially identical" or "substantially homologous" refers to a polypeptide or a nucleic acid molecule exhibiting at least about 50% identical or homologous to a reference amino acid sequence (for example, any of the amino acid sequences described herein) or a reference nucleic acid sequence (for example, any of the nucleic acid sequences described herein). In certain embodiments, such a sequence is at least about 60%, at least about 65%, at least about 70%, at least about 75%, at least about 80%, at least about 85%, at least about 90%, at least about 95%, at least about 99%, or at least about 100% identical or homologous to the amino acid sequence or the nucleic acid sequence used for comparison.

Sequence identity can be measured by using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e-3 and e-100 indicating a closely related sequence.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6. Additionally or alternatively, the amino acids sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the specified sequences (e.g., heavy and light chain variable region sequences of scFv703) disclosed herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used.

As used herein, the term "a conservative sequence modification" refers to an amino acid modification that does not significantly affect or alter the binding characteristics of the presently disclosed CD19-targeted CAR (e.g., the extracellular antigen-binding domain of the CAR) comprising the amino acid sequence. Conservative modifications can include amino acid substitutions, additions and deletions. Modifications can be introduced into the extracellular antigen-binding domain of the presently disclosed CAR by standard techniques known in the art, such as site-directed mutagenesis and PCR-mediated mutagenesis. Amino acids can be classified into groups according to their physicochemical properties such as charge and polarity. Conservative amino acid substitutions are ones in which the amino acid residue is replaced with an amino acid within the same group. For example, amino acids can be classified by charge: positively-charged amino acids include lysine, arginine, histidine, negatively-charged amino acids include aspartic acid, glutamic acid, neutral charge amino acids include alanine, asparagine, cysteine, glutamine, glycine, isoleucine, leucine, methionine, phenylalanine, proline, serine, threonine, tryptophan, tyrosine, and valine. In addition, amino acids can be classified by polarity: polar amino acids include arginine (basic polar), asparagine, aspartic acid (acidic polar), glutamic acid (acidic polar), glutamine, histidine (basic polar), lysine (basic polar), serine, threonine, and tyrosine; non-polar amino acids include alanine, cysteine, glycine, isoleucine, leucine, methionine, phenylalanine, proline, tryptophan, and valine. Thus, one or more amino acid residues within a CDR region can be replaced with other amino acid residues from the same group and the altered antibody can be tested for retained function (i.e., the functions set forth in (c) through (1) above) using the functional assays described herein. In certain embodiments, no more than one, no more than two, no more than three, no more than four, no more than five residues within a specified sequence or a CDR region are altered.

As used herein, the term "effective amount" refers to an amount sufficient to affect a beneficial or desired clinical result upon treatment. An effective amount can be administered to a subject in one or more doses. In certain embodiments, an effective amount can be an amount that is sufficient to palliate, ameliorate, stabilize, reverse or slow the progression of the disease, or otherwise reduce the pathological consequences of the disease. The effective amount can be determined by a physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the cells administered.

As used herein, the term "neoplasm" refers to a disease characterized by the pathological proliferation of a cell or tissue and its subsequent migration to or invasion of other tissues or organs. Neoplasia growth is typically uncontrolled and progressive, and occurs under conditions that would not elicit, or would cause cessation of, multiplication of normal cells. Neoplasm can affect a variety of cell types, tissues, or organs, including but not limited to an organ selected from the group consisting of bladder, bone, brain, breast, cartilage, glia, esophagus, fallopian tube, gallbladder, heart, intestines, kidney, liver, lung, lymph node, nervous tissue, ovaries, pancreas, prostate, skeletal muscle, skin, spinal cord, spleen, stomach, testes, thymus, thyroid, trachea, urogenital tract, ureter, urethra, uterus, and vagina, or a tissue or cell type thereof. Neoplasms include cancers, such as sarcomas, carcinomas, or plasmacytomas (malignant tumor of the plasma cells). The neoplasm can a primary tumor or primary cancer.

As used herein, the term "signal sequence" or "leader sequence" refers to a peptide sequence (e.g., 5, 10, 15, 20, 25 or 30 amino acids) present at the N-terminus of newly synthesized proteins that directs their entry to the secretory pathway.

The terms "comprises", "comprising", and are intended to have the broad meaning ascribed to them in U.S. Patent Law and can mean "includes", "including" and the like.

As used herein, "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

An "individual" or "subject" herein is a vertebrate, such as a human or non-human animal, for example, a mammal. Mammals include, but are not limited to, humans, primates, farm animals, sport animals, rodents and pets. Non-limiting examples of non-human animal subjects include rodents such as mice, rats, hamsters, and guinea pigs; rabbits; dogs; cats; sheep; pigs; goats; cattle; horses; and non-human primates such as apes and monkeys.

5.2. CD19

CD19 is a cell-surface 95 kDa glycoprotein present on normal B cells from early in their development until differentiation into plasma cells. CD19 is not present in other normal tissues, including pluripotent blood stem cells. It is expressed in B cell lymphomas, acute lymphoblastic leukemia (ALL), chronic lymphocytic leukemia (CLL), hairy cell leukemias, and a subset of acute myelogenous leukemias making it an attractive target for immunotherapy with minimal risk of autoimmune disease (other than B cell aplasia) or irreversible bone marrow toxicity.

CD19 is a member of the immunoglobulin superfamily and a component of a cell surface signal transduction complex that includes Leu13, CD81, and CD21, which positively regulates signal transduction through the B cell receptor.

In certain embodiments, the presently disclosed CAR binds to human CD19. In certain embodiments, the human CD19 comprises or consists of the amino acid sequence with a NCBI Reference No: NP 001171569.1 (SEQ ID NO: 5), or a fragment thereof.

```
SEQ ID NO: 5 is provided below:
                                    [SEQ ID NO: 5]
MPPPRLLFFL LFLTPMEVRP EEPLVVKVEE GDNAVLQCLK

GTSDGPTQQL TWSRESPLKP FLKLSLGLPG LGIHMRPLAI

WLFIFNVSQQ MGGFYLCQPG PPSEKAWQPG WTVNVEGSGE

LFRWNVSDLG GLGCGLKNRS SEGPSSPSGK LMSPKLYVWA

KDRPEIWEGE PPCLPPRDSL NQSLSQDLTM APGSTLWLSC

GVPPDSVSRG PLSWTHVHPK GPKSLLSLEL KDDRPARDMW

VMETGLLLPR ATAQDAGKYY CHRGNLTMSF HLEITARPVL

WHWLLRTGGW KVSAVTLAYL IFCLCSLVGI LHLQRALVLR

RKRKRMTDPT RRFFKVTPPP GSGPQNQYGN VLSLPTPTSG

LGRAQRWAAG LGGTAPSYGN PSSDVQADGA LGSRSPPGVG

PEEEEGEGYE EPDSEEDSEF YENDSNLGQD QLSQDGSGYE

NPEDEPLGPE DEDSFSNAES YENEDEELTQ PVARTMDFLS

PHGSAWDPSR EATSLAGSQS YEDMRGILYA APQLRSIRGQ

PGPNHEEDAD SYENMDNPDG PDPAWGGGGR MGTWSTR
```

In certain embodiments, the human CD19 comprises or consists of the amino acid sequence with a NCBI Reference No: NP 001761.3 (SEQ ID NO: 6), or a fragment thereof.

```
SEQ ID NO: 6 is provided below:
                                    [SEQ ID NO: 6]
MPPPRLLFFL LFLTPMEVRP EEPLVVKVEE GDNAVLQCLK

GTSDGPTQQL TWSRESPLKP FLKLSLGLPG LGIHMRPLAI

WLFIFNVSQQ MGGFYLCQPG PPSEKAWQPG WTVNVEGSGE

LFRWNVSDLG GLGCGLKNRS SEGPSSPSGK LMSPKLYVWA

KDRPEIWEGE PPCLPPRDSL NQSLSQDLTM APGSTLWLSC
```

-continued

```
GVPPDSVSRG PLSWTHVHPK GPKSLLSLEL KDDRPARDMW

VMETGLLLPR ATAQDAGKYY CHRGNLTMSF HLEITARPVL

WHWLLRTGGW KVSAVTLAYL IFCLCSLVGI LHLQRALVLR

RKRKRMTDPT RRFFKVTPPP GSGPQNQYGN VLSLPTPTSG

LGRAQRWAAG LGGTAPSYGN PSSDVQADGA LGSRSPPGVG

PEEEGEGYE EPDSEEDSEF YENDSNLGQD QLSQDGSGYE

NPEDEPLGPE DEDSFSNAES YENEDEELTQ PVARTMDFLS

PHGSAWDPSR EATSLGSQSY EDMRGILYAA PQLRSIRGQP

GPNHEEDADS YENMDNPDGP DPAWGGGGRM GTWSTR
```

In certain embodiments, the CAR binds to the extracellular domain of CD19. In certain embodiments, the CAR binds to the extracellular domain of human CD19. In certain embodiments, the extracellular domain of human CD19 comprises or consists of amino acids 20 to 291 of SEQ ID NO: 5. In certain embodiments, the extracellular domain of human CD19 comprises or consists of amino acids 20 to 291 of SEQ ID NO: 6.

In certain embodiments, the CD19 comprises or consists of an amino acid sequence that is at least about 80%, at least about 85%, at least about 90%, at least about 95%, at least about 96%, at least about 97%, at least about 98%, at least about 99%, or at least about 100% identical to the amino acid sequence set forth in SEQ ID NO: 5 or a fragment thereof.

In certain embodiments, the CD19 comprises or consists of an amino acid sequence that is at least about 80%, at least about 85%, at least about 90%, at least about 95%, at least about 96%, at least about 97%, at least about 98%, at least about 99%, or at least about 100% identical to the amino acid sequence set forth in SEQ ID NO: 6 or a fragment thereof.

5.3. Chimeric Antigen Receptors (CARs)

CARs are engineered receptors, which graft or confer a specificity of interest onto an immune effector cell. CARs can be used to graft the specificity of a monoclonal antibody onto a cell, e.g., an immunoresponsive cell, e.g., a T cell or a NK cell; with transferring of their coding sequence facilitated by retroviral vectors.

There are three generations of CARs. "First generation" CARs are typically composed of an extracellular antigen-binding domain (e.g., a scFv), which is fused to a transmembrane domain, which is fused to an intracellular signaling domain. "First generation" CARs can provide de novo antigen recognition and cause activation of both CD4$^+$ and CD8$^+$ T-cells through their CD3ζ chain signaling domain in a single fusion molecule, independent of HLA-mediated antigen presentation. "Second generation" CARs add an intracellular signaling domain from a co-stimulatory molecule (including, but not limited to, CD28, 4-1BB, ICOS, OX40) to the cytoplasmic tail of the CAR to provide additional signals to the cell. "Second generation" CARs comprise those that provide both co-stimulation (e.g., CD28 or 4-1BB) and activation (CD3ζ). "Third generation" CARs comprise those that provide multiple co-stimulation (e.g., CD28 and 4-1BB) and activation (CD3ζ). In certain embodiments, the CD19-targeted CAR is a first-generation CAR. In certain embodiments, the CD19-targeted CAR does not comprise an intracellular signaling domain of a co-stimulatory molecule. In certain embodiments, the CD19-targeted CAR is a second-generation CAR. In certain embodiments, the CD19-targeted CAR comprises an intracellular signaling domain of a co-stimulatory molecule In certain embodiments, the CAR comprises an extracellular antigen-binding domain that specifically binds to CD19, a transmembrane domain, and an intracellular signaling domain. In certain embodiments, the extracellular antigen-binding domain is fused to the transmembrane domain, which is fused to the intracellular signaling domain.

5.3.1. Extracellular Antigen-Binding Domain of A CAR

In certain embodiments, the extracellular antigen-binding domain of the CAR comprises or is a scFv. The scFv can be a human scFv, a humanized scFv, or a murine scFv. In certain embodiments, the scFv is a human scFv. The scFv can be derived from fusing the variable heavy and light regions of an antibody. Alternatively or additionally, the scFv may be derived from Fab's (instead of from an antibody, e.g., obtained from Fab libraries).

In certain embodiments, the extracellular antigen-binding domain of the CAR comprises or is a Fab. In certain embodiments, the Fab is crosslinked. In certain embodiments, the extracellular antigen-binding domain of the CAR comprises or is a F(ab)$_2$.

Any of the foregoing molecules may be comprised in a fusion protein with a heterologous sequence to form the extracellular antigen-binding domain of the CAR.

In certain embodiments, the extracellular antigen-binding domain of the CAR binds to CD19 (e.g., human CD19) with a dissociation constant ($K_d$) of at least about $1\times10^{-6}$ M, at least about $1\times10^{-7}$ M, at least about $1\times10^{-8}$ M, at least about $1\times10^{-9}$ M, or at least about $1\times10^{-10}$ M. In certain embodiments, the extracellular antigen-binding domain of the CAR binds to CD19 (e.g., human CD19) with a dissociation constant ($K_d$) of at least about $2\times10^{-8}$ M. In certain embodiments, the extracellular antigen-binding domain of the CAR binds to CD19 (e.g., human CD19) with a dissociation constant ($K_d$) of between about $2\times10^{-8}$M and about $8\times10^{-9}$M.

In certain embodiments, the extracellular antigen-binding domain of the CAR binds to CD19 (e.g., human CD19) with a dissociation constant ($K_d$) of between about 1 nM and 50 nM, between about 5 nM and 30 nM, between about 5 nM and 25 nM, or between about 8 nM and 20 nM. In certain embodiments, the extracellular antigen-binding domain of the CAR binds to CD19 (e.g., human CD19) with a dissociation constant ($K_d$) of at least about 50 nM, at least about 40 nM, at least about 35 nM, at least about 30 nM, at least about 25 nM, at least about 20 nM, at least about 19 nM, at least about 18 nM, at least about 17 nM, at least about 16 nM, at least about 15 nM, at least about 14 nM, at least about 13 nM, at least about 12 nM, at least about 11 nM, at least about nM, at least about 9 nM, at least about 8 nM, at least about 7 nM, at least about 6 nM, or at least about 5 nM.

Binding of the extracellular antigen-binding domain of the CAR can be confirmed by, for example, enzyme-linked immunosorbent assay (ELISA), radioimmunoassay (RIA), FACS analysis, bioassay (e.g., growth inhibition), or Western Blot assay. Each of these assays generally detect the presence of protein-antibody complexes of particular interest by employing a labeled reagent (e.g., an antibody, or a scFv) specific for the complex of interest. For example, the scFv can be radioactively labeled and used in a radioimmunoassay (RIA) (see, for example, Weintraub, B., Principles of Radioimmunoassays, Seventh Training Course on Radio-ligand Assay Techniques, The Endocrine Society, March, 1986, which is incorporated by reference herein). The radioactive isotope can be detected by such means as the use of a γ counter or a scintillation counter or by autoradiography. In certain embodiments, the CD127-targeted extracellular antigen-binding domain is labeled with a fluorescent marker. Non-limiting examples of fluorescent markers include green fluorescent protein (GFP), blue fluorescent protein (e.g., EBFP, EBFP2, Azurite, and mKalama1), cyan fluorescent protein (e.g., ECFP, Cerulean, and CyPet), and yellow fluorescent protein (e.g., YFP, Citrine, Venus, and YPet). In certain embodiments, the CD19-targeted human scFv is labeled with a GFP.

In certain embodiments, the extracellular antigen-binding domain of the CAR comprises a heavy chain variable region $(V_H)$ and a light chain variable region $(V_L)$.

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9. SEQ ID NOs: 7-9 are provided below.

```
                                    [SEQ ID NO: 7]
        SYGMH

[SEQ ID NO: 8]
        LIWYDGSNKYYADSVKG

[SEQ ID NO: 9]
        PVEGLLRGFDY
```

In certain embodiments, the $V_H$ comprises an amino acid sequence that is at least about 80% (e.g., at least about 85%, at least about 90%, or at least about 95%) identical or homologous to the amino acid sequence set forth in SEQ ID NO: 10. For example, the $V_H$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 10. In certain embodiments, the $V_H$ comprises the amino acid sequence set forth in SEQ ID NO: 10. SEQ ID NO: 10 is provided below.

```
                                    [SEQ ID NO: 10]
QVQLVESGGGVVQPGRSLRLSCAASGFTFSSYGMHWVRQAPGKGLEWVAL

IWYDGSNKYYADSVKGRFTISRDNSKNTLYLQMNSLRAEDTAVYYCAKPV

EGLLRGFDYWGQGTLVTVSS
```

In certain embodiments, the $V_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 13 or a conservative modification thereof. In certain embodiments, the $V_L$ comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 13. SEQ ID NOs: 11-13 are provided below.

```
                                    [SEQ ID NO: 11]
        RASQSVSSSYLA

[SEQ ID NO: 12]
        GASSRAT

[SEQ ID NO: 13]
        QQAGAVPIT
```

In certain embodiments, the $V_L$ comprises an amino acid sequence that is at least about 80% (e.g., at least about 85%, at least about 90%, or at least about 95%) identical or homologous to the amino acid sequence set forth in SEQ ID NO: 14. For example, the $V_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 14. In certain embodiments, the $V_L$ comprises the amino acid sequence set forth in SEQ ID NO: 14. SEQ ID NO: 14 is provided below.

```
                                    [SEQ ID NO: 14]
EIVLTQSPGTLSLSPGERATLSCRASQSVSSSYLAWYQQKPGQAPRLLI

YGASSRATGIPDRFSGSGSGTDFTLTISRLEPEDFAVYYCQQAGAVPIT

FGGGTKVEIK
```

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and $V_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification, and a CDR3 comprising the amino acid sequence set forth in SEQ ID NO: 13 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the $V_L$ comprises a CDR1 comprising the amino acid sequence set forth in SEQ ID NO: 11; a CDR2 comprising the amino acid sequence set forth in SEQ ID NO: 12, and a CDR3 comprising the amino acid sequence set forth in SEQ ID NO: 13.

In certain embodiments, the $V_H$ comprises the amino acid sequence set forth in SEQ ID NO: 10, and the $V_L$ comprises the amino acid sequence set forth in SEQ ID NO: 14.

The $V_H$ the $V_L$ can be linked one after another, e.g., by a linker. The variable regions from the N- to the C-terminus can be $V_L$-$V_H$ or $V_L$-$V_H$. In certain embodiments, the $V_L$ is positioned at the N-terminus of the extracellular antigen-binding domain, i.e., the $V_H$ the $V_L$ are positioned from the N- to the C-terminus as $V_L$-$V_H$. In certain embodiments, the extracellular antigen-binding domain of the CAR is a scFv that comprises a $V_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and a $V_L$ comprising a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 13. In certain embodiments, the scFv comprises a $V_H$ comprising the amino acid sequence set forth in SEQ ID NO: 10, and a $V_L$ comprising the amino acid sequence set forth in SEQ ID NO: 14. In certain embodiments, the scFv comprises or consists of the amino acid sequence set forth in SEQ ID NO: 15. SEQ ID NO: 15 is provided below. In certain embodiments, the anti-CD19 scFv is designated as "#2 scFv".

[SEQ ID NO: 15]

EIVLTQSPGTLSLSPGERATLSCRASQSVSSSYLAWYQQKPGQAPRLLI

YGASSRATGIPDRFSGSGSGTDFTLTISRLEPEDFAVYYCQQAGAVPIT

FGGGTKVEIKGGGGSGGGGSGGGGSQVQLVESGGGVVQPGRSLRLSCAA

SGFTFSSYGMHWVRQAPGKGLEWVALIWYDGSNKYYADSVKGRFTISRD

NSKNTLYLQMNSLRAEDTAVYYCAKPVEGLLRGFDYWGQGTLVTVSS

In certain embodiments, the $V_L$ comprises a CDR1 comprising the amino acid sequence set forth in SEQ ID NO: 16 or a conservative modification thereof, a CDR2 comprising the amino acid sequence set forth in SEQ ID NO: 12 or a conservative modification thereof, and a CDR3 comprising the amino acid sequence set forth in SEQ ID NO: 17 or a conservative modification thereof. In certain embodiments, the $V_L$ comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 17. SEQ ID NOs: 16 and 17 are provided below.

[SEQ ID NO: 16]

RASQSVRSSYLA

[SEQ ID NO: 17]

QQLFDSPYT

In certain embodiments, the $V_L$ comprises an amino acid sequence that is at least about 80% (e.g., at least about 85%, at least about 90%, or at least about 95%) identical or homologous to the amino acid sequence set forth in SEQ ID NO: 18. For example, the $V_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 18. In certain embodiments, the $V_L$ comprises the amino acid sequence set forth in SEQ ID NO: 18. SEQ ID NO: 18 is provided below.

[SEQ ID NO: 18]

EIVLTQSPGTLSLSPGERATLSCRASQSVRSSYLAWYQQKPGQAPRLLI

YGASSRATGIPDRFSGSGSGTDFTLTISRLEPEDFAVYYCQQLFDSPYT

FGGGTKVEIK

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and the $V_L$ comprises a CDR1 comprising the amino acid sequence set forth in SEQ ID NO: 16 or a conservative modification thereof, a CDR2 comprising the amino acid sequence set forth in SEQ ID NO: 12 or a conservative modification, and a CDR3 comprising the amino acid sequence set forth in SEQ ID NO: 17 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the $V_L$ comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 17.

In certain embodiments, the $V_H$ comprises the amino acid sequence set forth in SEQ ID NO: 10, and the $V_L$ comprises the amino acid sequence set forth in SEQ ID NO: 18.

In certain embodiments, the $V_L$ is positioned at the N-terminus of the extracellular antigen-binding domain, i.e., the $V_H$ the $V_L$ are positioned from the N- to the C-terminus as $V_L$-$V_H$. In certain embodiments, the extracellular antigen-binding domain of the CAR is a scFv that comprises a $V_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and a $V_L$ comprising a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 17. In certain embodiments, the scFv comprises a $V_H$ comprising the amino acid sequence set forth in SEQ ID NO: 10, and a $V_L$ comprising the amino acid sequence set forth in SEQ ID NO: 18. In certain embodiments, the scFv comprises or consists of the amino acid sequence set forth in SEQ ID NO: 19. SEQ ID NO: 19 is provided below. In certain embodiments, the anti-CD19 scFv is designated as "#8 scFv".

[SEQ ID NO: 19]

IVLTQSPGTLSLSPGERATLSCRASQSVRSSYLAWYQQKPGQAPRLLIY

GASSRATGIPDRFSGSGSGTDFTLTISRLEPEDFAVYYCQQLFDSPYTF

QAPGKGLEWVALIWYDGSNKYYADSVKGRFTISRDNSKNTLYLQMNSLR

AGGGTKVEIKGGGGSGGGGSGGGGSQVQLVESGGGVVQPGRSLRLSCAA

SGFTFSSYGMHWVREDTAVYYCAKPVEGLLRGFDYWGQGTLVTVSS

In certain embodiments, the $V_L$ comprises a CDR1 comprising the amino acid sequence set forth in SEQ ID NO: 11 or a conservative modification thereof, a CDR2 comprising the amino acid sequence set forth in SEQ ID NO: 20 or a conservative modification thereof, and a CDR3 comprising the amino acid sequence set forth in SEQ ID NO: 21 or a conservative modification thereof. In certain embodiments, the V$_L$ comprises a CDR1 comprising the amino acid sequence set forth in SEQ ID NO: 11, a CDR2 comprising the amino acid sequence set forth in SEQ ID NO: 20, and a CDR3 comprising the amino acid sequence set forth in SEQ ID NO: 21. SEQ ID NOs: 20 and 21 are provided below.

```
                                   [SEQ ID NO: 20]
        GASRRAT

[SEQ ID: 21]
        QQAGIPPYT
```

In certain embodiments, the V$_L$ comprises an amino acid sequence that is at least about 80% (e.g., at least about 85%, at least about 90%, or at least about 95%) identical or homologous to the amino acid sequence set forth in SEQ ID NO: 22. For example, the V$_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 22. In certain embodiments, the V$_L$ comprises the amino acid sequence set forth in SEQ ID NO: 22. SEQ ID NO: 22 is provided below.

```
                                   [SEQ ID NO: 22]
EIVLTQSPGTLSLSPGERATLSCRASQSVSSSYLAWYQQKPGQAPRLLI

YGASRRATGIPDRFSGSGSGTDFTLTISRLEPEDFAVYYCQQAGIPPYT

FGGGTKVEIK
```

In certain embodiments, the V$_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and the V$_L$ comprises a CDR1 comprising the amino acid sequence set forth in SEQ ID NO: 11 or a conservative modification thereof, a CDR2 comprising the amino acid sequence set forth in SEQ ID NO: 20 or a conservative modification, and a CDR3 comprising the amino acid sequence set forth in SEQ ID NO: 21 or a conservative modification thereof. In certain embodiments, the V$_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the V$_L$ comprises a CDR1 comprising the amino acid sequence set forth in SEQ ID NO: 11, a CDR2 comprising the amino acid sequence set forth in SEQ ID NO: 20, and a CDR3 comprising the amino acid sequence set forth in SEQ ID NO: 21.

In certain embodiments, the V$_H$ comprises the amino acid sequence set forth in SEQ ID NO: 10, and the V$_L$ comprises the amino acid sequence set forth in SEQ ID NO: 22.

In certain embodiments, the V$_L$ is positioned at the N-terminus of the extracellular antigen-binding domain, i.e., the V$_H$ the V$_L$ are positioned from the N- to the C-terminus as V$_L$-V$_H$. In certain embodiments, the extracellular antigen-binding domain of the CAR is a scFv that comprises a V$_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; a V$_L$ comprising a CDR1 comprising the amino acid sequence set forth in SEQ ID NO: 11, a CDR2 comprising the amino acid sequence set forth in SEQ ID NO: 20, and a CDR3 comprising the amino acid sequence set forth in SEQ ID NO: 21. In certain embodiments, the scFv comprises a V$_H$ comprising the amino acid sequence set forth in SEQ ID NO: 10, and a V$_L$ comprising the amino acid sequence set forth in SEQ ID NO: 22. In certain embodiments, the scFv comprises or consists of the amino acid sequence set forth in SEQ ID NO: 23. SEQ ID NO: 23 is provided below. In certain embodiments, the anti-CD19 scFv is designated as "#15 scFv".

```
                                          [SEQ ID NO: 23]
QVQLVESGGGVVQPGRSLRLSCAASGFTFSSYGMHWVRQAPGKGLEWVA

LIWYDGSNKYYADSVKGRFTISRDNSKNTLYLQMNSLRAEDTAVYYCAK

PVEGLLRGFDYWGQGTLVTVSSGGGGSGGGGSGGGGSEIVLTQSPGTLS

LSPGERATLSCRASQSVSSSYLAWYQQKPGQAPRLLIYGASRRATGIPD

RFSGSGSGTDFTLTISRLEPEDFAVYYCQQAGIPPYTFGGGTKVEIK
```

In certain embodiments, the CDRs are identified according to the Kabat numbering system.

In certain embodiments, the V$_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 57 or a conservative modification thereof. In certain embodiments, the V$_L$ comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 57. SEQ ID NO: 57 is provided below.

```
                                          [SEQ ID NO: 57]
        QQVDSLHPFT
```

In certain embodiments, the V$_L$ comprises an amino acid sequence that is at least about 80% (e.g., at least about 85%, at least about 90%, or at least about 95%) identical or homologous to the amino acid sequence set forth in SEQ ID NO: 58. For example, the V$_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 58. In certain embodiments, the V$_L$ comprises the amino acid sequence set forth in SEQ ID NO: 58. SEQ ID NO: 58 is provided below.

```
                                          [SEQ ID NO: 58]
EIVLTQSPGTLSLSPGERATLSCRASQSVSSSYLAWYQQKPGQAPRLLI

YGASSRATGIPDRFSGSGSGTDFTLTISRLEPEDFAVYYCQQVDSLHPF

TFGGGTKVEIK
```

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and the $V_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification, and a CDR3 comprising the amino acid sequence set forth in SEQ ID NO: 57 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the $V_L$ comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 57.

In certain embodiments, the $V_H$ comprises the amino acid sequence set forth in SEQ ID NO: 10, and the $V_L$ comprises the amino acid sequence set forth in SEQ ID NO: 58.

In certain embodiments, the $V_L$ is positioned at the N-terminus of the extracellular antigen-binding domain, i.e., the $V_H$ the $V_L$ are positioned from the N- to the C-terminus as $V_L$-$V_H$. In certain embodiments, the extracellular antigen-binding domain of the CAR is a scFv that comprises a $V_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; a $V_L$ comprising a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 57. In certain embodiments, the scFv comprises a $V_H$ comprising the amino acid sequence set forth in SEQ ID NO: 10, and a $V_L$ comprising the amino acid sequence set forth in SEQ ID NO: 58. In certain embodiments, the anti-CD19 scFv is designated as "#4 scFv".

In certain embodiments, the CDRs are identified according to the Kabat numbering system.

In certain embodiments, the $V_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 59 or a conservative modification thereof. In certain embodiments, the $V_L$ comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 59. SEQ ID NO: 59 is provided below.

[SEQ ID NO: 59]
QQAGGVPPLT

In certain embodiments, the $V_L$ comprises an amino acid sequence that is at least about 80% (e.g., at least about 85%, at least about 90%, or at least about 95%) identical or homologous to the amino acid sequence set forth in SEQ ID NO: 60. For example, the $V_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 60. In certain embodiments, the $V_L$ comprises the amino acid sequence set forth in SEQ ID NO: 60. SEQ ID NO: 60 is provided below.

[SEQ ID NO: 60]
EIVLTQSPGTLSLSPGERATLSCRASQSVSSSYLAWYQQKPGQAPRLLI

YGASSRATGIPDRFSGSGSGTDFTLTISRLEPEDFAVYYCQQAGGVPPL

TFGGGTKVEIK

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and the $V_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification, and a CDR3 comprising the amino acid sequence set forth in SEQ ID NO: 59 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the $V_L$ comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 59.

In certain embodiments, the $V_H$ comprises the amino acid sequence set forth in SEQ ID NO: 10, and the $V_L$ comprises the amino acid sequence set forth in SEQ ID NO: 60.

In certain embodiments, the $V_L$ is positioned at the N-terminus of the extracellular antigen-binding domain, i.e., the $V_H$ the $V_L$ are positioned from the N- to the C-terminus as $V_L$-$V_H$. In certain embodiments, the extracellular antigen-binding domain of the CAR is a scFv that comprises a $V_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; a $V_L$ comprising a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 59. In certain embodiments, the scFv comprises a $V_H$ comprising the amino acid sequence set forth in SEQ ID NO: 10, and a $V_L$ comprising the amino acid sequence set forth in SEQ ID NO: 60. In certain embodiments, the anti-CD19 scFv is designated as "#5 scFv".

In certain embodiments, the CDRs are identified according to the Kabat numbering system.

In certain embodiments, the $V_L$ comprises a CDR1 comprising the amino acid sequence set forth in SEQ ID NO: 16 or a conservative modification thereof, a CDR2 comprising the amino acid sequence set forth in SEQ ID NO: 12 or a conservative modification thereof, and a CDR3 comprising the amino acid sequence set forth in SEQ ID NO: 61 or a conservative modification thereof. In certain embodiments, the $V_L$ comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 61. SEQ ID NO: 61 is provided below.

[SEQ ID NO: 61]

QQAGVPPLT

In certain embodiments, the $V_L$ comprises an amino acid sequence that is at least about 80% (e.g., at least about 85%, at least about 90%, or at least about 95%) identical or homologous to the amino acid sequence set forth in SEQ ID NO: 62. For example, the $V_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 62. In certain embodiments, the $V_L$ comprises the amino acid sequence set forth in SEQ ID NO: 62. SEQ ID NO: 62 is provided below.

[SEQ ID NO: 62]

EIVLTQSPGTLSLSPGERATLSCRASQSVRSSYLAWYQQKPGQAPRLLI

YGASSRATGIPDRFSGSGSGTDFTLTISRLEPEDFAVYYCQQAGVPPLT

FGGGTKVEIK

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and the $V_L$ comprises a CDR1 comprising the amino acid sequence set forth in SEQ ID NO: 16 or a conservative modification thereof, a CDR2 comprising the amino acid sequence set forth in SEQ ID NO: 12 or a conservative modification, and a CDR3 comprising the amino acid sequence set forth in SEQ ID NO: 61 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the $V_L$ comprises a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 61.

In certain embodiments, the $V_H$ comprises the amino acid sequence set forth in SEQ ID NO: 10, and the $V_L$ comprises the amino acid sequence set forth in SEQ ID NO: 62.

In certain embodiments, the $V_L$ is positioned at the N-terminus of the extracellular antigen-binding domain, i.e., the $V_H$ the $V_L$ are positioned from the N- to the C-terminus as $V_L$-$V_H$. In certain embodiments, the extracellular antigen-binding domain of the CAR is a scFv that comprises a $V_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; a $V_L$ comprising a CDR1 comprising the amino acid sequence set forth in SEQ ID NO: 16, a CDR2 comprising the amino acid sequence set forth in SEQ ID NO: 12, and a CDR3 comprising the amino acid sequence set forth in SEQ ID NO: 61. In certain embodiments, the scFv comprises a $V_H$ comprising the amino acid sequence set forth in SEQ ID NO: 10, and a $V_L$ comprising the amino acid sequence set forth in SEQ ID NO: 62. In certain embodiments, the anti-CD19 scFv is designated as "#6 scFv".

In certain embodiments, the CDRs are identified according to the Kabat numbering system.

In certain embodiments, the $V_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification thereof, and a CDR3 comprising the amino acid sequence set forth in SEQ ID NO: 63 or a conservative modification thereof. In certain embodiments, the $V_L$ comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 63. SEQ ID NO: 63 is provided below.

[SEQ ID NO: 63]

QQAGGVPPFT

In certain embodiments, the $V_L$ comprises an amino acid sequence that is at least about 80% (e.g., at least about 85%, at least about 90%, or at least about 95%) identical or homologous to the amino acid sequence set forth in SEQ ID NO: 64. For example, the $V_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 64. In certain embodiments, the $V_L$ comprises the amino acid sequence set forth in SEQ ID NO: 64. SEQ ID NO: 64 is provided below.

[SEQ ID NO: 64]

EIVMTQSPGTLSLSPGERATLSCRASQSVSSSYLAWYQQKPGQAPRLLI

YGASSRATGIPDRFSGSGSGTDFTLTISRLEPEDFAVYYCQQAGGVPPF

TFGGGTKVEIK

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and the $V_L$ comprises a CDR1 comprising the amino acid sequence set forth in SEQ ID NO: 11 or a conservative modification thereof, a CDR2 comprising the amino acid sequence set forth in SEQ ID NO: 12 or a conservative modification, and a CDR3 comprising the amino acid sequence set forth in SEQ ID NO: 63 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the $V_L$ comprises a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 63.

In certain embodiments, the $V_H$ comprises the amino acid sequence set forth in SEQ ID NO: 10, and the $V_L$ comprises the amino acid sequence set forth in SEQ ID NO: 64.

In certain embodiments, the $V_L$ is positioned at the N-terminus of the extracellular antigen-binding domain, i.e., the $V_H$ the $V_L$ are positioned from the N- to the C-terminus as $V_L$-$V_H$. In certain embodiments, the extracellular antigen-binding domain of the CAR is a scFv that comprises a $V_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; a $V_L$ comprising a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 63. In certain embodiments, the scFv comprises a $V_H$ comprising the amino acid sequence set forth in SEQ ID NO: 10, and a $V_L$ comprising the amino acid sequence set forth in SEQ ID NO: 64. In certain embodiments, the anti-CD19 scFv is designated as "#7 scFv".

In certain embodiments, the CDRs are identified according to the Kabat numbering system.

In certain embodiments, the $V_L$ comprises a CDR1 comprising the amino acid sequence set forth in SEQ ID NO: 11 or a conservative modification thereof, a CDR2 comprising the amino acid sequence set forth in SEQ ID NO: 65 or a conservative modification thereof, and a CDR3 comprising the amino acid sequence set forth in SEQ ID NO: 66 or a conservative modification thereof. In certain embodiments, the $V_L$ comprises a CDR1 comprising the amino acid sequence set forth in SEQ ID NO: 11, a CDR2 comprising the amino acid sequence set forth in SEQ ID NO: 65, and a CDR3 comprising the amino acid sequence set forth in SEQ ID NO: 66. SEQ ID NOS: 66 and 67 are provided below.

```
                                        [SEQ ID NO: 65]
        GASNRAT

[SEQ ID NO: 66]
        QQAGVFPFT
```

In certain embodiments, the $V_L$ comprises an amino acid sequence that is at least about 80% (e.g., at least about 85%, at least about 90%, or at least about 95%) identical or homologous to the amino acid sequence set forth in SEQ ID NO: 67. For example, the $V_L$ comprises an amino acid sequence that is about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% identical or homologous to the amino acid sequence set forth in SEQ ID NO: 67. In certain embodiments, the $V_L$ comprises the amino acid sequence set forth in SEQ ID NO: 67. SEQ ID NO: 67 is provided below.

```
                                        [SEQ ID NO: 67]
EIVMTQSPGTLSLSPGERATLSCRASQSVSSSYLAWYQQKPGQAPRLLI

YGASNRATGIPDRFSGSGSGTDFTLTISRLEPEDFAVYYCQQAGVFPFT

FGGGTKVEIK
```

In certain embodiments, the $V_H$ comprises a CDR1 comprising the amino acid sequence set forth in SEQ ID NO: 7 or a conservative modification thereof, a CDR2 comprising the amino acid sequence set forth in SEQ ID NO: 8 or a conservative modification thereof, and a CDR3 comprising the amino acid sequence set forth in SEQ ID NO: 9 or a conservative modification thereof; and the $V_L$ comprises a CDR1 comprising the amino acid sequence set forth in SEQ ID NO: 11 or a conservative modification thereof, a CDR2 comprising the amino acid sequence set forth in SEQ ID NO: 65 or a conservative modification, and a CDR3 comprising the amino acid sequence set forth in SEQ ID NO: 66 or a conservative modification thereof. In certain embodiments, the $V_H$ comprises a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and the $V_L$ comprises a CDR1 comprising the amino acid sequence set forth in SEQ ID NO: 11, a CDR2 comprising the amino acid sequence set forth in SEQ ID NO: 65, and a CDR3 comprising the amino acid sequence set forth in SEQ ID NO: 66.

In certain embodiments, the $V_H$ comprises the amino acid sequence set forth in SEQ ID NO: 10, and the $V_L$ comprises the amino acid sequence set forth in SEQ ID NO: 67.

In certain embodiments, the $V_L$ is positioned at the N-terminus of the extracellular antigen-binding domain, i.e., the $V_H$ the $V_L$ are positioned from the N- to the C-terminus as $V_L$-$V_H$. In certain embodiments, the extracellular antigen-binding domain of the CAR is a scFv that comprises a $V_H$ comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; a $V_L$ comprising a CDR1 comprising the amino acid sequence set forth in SEQ ID NO: 11, a CDR2 comprising the amino acid sequence set forth in SEQ ID NO: 65, and a CDR3 comprising the amino acid sequence set forth in SEQ ID NO: 66. In certain embodiments, the scFv comprises a $V_H$ comprising the amino acid sequence set forth in SEQ ID NO: 10, and a $V_L$ comprising the amino acid sequence set forth in SEQ ID NO: 67. In certain embodiments, the anti-CD19 scFv is designated as "#1 scFv".

In certain embodiments, the CDRs are identified according to the Kabat numbering system.

An exemplary nucleotide sequence encoding the amino acid sequence of SEQ ID NO: 10 is set forth in SEQ ID NO: 68. SEQ ID NO: 68 is provided below.

```
                                        [SEQ ID NO: 68]
CAGGTGCAGCTGGTGGAGTCTGGGGGAGGCGTGGTCCAGCCTGGGAGGT

CCCTGAGACTCTCCTGTGCAGCGTCTGGATTCACCTTCAGTAGCTATGG

CATGCACTGGGTCCGCCAGGCTCCAGGCAAGGGGCTGGAGTGGGTGGCA

CTGATATGGTATGATGGAAGTAATAAATACTATGCAGACTCCGTGAAGG

GCCGATTCACCATCTCCAGAGACAATTCCAAGAACACGCTGTATCTGCA
```

-continued

AATGAACAGCCTGAGAGCCGAGGACACGGCGGTGTACTACTGCGCCAAG

CCAGTGGAAGGACTATTAAGAGGATTCGATTACTGGGGACAGGGTACAT

TGGTCACCGTCTCCTCA

An exemplary nucleotide sequence encoding the amino acid sequence of SEQ ID NO: 14 is set forth in SEQ ID NO: 69. SEQ ID NO: 69 is provided below.

[SEQ ID NO: 69]
GAAATTGTGTTGACGCAGTCTCCAGGCACCCTGTCTTTGTCTCCAGGGG

AAAGAGCCACCCTCTCCTGCAGGGCCAGTCAGAGTGTTAGCAGCAGCTA

CTTAGCCTGGTACCAGCAGAAACCTGGCCAGGCTCCCAGGCTCCTCATC

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGGCCGGAGCCGTCCCTATCACT

TTTGGCGGAGGGACCAAGGTTGAGATCAAA

An exemplary nucleotide sequence encoding the amino acid sequence of SEQ ID NO: 18 is set forth in SEQ ID NO: 70. SEQ ID NO: 70 is provided below.

[SEQ ID NO: 70]
GAAATTGTGTTGACGCAGTCTCCAGGCACCCTGTCTTTGTCTCCAGGGG

AAAGAGCCACCCTCTCCTGCAGGGCCAGTCAGAGTGTTAGGAGCAGCTA

CTTAGCCTGGTACCAGCAGAAACCTGGCCAGGCTCCCAGGCTCCTCATC

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGCTCTTCGACAGTCCTTACACT

TTTGGCGGAGGGACCAAGGTTGAGATCAAA

An exemplary nucleotide sequence encoding the amino acid sequence of SEQ ID NO: 22 is set forth in SEQ ID NO: 71. SEQ ID NO: 71 is provided below.

[SEQ ID NO: 71]
GAAATTGTGTTGACGCAGTCTCCAGGCACCCTGTCTTTGTCTCCAGGGG

AAAGAGCCACCCTCTCCTGCAGGGCCAGTCAGAGTGTTAGCAGCAGCTA

CTTAGCCTGGTACCAGCAGAAACCTGGCCAGGCTCCCAGGCTCCTCATC

TATGGTGCATCCAGAAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGGCCGGCATCCCCCCTTACACT

TTTGGCGGAGGGACCAAGGTTGAGATCAAA

An exemplary nucleotide sequence encoding the amino acid sequence of SEQ ID NO: 58 is set forth in SEQ ID NO: 72. SEQ ID NO: 72 is provided below.

[SEQ ID NO: 72]
GAAATTGTGTTGACGCAGTCTCCAGGCACCCTGTCTTTGTCTCCAGGGG

AAAGAGCCACCCTCTCCTGCAGGGCCAGTCAGAGTGTTAGCAGCAGCTA

CTTAGCCTGGTACCAGCAGAAACCTGGCCAGGCTCCCAGGCTCCTCATC

-continued

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGGTCGACAGTCTCCATCCTTTC

ACTTTTGGCGGAGGGACCAAGGTTGAGATCAAA

An exemplary nucleotide sequence encoding the amino acid sequence of SEQ ID NO: 60 is set forth in SEQ ID NO: 73. SEQ ID NO: 73 is provided below.

[SEQ ID NO: 73]
GAAATTGTGTTGACGCAGTCTCCAGGCACCCTGTCTTTGTCTCCAGGGG

AAAGAGCCACCCTCTCCTGCAGGGCCAGTCAGAGTGTTAGCAGCAGCTA

CTTAGCCTGGTACCAGCAGAAACCTGGCCAGGCTCCCAGGCTCCTCATC

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGGCCGGAGGCGTCCCTCCTCTC

ACTTTTGGCGGAGGGACCAAGGTTGAGATCAAA

An exemplary nucleotide sequence encoding the amino acid sequence of SEQ ID NO: 62 is set forth in SEQ ID NO: 74. SEQ ID NO: 74 is provided below.

[SEQ ID NO: 74]
GAAATTGTGTTGACGCAGTCTCCAGGCACCCTGTCTTTGTCTCCAGGGG

AAAGAGCCACCCTCTCCTGCAGGGCCAGTCAGAGTGTTAGGAGCAGCTA

CTTAGCCTGGTACCAGCAGAAACCTGGCCAGGCTCCCAGGCTCCTCATC

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGGCCGGAGTCCCCCCTCTCACT

TTTGGCGGAGGGACCAAGGTTGAGATCAAA

An exemplary nucleotide sequence encoding the amino acid sequence of SEQ ID NO: 64 is set forth in SEQ ID NO: 75. SEQ ID NO: 75 is provided below.

[SEQ ID NO: 75]
GAAATTGTGATGACGCAGTCTCCAGGCACCCTGTCTTTGTCTCCAGGGG

AAAGAGCCACCCTCTCCTGCAGGGCCAGTCAGAGTGTTAGCAGCAGCTA

CTTAGCCTGGTACCAGCAGAAACCTGGCCAGGCTCCCAGGCTCCTCATC

TATGGTGCATCCAGCAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGGCCGGAGGCGTCCCTCCTTTC

ACTTTTGGCGGAGGGACCAAGGTTGAGATCAAA

An exemplary nucleotide sequence encoding the amino acid sequence of SEQ ID NO: 67 is set forth in SEQ ID NO: 76. SEQ ID NO: 76 is provided below.

```
                                        [SEQ ID NO: 76]
GAAATTGTGATGACGCAGTCTCCAGGCACCCTGTCTTTGTCTCCAGGGG

AAAGAGCCACCCTCTCCTGCAGGGCCAGTCAGAGTGTTAGCAGCAGCTA

CTTAGCCTGGTACCAGCAGAAACCTGGCCAGGCTCCCAGGCTCCTCATC

TATGGTGCATCCAACAGGGCCACTGGCATCCCAGACAGGTTCAGTGGCA

GTGGGTCTGGGACAGACTTCACTCTCACCATCAGCAGACTGGAGCCTGA

AGATTTTGCAGTGTATTACTGTCAGCAGGCCGGAGTCTTCCCTTTCACT

TTTGGCGGAGGGACCAAGGTTGAGATCAAA
```

In certain embodiments, the $V_H$ and $V_L$ are linked via a linker. In certain embodiments, the linker comprises or consists of the amino acid sequence set forth in SEQ ID NO: 1, SEQ ID NO: 2, SEQ ID NO: 3, or SEQ ID NO: 4. In certain embodiments, the linker comprises or consists of the amino acid sequence set forth in SEQ ID NO: 1.

The $V_H$ and/or $V_L$ amino acid sequences consisting of at least about 80%, at least about 80%, at least about 85%, at least about 90%, or at least about 95% (e.g., about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99%) homology or identity to a specific sequence (e.g., SEQ ID NO: 10, SEQ ID NO: 14, SEQ ID NO: 18, SEQ ID NO: 22, SEQ ID NO: 58, SEQ ID NO: 60, SEQ ID NO: 62, SEQ ID NO: 64, or SEQ ID NO: 67) may contain substitutions (e.g., conservative substitutions), insertions, or deletions relative to the specified sequence(s), but retain the ability to bind to a target antigen (e.g., mesothelin). In certain embodiments, a total of 1 to 10 amino acids are substituted, inserted and/or deleted in a specific sequence (e.g., SEQ ID NO: 10, SEQ ID NO: 14, SEQ ID NO: 18, SEQ ID NO: 22, SEQ ID NO: 58, SEQ ID NO: 60, SEQ ID NO: 62, SEQ ID NO: 64, or SEQ ID NO: 67). In certain embodiments, substitutions, insertions, or deletions occur in regions outside the CDRs (e.g., in the FRs) of the extracellular antigen-binding domain. In certain embodiments, the extracellular antigen-binding domain comprises $V_H$ and/or $V_L$ sequence selected from SEQ ID NOs: 10, 14, 18, 22, 59, 61, 63, 65, and 68, including post-translational modifications of SEQ ID NO: 10, SEQ ID NO: 14, SEQ ID NO: 18, SEQ ID NO: 22, SEQ ID NO: 58, SEQ ID NO: 60, SEQ ID NO: 62, SEQ ID NO: 64, or SEQ ID NO: 67.

In addition, the extracellular antigen-binding domain can comprise a leader or a signal peptide that directs the nascent protein into the endoplasmic reticulum. Signal peptide or leader can be essential if the CAR is to be glycosylated and anchored in the cell membrane. The signal sequence or leader can be a peptide sequence (about 5, about 10, about 15, about 20, about 25, or about 30 amino acids long) present at the N-terminus of newly synthesized proteins that directs their entry to the secretory pathway. In certain embodiments, the signal peptide is covalently joined to the 5' terminus (N-terminus) of the extracellular antigen-binding domain. In certain embodiments, the signal peptide comprises a CD8 polypeptide, e.g., the CAR comprises a truncated CD8 signal peptide. In certain embodiments, the signal peptide is generated from the antibody from it is derived. In certain embodiments, the signal peptide for #2 scFv is set forth in SEQ ID NO: 54. In certain embodiments, the signal peptide for #8 scFv is set forth in SEQ ID NO: 54. In certain embodiments, the signal peptide for #15 scFv is set forth in SEQ ID NO: 55.

```
                                        [SEQ ID NO: 54]
          MDMRVPAQLLGLLLLWLPDTRC

[SEQ ID NO: 55]
          MEFGLSWVFLVALLRGVQC
```

5.3.2. Transmembrane Domain of a CAR

In certain embodiments, the transmembrane domain of the CAR comprises a hydrophobic alpha helix that spans at least a portion of the membrane. Different transmembrane domains result in different receptor stability. After antigen recognition, receptors cluster and a signal are transmitted to the cell. In certain embodiments, the transmembrane domain of the CAR comprises a native or modified transmembrane domain of CD8, of CD28, of CD3ζ, of CD4, of 4-1BB, of OX40, of ICOS, of CD84, of CD166, of CD8a, of CD8b, of ICAM-1, of CTLA-4, of CD27, of CD40, of NKGD2, or a combination thereof.

In certain embodiments, the transmembrane domain of the CAR comprises a CD28 polypeptide (e.g., a transmembrane domain of CD28 or a portion thereof). In certain embodiments, the transmembrane domain of the CAR comprises a transmembrane domain of human CD28 or a portion thereof. The CD28 polypeptide can comprise or consist of an amino acid sequence that is at least about 85%, about 90%, about 95%, about 96%, about 97%, about 98%, about 99% or 100% identical or homologous to the sequence having a NCBI Reference No: NP_006130 (SEQ ID NO: 24), or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 24, which is at least about 20, or at least about 30, or at least about 40, or at least about 50, or at least about 60, and/or up to about 70, up to about 80, up to about 90, up to about 100, up to about 150, up to about 200, or up to about 220 amino acids in length. In certain embodiments, the CD28 polypeptide comprises or consists of the amino acid sequence of amino acids 1 to 220, 1 to 50, 50 to 100, 100 to 150, 154 to 179, 150 to 200, 153 to 179, or 200 to 220 of SEQ ID NO: 24. In certain embodiments, the transmembrane domain of the CAR comprises a CD28 polypeptide comprising or consisting of the amino acid sequence of amino acids 154 to 179 of SEQ ID NO: 24. SEQ ID NO: 24 is provided below.

```
                                        [SEQ ID NO: 24]
    MLRLLLALNL FPSIQVTGNK ILVKQSPMLV AYDNAVNLSC

KYSYNLFSRE FRASLHKGLD SAVEVCVVYG NYSQQLQVYS

KTGFNCDGKL GNESVTFYLQ NLYVNQTDIY FCKIEVMYPP

PYLDNEKSNG TIIHVKGKHL CPSPLFPGPS KPFWVLVVVG

GVLACYSLLV TVAFIIFWVR SKRSRLLHSD YMNMTPRRPG

PTRKHYQPYA PPRDFAAYRS
```

An exemplary nucleotide sequence encoding the amino acid sequence of amino acids 154 to 179 of SEQ ID NO: 24 is set forth in SEQ ID NO: 25, which is provided below.

[SEQ ID NO: 25]

TGGGTGCTGGTGGTGGTTGGTGGAGTCCTGGCTTGCTATAGCTTGCTAG

TAACAGTGGCCTTTATTATTTTCTGGGTG

In certain embodiments, the transmembrane domain of the CAR comprises a transmembrane domain of mouse CD28 or a portion thereof. The CD28 polypeptide can consist of an amino acid sequence that is at least about 85%, about 90%, about 95%, about 96%, about 97%, about 98%, about 99% or 100% identical or homologous to the sequence having a NCBI Reference No: NP_031668.3 (SEQ ID No: 26), or a fragment thereof, and/or may optionally comprise up to one or up to two or up to three conservative amino acid substitutions. In certain embodiments, the CD28 polypeptide comprises or consists of an amino acid sequence that is a consecutive portion of SEQ ID NO: 26, which is at least about 20, or at least about 30, or at least about 40, or at least about 50, and up to about 218 amino acids in length. In certain embodiments, the CD28 polypeptide comprises or consists of an amino acid sequence of amino acids 1 to 218, 1 to 50, 50 to 100, 100 to 150, 150 to 200, 151 to 177, or 200 to 218 of SEQ ID NO: 26. In certain embodiments, the transmembrane domain of the CAR comprises a CD28 polypeptide comprising or consisting of the amino acid sequence of amino acids 151 to 177 of SEQ ID NO: 26. SEQ ID NO: 26 is provided below:

[SEQ ID NO: 26]

```
MTLRLLFLAL NFFSVQVTEN KILVKQSPLL VVDSNEVSLS

CRYSYNLLAK EFRASLYKGV NSDVEVCVGN GNFTYQPQFR

SNAEFNCDGD FDNETVTFRL WNLHVNHTDI YFCKIEFMYP

PPYLDNERSN GTIIHIKEKH LCHTQSSPKL FWALVVVAGV

LFCYGLLVTV ALCVIWTNSR RNRLLQSDYM NMTPRRPGLT

RKPYQPYAPA RDFAAYRP
```

In certain embodiments, the transmembrane domain of the CAR comprises a CD8 polypeptide (e.g., a transmembrane domain of CD8 or a portion thereof). In certain embodiments, the transmembrane domain of the CAR comprises a transmembrane domain of human CD8 or a portion thereof. In certain embodiments, the CD8 polypeptide comprises or has an amino acid sequence that is at least about 85%, about 90%, about 95%, about 96%, about 97%, about 98%, about 99% or about 100% identical or homologous to the sequence having a NCBI Reference No: NP_001139345.1 (SEQ ID NO: 27) or a fragment thereof, and/or may optionally comprise up to one or up to two or up to three conservative amino acid substitutions. In certain embodiments, the CD8 polypeptide comprises or consists of an amino acid sequence that is a consecutive portion of SEQ ID NO: 27, which is at least about 20, or at least about 30, or at least about 40, or at least about 50, and up to about 235 amino acids in length. Alternatively or additionally, in certain embodiments, the CD8 polypeptide comprises or consists of an amino acid sequence of amino acids 1 to 235, 1 to 50, 50 to 100, 100 to 150, 150 to 200, 137 to 209 or 200 to 235 of SEQ ID NO: 27. In certain embodiments, the transmembrane domain of the CAR comprises a CD8 polypeptide comprising or consisting of the amino acid sequence of amino acids 137 to 209 of SEQ ID NO: 27. SEQ ID NO: 27 is provided below.

[SEQ ID NO: 27]

MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGYYFCSALSNSIMYFSHFVPVFLPAKPTTTPAPRPPT

PAPTIASQPLSLRPEACRPAAGGAVHTRGLDFACDIYIWAPLAGTCGVL

LLSLVITLYCNHRNRRRVCKCPRPVVKSGDKPSLSARYV

In certain embodiments, the transmembrane domain of the CAR comprises a transmembrane domain of mouse CD8 or a portion thereof. In certain embodiments, the CD8 polypeptide comprises or has an amino acid sequence that is at least about 85%, about 90%, about 95%, about 96%, about 97%, about 98%, about 99% or about 100% identical or homologous to the sequence having a NCBI Reference No: AAA92533.1 (SEQ ID NO: 28) or a fragment thereof, and/or may optionally comprise up to one or up to two or up to three conservative amino acid substitutions. In certain embodiments, the CD8 polypeptide comprises or has an amino acid sequence that is a consecutive portion of SEQ ID NO: 28, which is at least about 20, or at least about 30, or at least about 40, or at least about 50, or at least about 60, or at least about 70, or at least about 100, or at least about 200, and up to 247 amino acids in length. Alternatively or additionally, in certain embodiments, the CD8 polypeptide comprises or consists of an amino acid sequence of amino acids 1 to 247, 1 to 50, 50 to 100, 100 to 150, 150 to 200, 151 to 219, or 200 to 247 of SEQ ID NO: 28. In certain embodiments, the transmembrane domain of the CAR comprises a CD8 polypeptide comprising or consisting of the amino acid sequence of amino acids 151 to 219 of SEQ ID NO: 28. SEQ ID NO: 28 is provided below.

[SEQ ID NO: 28]

```
MASPLTRFLS LNLLLMGESI ILGSGEAKPQ APELRIFPKK

MDAELGQKVD LVCEVLGSVS QGCSWLFQNS SSKLPQPTFV

VYMASSHNKI TWDEKLNSSK LFSAVRDTNN KYVLTLNKFS

KENEGYYFCS VISNSVMYFS SVVPVLQKVN STTTKPVLRT

PSPVHPTGTS QPQRPEDCRP RGSVKGTGLD FACDIYIWAP

LAGICVAPLL SLIITLICYH RSRKRVCKCP RPLVRQEGKP

RPSEKIV
```

In certain non-limiting embodiments, the CAR further comprise a spacer region that links the extracellular antigen-binding domain to the transmembrane domain. The spacer region can be flexible enough to allow the antigen binding domain to orient in different directions to facilitate antigen recognition while preserving the activating activity of the CAR.

In certain embodiments, the hinge/spacer region of the CAR comprises a native or modified hinge region of CD8, of CD28, of CD3, of CD40, of 4-1BB, of OX40, of CD84, of CD166, of CD8a, of CD8b, of ICOS, of ICAM-1, of CTLA-4, of CD27, of CD40, of NKGD2, or a combination thereof. The hinge/spacer region can be the hinge region from IgG1, or the CH2CH3 region of immunoglobulin and portions of CD3, a portion of a CD28 polypeptide (e.g., a portion of SEQ ID NO: 24 or SEQ ID NO: 26), a portion of a CD8 polypeptide (e.g., a portion of SEQ ID NO: 27 or SEQ ID NO: 28), a variation of any of the foregoing which is at least about 80%, at least about 85%, at least about 90%, at least about 95%, or at least about 100% identical or homologous thereto, or a synthetic spacer sequence.

In certain embodiments, the hinge domain of the CAR comprises a native or modified hinge region of CD28. In certain embodiments, the hinge domain of the CAR comprises a native hinge region of CD28. In certain embodiments, the hinge domain of the CAR comprises the amino acid sequence of amino acids 114 to 153 of SEQ ID NO: 24. An exemplary nucleotide sequence encoding the amino acid sequence of amino acids 114 to 153 of SEQ ID NO: 24 is set forth in SEQ ID NO: 56, which is provided below.

```
                                    [SEQ ID NO: 56]
ATTGAAGTTATGTATCCTCCTCCTTACCTAGACAATGAGAAGAGCAATG

GAACCATTATCCATGTGAAAGGGAAACACCTTTGTCCAAGTCCCCTATT

TCCCGGACCTTCTAAGCCCTTT
```

5.3.3. Intracellular Signaling Domain of a CAR

In certain embodiments, the CAR comprises an intracellular signaling domain. In certain embodiments, the intracellular signaling domain of the CAR comprises a CD3ζ polypeptide. CD3ζ can activate or stimulate a cell (e.g., a cell of the lymphoid lineage, e.g., a T-cell). Wild type ("native") CD3ζ comprises three functional immunoreceptor tyrosine-based activation motifs (ITAMs), three functional basic-rich stretch (BRS) regions (BRS1, BRS2 and BRS3). CD3ζ transmits an activation signal to the cell (e.g., a cell of the lymphoid lineage, e.g., a T-cell) after antigen is bound. The intracellular signaling domain of the CD3ζ-chain is the primary transmitter of signals from endogenous TCRs.

In certain embodiments, the intracellular signaling domain of the CAR comprises a native CD3ζ. In certain embodiments, the native CD3ζ comprises or consists of an amino acid sequence that is at least about 85%, about 90%, about 95%, about 96%, about 97%, about 98%, about 99% or about 100% identical or homologous to the amino acid sequence having a NCBI Reference No: NP_932170 (SEQ ID NO: 29), or a fragment thereof, and/or may optionally comprise up to one or up to two or up to three conservative amino acid substitutions. In certain embodiments, the CD3ζ polypeptide comprises or consists of an amino acid sequence that is a consecutive portion of SEQ ID NO: 29, which is at least about 20, or at least about 30, or at least about 40, or at least about 50, and up to about 164 amino acids in length. In certain embodiments, the native CD3ζ comprises or consists of the amino acid sequence of amino acids 1 to 164, 1 to 50, 50 to 100, 52 to 164, 100 to 150, or 150 to 164 of SEQ ID NO: 29. In certain embodiments, the intracellular signaling domain of the CAR comprises a native CD3ζ comprising or consisting of the amino acid sequence of amino acids 52 to 164 of SEQ ID NO: 29. SEQ ID NO: 29 is provided below:

```
                                    [SEQ ID NO: 29]
MKWKALFTAA ILQAQLPITE AQSFGLLDPK LCYLLDGILF

IYGVILTALF LRVKFSRSAD APAYQQGQNQ LYNELNLGRR
```

-continued
```
EEYDVLDKRR GRDPEMGGKP QRRKNPQEGL YNELQKDKMA

EAYSEIGMKG ERRRGKGHDG LYQGLSTATK DTYDALHMQA

LPPR
```

In certain embodiments, the native CD3ζ comprises or consists of an amino acid sequence that is at least about 85%, about 90%, about 95%, about 96%, about 97%, about 98%, about 99% or about 100% identical or homologous to the amino acid sequence set forth in SEQ ID NO: 30. SEQ ID NO: 30 is provided below:

```
                                    [SEQ ID NO: 30]
RVKFSRSADAPAYQQGQNQLYNELNLGRREEYDVLDKRRGRDPEMGGKP

RRKNPQEGLYNELQKDKMAEAYSEIGMKGERRRGKGHDGLYQGLSTATK

DTYDALHMQALPPR
```

In certain embodiments, the intracellular signaling domain of the CAR comprises a modified CD3ζ polypeptide. In certain embodiments, the modified CD3ζ polypeptide comprises one, two or three ITAMs. In certain embodiments, the modified CD3ζ polypeptide comprises a native ITAM1. In certain embodiments, the native ITAM1 comprises or consists of the amino acid sequence set forth in SEQ ID NO: 31.

```
                                    [SEQ ID NO: 31]
QNQLYNELNLGRREEYDVLDKR
```

An exemplary nucleic acid sequence encoding the amino acid sequence of SEQ ID NO: 31 is set forth in SEQ ID NO: 32, which is provided below.

```
                                    [SEQ ID NO: 32]
CAGAACCAGCTCTATAACGAGCTCAATCTAGGACGAAGAGAGGAGTACG

ATGTTTTGGACAAGAGA
```

In certain embodiments, the modified CD3ζ polypeptide comprises an ITAM1 variant comprising one or more loss-of-function mutations. In certain embodiments, the ITAM1 variant comprises or consists of two loss-of-function mutations. In certain embodiments, each of the one or more (e.g., two) loss of function mutations comprises a mutation of a tyrosine residue in ITAM1. In certain embodiments, the ITAM1 variant consists of two loss-of-function mutations. In certain embodiments, the ITAM1 variant comprises or consists of the amino acid sequence set forth in SEQ ID NO: 33, which is provided below.

```
                                    [SEQ ID NO: 33]
QNQLFNELNLGRREEFDVLDKR
```

An exemplary nucleic acid sequence encoding the amino acid sequence of SEQ ID NO: 33 is set forth in SEQ ID NO: 34, which is provided below.

```
                                    [SEQ ID NO: 34]
CAGAACCAGCTCTTTAACGAGCTCAATCTAGGACGAAGAGAGGAGTTCG

ATGTTTTGGACAAGAGA
```

In certain embodiments, the modified CD3ζ polypeptide comprises a native ITAM2. In certain embodiments, the native ITAM2 comprises or consists of the amino acid sequence set forth in SEQ ID NO: 35, which is provided below.

[SEQ ID NO: 35]
QEGLYNELQKDKMAEAYSEIGMK

An exemplary nucleic acid sequence encoding the amino acid sequence of SEQ ID NO: 35 is set forth in SEQ ID NO: 36, which is provided below.

[SEQ ID NO: 36]
CAGGAAGGCCTGTACAATGAACTGCAGAAAGATAAGATGGCGGAGGCCT

ACAGTGAGATTGGGATGAAA

In certain embodiments, the modified CD3ζ polypeptide comprises an ITAM2 variant. In certain embodiments, the ITAM2 variant comprises or consists of one or more loss-of-function mutations. In certain embodiments, the ITAM2 variant comprises or consists of two loss-of-function mutations. In certain embodiments, each of the one or more (e.g., two) the loss of function mutations comprises a mutation of a tyrosine residue in ITAM2. In certain embodiments, the ITAM1 variant consists of two loss-of-function mutations. In certain embodiments, the ITAM2 variant comprises or consists of the amino acid sequence set forth in SEQ ID NO: 37, which is provided below.

[SEQ ID NO: 37]
QEGLFNELQKDKMAEAFSEIGMK

An exemplary nucleic acid sequence encoding the amino acid sequence of SEQ ID NO: 37 is set forth in SEQ ID NO: 38, which is provided below.

[SEQ ID NO: 38]
CAGGAAGGCCTGTTCAATGAACTGCAGAAAGATAAGATGGCGGAGGCCT

TCAGTGAGATTGGGATGAAA

In certain embodiments, the modified CD3ζ polypeptide comprises a native ITAM3. In certain embodiments, the native ITAM3 comprises or consists of the amino acid sequence set forth in SEQ ID NO: 39, which is provided below.

[SEQ ID NO: 39]
HDGLYQGLSTATKDTYDALHMQ

An exemplary nucleic acid sequence encoding the amino acid sequence of SEQ ID NO: 39 is set forth in SEQ ID NO: 40, which is provided below.

[SEQ ID NO: 40]
CACGATGGCCTTTACCAGGGTCTCAGTACAGCCACCAAGGACACCTACG

ACGCCCTTCACATGCAG

In certain embodiments, the modified CD3ζ polypeptide comprises an ITAM3 variant. In certain embodiments, the ITAM3 variant comprises or consists of two loss-of-function mutations. In certain embodiments, each of the one or more (e.g., two) the loss of function mutations comprises a mutation of a tyrosine residue in ITAM3. In certain embodiments, the ITAM3 variant comprises or consists of two loss-of-function mutations. In certain embodiments, the ITAM3 variant comprises or consists of the amino acid sequence set forth in SEQ ID NO: 41, which is provided below.

[SEQ ID NO: 41]
HDGLFQGLSTATKDTFDALHMQ.

An exemplary nucleic acid sequence encoding the amino acid sequence of SEQ ID NO: 41 is set forth in SEQ ID NO: 42, which is provided below.

[SEQ ID NO: 42]
CACGATGGCCTTTTCCAGGGGCTCAGTACAGCCACCAAGGACACCTTCG

ACGCCCTTCACATGCAG

Various modified CD3ζ polypeptides and CARs comprising modified CD3ζ polypeptides are disclosed in International Patent Application Publication No. WO2019/133969, which is incorporated by reference hereby in its entirety.

In certain embodiments, the intracellular signaling domain of the CAR comprises a modified CD3ζ polypeptide comprising a native ITAM1, an ITAM2 variant comprising or consisting of one or more (e.g., two) loss-of-function mutations, and an ITAM3 variant comprising or consisting of one or more (e.g., two) loss-of-function mutations. In certain embodiments, the intracellular signaling domain of the CAR comprises a modified CD3ζ polypeptide comprising a native ITAM1, an ITAM2 variant consisting of two loss-of-function mutations, and an ITAM3 variant consisting of two loss-of-function mutations. In certain embodiments, the intracellular signaling domain of the CAR comprises a modified CD3ζ polypeptide comprising a native ITAM1 consisting of the amino acid sequence set forth in SEQ ID NO: 31, an ITAM2 variant consisting of the amino acid sequence set forth in SEQ ID NO: 37, and an ITAM3 variant consisting of the amino acid sequence set forth in SEQ ID NO: 41. In certain embodiments, the CAR is designated as "1XX". In certain embodiments, the modified CD3ζ polypeptide comprises or consists of the amino acid sequence set forth in SEQ ID NO: 43. SEQ ID NO: 43 is provided below:

[SEQ ID NO: 43]
RVKFSRSADA PAYQQGQNQL YNELNLGRRE EYDVLDKRRG

RDPEMGGKPR RKNPQEGLFN ELQKDKMAEA FSEIGMKGER

RRGKGHDGLF QGLSTATKDT FDALHMQALP PR

In certain embodiments, the intracellular signaling domain of the CAR comprises a modified CD3ζ polypeptide comprising or consisting of an amino acid sequence that is at least about 80%, at least about 85%, at least about 90%, at least about 95%, at least about 96%, at least about 97%, at least about 98%, or at least about 99%, at least about 100% identical to SEQ ID NO: 43 or a fragment thereof, and/or may optionally comprise up to one or up to two or up to three conservative amino acid substitutions.

An exemplary nucleic acid sequence encoding the amino acid sequence of SEQ ID NO: 43 is set forth in SEQ ID NO: 44, which is provided below.

[SEQ ID NO: 44]
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

-continued

TGTTTTGGACAAGAGACGTGGCCGGGACCCTGAGATGGGGGGAAAGCCG

AGAAGGAAGAACCCTCAGGAAGGCCTGTTCAATGAACTGCAGAAAGATA

AGATGGCGGAGGCCTTCAGTGAGATTGGGATGAAAGGCGAGCGCCGGAG

GGGCAAGGGGCACGATGGCCTTTTCCAGGGGCTCAGTACAGCCACCAAG

GACACCTTCGACGCCCTTCACATGCAGGCCCTGCCCCCTCGC

Another exemplary nucleic acid sequence encoding the amino acid sequence of SEQ ID NO: 43 is set forth in SEQ ID NO: 45, which is provided below.

[SEQ ID NO: 45]
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGGAAAGCCG

AGAAGGAAGAACCCTCAGGAAGGCCTGTTCAATGAACTGCAGAAAGATA

AGATGGCGGAGGCCTTCAGTGAGATTGGGATGAAAGGCGAGCGCCGGAG

GGGCAAGGGGCACGATGGCCTTTTCCAGGGTCTCAGTACAGCCACCAAG

GACACCTTCGACGCCCTTCACATGCAGGCCCTGCCCCCTCGC

In certain embodiments, the intracellular signaling domain of the CAR further comprises at least one co-stimulatory signaling region. In certain embodiments, the at least one co-stimulatory region comprises a co-stimulatory molecule or a portion thereof. In certain embodiments, the at least one co-stimulatory region comprises an intracellular domain of at least one co-stimulatory molecule or a portion thereof.

As used herein, a "co-stimulatory molecule" refers to a cell surface molecule other than antigen receptor or its ligand that can provide an efficient response of lymphocytes to an antigen. In certain embodiments, a co-stimulatory molecule can provide optimal lymphocyte activation. Non-limiting examples of co-stimulatory molecules include CD28, 4-1BB, OX40, ICOS, DAP-10, and combinations thereof. The co-stimulatory molecule can bind to a co-stimulatory ligand, which is a protein expressed on cell surface that upon binding to its receptor produces a co-stimulatory response, i.e., an intracellular response that effects the stimulation provided when an antigen-recognizing receptor (e.g., a chimeric antigen receptor (CAR)) binds to its target antigen. As one example, a 4-1BB ligand (i.e., 4-1BBL) may bind to 4-1BB for providing an intracellular signal that in combination with a CAR signal induces an effector cell function of the CAR+ T-cell. In certain embodiments, the at least one co-stimulatory signaling region comprises an intracellular signaling domain of CD28 or a portion thereof, an intracellular domain of 4-1BB or a portion thereof, an intracellular domain of OX40 or a portion thereof, an intracellular domain of ICOS or a portion thereof, or an intracellular domain of DAP-10 or a portion thereof.

In certain embodiments, the intracellular signaling domain of the CAR comprises a co-stimulatory signaling region that comprises a CD28 polypeptide, e.g., an intracellular domain of CD28 or a portion thereof. In certain embodiments, the intracellular signaling domain of the CAR comprises a co-stimulatory signaling region that comprises an intracellular domain of human CD28 or a portion thereof.

In certain embodiments, the CD28 polypeptide comprised in the co-stimulatory signaling region of the CAR comprise or consists of an amino acid sequence that is at least about 80%, at least about 85%, at least about 90%, at least about 95%, at least about 96%, at least about 97%, at least about 98%, or at least about 99%, at least about 100% identical or homologous to the amino acid sequence set forth in SEQ ID NO: 24, or a fragment thereof, and/or may optionally comprise up to one or up to two or up to three conservative amino acid substitutions. In certain embodiments, the CD28 polypeptide comprised in the co-stimulatory signaling region comprises or consist of an amino acid sequence that is a consecutive portion of SEQ ID NO: 24, which is at least about 20, or at least about 30, or at least about 40, or at least about 50, and up to about 220 amino acids in length. Alternatively or additionally, in certain embodiments, the CD28 polypeptide comprised in the co-stimulatory signaling region comprises or consists of amino acids 1 to 220, 1 to 50, 50 to 100, 100 to 150, 114 to 220, 150 to 200, 180 to 220, or 200 to 220 of SEQ ID NO: 24. In certain embodiments, the intracellular signaling domain of the CAR comprises a co-stimulatory signaling region that comprises a CD28 polypeptide comprising or consisting of the amino acid sequence of amino acids 180 to 220 of SEQ ID NO: 24.

An exemplary nucleic acid sequence encoding the amino acid sequence of amino acids 180 to 220 of SEQ ID NO: 24 is set forth in SEQ ID NO: 46, which is provided below.

[SEQ ID NO: 46]
AGGAGTAAGAGGAGCAGGCTCCTGCACAGTGACTACATGAACATGACTC

CCCGCCGCCCCGGGCCCACCCGCAAGCATTACCAGCCCTATGCCCCACC

ACGCGACTTCGCAGCCTATCGCTCC

In certain embodiments, the intracellular signaling domain of the CAR comprises a co-stimulatory signaling region that comprises an intracellular domain of mouse CD28 or a portion thereof. In certain embodiments, the CD28 polypeptide comprised in the co-stimulatory signaling region comprises or consists of an amino acid sequence that is at least about 80%, at least about 85%, at least about 90%, at least about 95%, at least about 96%, at least about 97%, at least about 98%, or at least about 99%, at least about 100% identical or homologous to the amino acid sequence set forth in SEQ ID NO: 26, or a fragment thereof, and/or may optionally comprise up to one or up to two or up to three conservative amino acid substitutions. In certain embodiments, the CD28 polypeptide comprised in the co-stimulatory signaling region comprises or consists of an amino acid sequence that is a consecutive portion of SEQ ID NO: 26, which is at least about 20, or at least about 30, or at least about 40, or at least about 50, and up to 218 amino acids in length. In certain embodiments, the CD28 polypeptide comprised in the co-stimulatory signaling region comprises or consists of the amino acid sequence of amino acids 1 to 218, 1 to 50, 50 to 100, 100 to 150, 150 to 218, 178 to 218, or 200 to 218 of SEQ ID NO: 26. In certain embodiments, the co-stimulatory signaling region of a presently disclosed CAR comprises a CD28 polypeptide that comprises or consists of the amino acid sequence of amino acids 178 to 218 of SEQ ID NO: 26.

In certain embodiments, the intracellular signaling domain of the CAR comprises a co-stimulatory signaling region that comprises a 4-1BB polypeptide, e.g., an intracellular domain of 4-1BB or a portion thereof. In certain embodiments, the co-stimulatory signaling region comprises an intracellular domain of human 4-1BB or a portion thereof. In certain embodiments, the 4-1BB comprised in the co-stimulatory signaling region comprises or consists of an amino acid sequence that is at least about 80%, at least about 85%, at least about 90%, at least about 95%, at least about 96%, at least about 97%, at least about 98%, or at least about 99%, at least about 100% identical or homologous to the sequence having a NCBI Ref. No.: NP_001552 (SEQ ID NO: 47) or a fragment thereof, and/or may optionally comprise up to one or up to two or up to three conservative amino acid substitutions. In certain embodiments, the 4-1BB comprised in the co-stimulatory signaling region comprises or consists of an amino acid sequence that is a consecutive portion of SEQ ID NO: 47, which is at least about 20, or at least about 30, or at least about 40, or at least about 50, and/or up to about 50, up to about 60, up to about 70, up to about 80, up to about 90, up to about 100, up to about 200, or up to about 255 amino acids in length. In certain embodiments, the 4-1BB polypeptide comprised in the co-stimulatory signaling region comprises or consists of the amino acid sequence of amino acids 1 to 255, 1 to 50, 50 to 100, 100 to 150, 150 to 200, or 200 to 255 of SEQ ID NO: 47. In certain embodiments, the co-stimulatory signaling region comprises a 4-1BB polypeptide comprising or consisting of the amino acid sequence of amino acids 214 to 255 of SEQ ID NO: 46. SEQ ID NO: 47 is provided below.

```
                                        [SEQ ID NO: 47]
MGNSCYNIVA  TLLLVLNFER  TRSLQDPCSN  CPAGTFCDNN

RNQICSPCPP  NSFSSAGGQR  TCDICRQCKG  VERTRKECSS

TSNAECDCTP  GFHCLGAGCS  MCEQDCKQGQ  ELTKKGCKDC

CFGTFNDQKR  GICRPWTNCS  LDGKSVLVNG  TKERDVVCGP

SPADLSPGAS  SVTPPAPARE  PGHSPQIISF  FLALTSTALL

FLLFFLTLRF  SVVKRGRKKL  LYIFKQPFMR  PVQTTQEEDG

CSCRFPEEEE  GGCEL
```

In certain embodiments, the intracellular signaling domain of the CAR comprises a co-stimulatory signaling region that comprises intracellular domains of two or more co-stimulatory molecules or portions thereof, e.g., an intracellular domain of CD28 or a portion thereof and an intracellular domain of 4-1BB or a portion thereof, or an intracellular domains of CD28 or a portion thereof and an intracellular domain of OX40 or a portion thereof.

5.3.4. Exemplified CARs

In certain embodiments, the CAR comprises (a) an extracellular antigen-binding domain comprising (i) a $V_H$ that comprises a CDR1 consisting of the amino acid sequence set forth in SEQ ID NO: 7, a CDR2 consisting of the amino acid sequence set forth in SEQ ID NO: 8, and a CDR3 consisting of the amino acid sequence set forth in SEQ ID NO: 9, and (ii) a $V_L$ that comprises a CDR1 consisting of the amino acid sequence set forth in SEQ ID NO: 11, a CDR2 consisting of the amino acid sequence set forth in SEQ ID NO: 12, and a CDR3 consisting of the amino acid sequence set forth in SEQ ID NO: 13, (b) a hinge domain comprising a CD28 polypeptide (e.g., a hinge domain of human CD28 or a portion thereof, e.g., a CD28 polypeptide consisting of the amino acid sequence of amino acids 114 to 153 of SEQ ID NO: 24); (c) a transmembrane domain comprising a CD28 polypeptide (e.g., a transmembrane domain of human CD28 or a portion thereof, e.g., a CD28 polypeptide consisting of the amino acid sequence of amino acids 154 to 179 of SEQ ID NO: 24), and (d) an intracellular signaling domain comprising (i) a CD3ζ polypeptide (e.g., a modified human CD3ζ polypeptide, e.g., one consisting of the amino acid sequence set forth in SEQ ID NO: 43), and (ii) a co-stimulatory signaling region comprising a CD28 polypeptide (e.g., an intracellular domain of human CD28 or a portion thereof, e.g., a CD28 polypeptide consisting of the amino acid sequence of amino acids 180 to 220 of SEQ ID NO: 24). In certain embodiments, the $V_H$ and $V_L$ are linked via a linker consisting of the amino acid sequence set forth in SEQ ID NO: 1. In certain embodiments, the $V_H$ and $V_L$ are positioned from the N- to the C-terminus: $V_L$-$V_H$. In certain embodiments, the CAR is designed as "CAR #2". In certain embodiments, the CAR comprises the amino acid sequence set forth in SEQ ID NO: 48, which is provided below.

```
                                        [SEQ ID NO: 48]
MDMRVPAQLLGLLLLWLPDTRCEIVLTQSPGTLSLSPGERATLSCRASQ

SVSSSYLAWYQQKPGQAPRLLIYGASSRATGIPDRFSGSGSGTDFTLTI

SRLEPEDFAVYYCQQAGAVPITFGGGTKVEIKGGGGSGGGGSGGGGSQV

QLVESGGGVVQPGRSLRLSCAASGFTFSSYGMHWVRQAPGKGLEWVALI

WYDGSNKYYADSVKGRFTISRDNSKNTLYLQMNSLRAEDTAVYYCAKPV

EGLLRGFDYWGQGTLVTVSSRAAAIEVMYPPPYLDNEKSNGTIIHVKGK

HLCPSPLFPGPSKPFWVLVVVGGVLACYSLLVTVAFIIFWVRSKRSRLL

HSDYMNMTPRRPGPTRKHYQPYAPPRDFAAYRSRVKFSRSADAPAYQQG

QNQLYNELNLGRREEYDVLDKRRGRDPEMGGKPRRKNPQEGLFNELQKD

KMAEAFSEIGMKGERRRGKGHDGLFQGLSTATKDTFDALHMQALPPR
```

An exemplary nucleic acid sequence encoding the amino acid sequence of SEQ ID NO: 48 is set forth in SEQ ID NO: 49, which is provided below.

```
                                        [SEQ ID NO: 49]
ATGGATATGAGAGTACCAGCTCAGCTGCTGGGCCTGCTGCTTTTGTGGT

TGCCGGACACACGCTGTGAGATTGTCCTGACTCAGTCTCCCGGGACTCT

GTCCCTCAGCCCCGGTGAACGCGCTACCCTTTCATGCAGAGCCTCTCAG

TCTGTGTCCAGCAGCTACCTCGCATGGTATCAGCAGAAGCCCGGACAGG

CTCCCAGGCTGTTGATCTATGGAGCTAGTAGTCGAGCAACAGGCATCCC

AGATCGCTTCTCAGGGAGCGGTTCAGGTACAGACTTCACGCTGACGATT

TCAAGGCTGGAACCCGAAGATTTTGCCGTCTATTATTGTCAACAGGCAG

GGGCTGTGCCAATCACTTTCGGGGGCGGGACCAAGGTGGAAATCAAAGG

AGGCGGAGGAAGTGGAGGAGGAGGGAGCGGTGGAGGAGGGTCACAGGTG

CAGCTGGTAGAATCTGGCGGAGGGGTCGTTCAACCAGGGAGGTCATTGC

GGTTGAGCTGCGCAGCGAGTGGTTTTACCTTCAGCAGTTATGGAATGCA

TTGGGTGAGACAAGCACCAGGAAAAGGTCTGGAGTGGGTGGCTTTGATT

TGGTACGACGGCAGTAATAAATACTACGCCGATTCTGTTAAGGGCAGAT

TTACTATTTCTCGCGACAACAGCAAGAACACGCTGTACCTGCAGATGAA

CTCTCTGAGAGCCGAAGATACAGCAGTGTACTATTGTGCTAAGCCCGTA
```

-continued

GAAGGGCTCCTGAGGGGATTCGATTATTGGGGCCAGGGTACGCTTGTGA

CAGTGTCTAGTCGGGCGGCCGCAATTGAAGTTATGTATCCTCCTCCTTA

CCTAGACAATGAGAAGAGCAATGGAACCATTATCCATGTGAAAGGGAAA

CACCTTTGTCCAAGTCCCCTATTTCCCGGACCTTCTAAGCCCTTTTGGG

TGCTGGTGGTGGTTGGTGGAGTCCTGGCTTGCTATAGCTTGCTAGTAAC

AGTGGCCTTTATTATTTTCTGGGTGAGGAGTAAGAGGAGCAGGCTCCTG

CACAGTGACTACATGAACATGACTCCCCGCCGCCCCGGGCCCACCCGCA

AGCATTACCAGCCCTATGCCCCACCACGCGACTTCGCAGCCTATCGCTC

CAGAGTGAAGTTCAGCAGGAGCGCAGACGCCCCCGCGTACCAGCAGGGC

CAGAACCAGCTCTATAACGAGCTCAATCTAGGACGAAGAGAGGAGTACG

ATGTTTTGGACAAGAGACGTGGCCGGGACCCTGAGATGGGGGGAAAGCC

GAGAAGGAAGAACCCTCAGGAAGGCCTGTTCAATGAACTGCAGAAAGAT

AAGATGGCGGAGGCCTTCAGTGAGATTGGGATGAAAGGCGAGCGCCGGA

GGGGCAAGGGGCACGATGGCCTTTTCCAGGGTCTCAGTACAGCCACCAA

GGACACCTTCGACGCCCTTCACATGCAGGCCCTGCCCCCTCGC

In certain embodiments, the CAR comprises (a) an extracellular antigen-binding domain comprising (i) a $V_H$ that comprises a CDR1 consisting of the amino acid sequence set forth in SEQ ID NO: 7, a CDR2 consisting of the amino acid sequence set forth in SEQ ID NO: 8, and a CDR3 consisting of the amino acid sequence set forth in SEQ ID NO: 9, and (ii) a $V_L$ that comprises a CDR1 consisting of the amino acid sequence set forth in SEQ ID NO: 16, a CDR2 consisting of the amino acid sequence set forth in SEQ ID NO: 12, and a CDR3 consisting of the amino acid sequence set forth in SEQ ID NO: 17, (b) a hinge domain comprising a CD28 polypeptide (e.g., a hinge domain of human CD28 or a portion thereof, e.g., a CD28 polypeptide consisting of the amino acid sequence of amino acids 114 to 153 of SEQ ID NO: 24); (c) a transmembrane domain comprising a CD28 polypeptide (e.g., a transmembrane domain of human CD28 or a portion thereof, e.g., a CD28 polypeptide consisting of the amino acid sequence of amino acids 114 to 179 of SEQ ID NO: 24), and (c) an intracellular signaling domain comprising (i) a CD3ζ polypeptide (e.g., a modified human CD3ζ polypeptide, e.g., one consisting of the amino acid sequence set forth in SEQ ID NO: 43), and (ii) a co-stimulatory signaling region comprising a CD28 polypeptide (e.g., an intracellular domain of human CD28 or a portion thereof, e.g., a CD28 polypeptide consisting of the amino acid sequence of amino acids 180 to 220 of SEQ ID NO: 24). In certain embodiments, the $V_H$ and $V_L$ are linked via a linker consisting of the amino acid sequence set forth in SEQ ID NO: 1. In certain embodiments, the $V_H$ and $V_L$ are positioned from the N- to the C-terminus: $V_L$-$V_H$. In certain embodiments, the CAR is designed as "CAR #8". In certain embodiments, the CAR comprises the amino acid sequence set forth in SEQ ID NO: 50, which is provided below.

[SEQ ID NO: 50]
MDMRVPAQLLGLLLLWLPDTRCEIVLTQSPGTLSLSPGERATLSCRASQ

SVRSSYLAWYQQKPGQAPRLLIYGASSRATGIPDRFSGSGSGTDFTLTI

-continued

SRLEPEDFAVYYCQQLFDSPYTFGGGTKVEIKGGGGSGGGGSGGGGSQV

QLVESGGGVVQPGRSLRLSCAASGFTFSSYGMHWVROAPGKGLEWVALI

WYDGSNKYYADSVKGRFTISRDNSKNTLYLQMNSLRAEDTAVYYCAKPV

EGLLRGFDYWGQGTLVTVSSRAAAIEVMYPPPYLDNEKSNGTIIHVKGK

HLCPSPLFPGPSKPFWVLVVVGGVLACYSLLVTVAFIIFWVRSKRSRLL

HSDYMNMTPRRPGPTRKHYQPYAPPRDFAAYRSRVKFSRSADAPAYQQG

QNQLYNELNLGRREEYDVLDKRRGRDPEMGGKPRRKNPQEGLFNELQKD

KMAEAFSEIGMKGERRRGKGHDGLFQGLSTATKDTFDALHMQALPPR

An exemplary nucleic acid sequence encoding the amino acid sequence of SEQ ID NO: 50 is set forth in SEQ ID NO: 51, which is provided below.

[SEQ ID NO: 51]
atggatatgagagtaccagctcagctgctgggcctgctgcttttgtggt tgccggacacacgctgtgagattgtgctgacacagtctccaggcacact ctcccttagcccgggcgagagggccactctgagctgtcgggctagtcag tcagtaaggagctcttatctggcctggtatcagcagaaaccagggcagg ctccaaggctgcttatctacggtgcaagttcccgggcaacaggcatccc agatcgctttagcggtagcgggagtgggaccgatttcactctgaccatc tcccgccttgagcccgaggatttcgctgtctattattgccagcaactgt ttgactcaccctatacgttcggtggagggaccaaagtggagatcaaggg aggcggaggaagtggaggaggaggggagcggtggaggagggtcacaggtg cagctggtagaatctggcggagggggtcgttcaaccagggaggtcattgc ggttgagctgcgcagcgagtggttttaccttcagcagttatggaatgca ttgggtgagacaagcaccaggaaaaggtctggagtgggtggctttgatt tggtacgacggcagtaataaatactacgccgattctgttaagggcagat ttactatttctcgcgacaacagcaagaacacgctgtacctgcagatgaa ctctctgagagccgaagatacagcagtgtactattgtgctaagcccgta gaagggctcctgaggggattcgattattggggccagggtacgcttgtga cagtgtctagtcgggcggccgcaattgaagttatgtatcctcctcctta cctagacaatgagaagagcaatggaaccattatccatgtgaaagggaaa caccttngtccaagtcccctatttcccggaccttctaagcccttttggg tgctggtggtggttggtggagtcctggcttgctatagcttgctagtaac agtggcctttattattttctgggtgaggagtaagaggagcaggctcctg cacagtgactacatgaacatgactccccgccgccccgggcccacccgca agcattaccagccctatgccccaccacgcgacttcgcagcctatcgctc cagagtgaagttcagcaggagcgcagacgcccccgcgtaccagcagggc cagaaccagctctataacgagctcaatctaggacgaagagaggagtacg atgttttggacaagagacgtggccgggaccctgagatggggggaaagcc -continued

```
gagaaggaagaaccctcaggaaggcctgttcaatgaactgcagaaagat aagatggcggaggccttcagtgagattgggatgaaaggcgagcgccgga ggggcaaggggcacgatggccttttccaggggctcagtacagccaccaa ggacaccttcgacgcccttcacatgcaggccctgcccctcgc
```

In certain embodiments, the CAR comprises (a) an extra-cellular antigen-binding domain comprising (i) a $V_H$ that comprises a CDR1 consisting of the amino acid sequence set forth in SEQ ID NO: 7, a CDR2 consisting of the amino acid sequence set forth in SEQ ID NO: 8, and a CDR3 consisting of the amino acid sequence set forth in SEQ ID NO: 9, and (ii) a $V_L$ that comprises a CDR1 consisting of the amino acid sequence set forth in SEQ ID NO: 11, a CDR2 consisting of the amino acid sequence set forth in SEQ ID NO: 20, and a CDR3 consisting of the amino acid sequence set forth in SEQ ID NO: 21, (b) a hinge domain comprising a CD28 polypeptide (e.g., a hinge domain of human CD28 or a portion thereof, e.g., a CD28 polypeptide consisting of the amino acid sequence of amino acids 114 to 153 of SEQ ID NO: 24); (c) a transmembrane domain comprising a CD28 polypeptide (e.g., a transmembrane domain of human CD28 or a portion thereof, e.g., a CD28 polypeptide consisting of the amino acid sequence of amino acids 114 to 179 of SEQ ID NO: 24), and (c) an intracellular signaling domain comprising (i) a CD3ζ polypeptide (e.g., a modified human CD3ζ polypeptide, e.g., one consisting of the amino acid sequence set forth in SEQ ID NO: 43), and (ii) a co-stimulatory signaling region comprising a CD28 polypeptide (e.g., an intracellular domain of human CD28 or a portion thereof, e.g., a CD28 polypeptide consisting of the amino acid sequence of amino acids 180 to 220 of SEQ ID NO: 24). In certain embodiments, the $V_H$ and $V_L$ are linked via a linker consisting of the amino acid sequence set forth in SEQ ID NO: 1. In certain embodiments, the $V_H$ and $V_L$ are positioned from the N- to the C-terminus: $V_L$-$V_H$. In certain embodiments, the CAR is designed as "CAR #15". In certain embodiments, the CAR comprises the amino acid sequence set forth in SEQ ID NO: 51, which is provided below.

[SEQ ID NO: 52]
```
MEFGLSWVFLVALLRGVQCQVQLVESGGGVVQPGRSLRLSCAASGFTFS

SYGMHWVRQAPGKGLEWVALIWYDGSNKYYADSVKGRFTISRDNSKNTL

YLQMNSLRAEDTAVYYCAKPVEGLLRGFDYWGQGTLVTVSSGGGGSGGG

GSGGGGSEIVLTQSPGTLSLSPGERATLSCRASQSVSSSYLAWYQQKPG

QAPRLLIYGASRRATGIPDRFSGSGSGTDFTLTISRLEPEDFAVYYCQQ

AGIPPYTFGGGTKVEIKRAAAIEVMYPPPYLDNEKSNGTIIHVKGKHLC

PSPLFPGPSKPFWVLVVVGGVLACYSLLVTVAFIIFWVRSKRSRLLHSD

YMNMTPRRPGPTRKHYQPYAPPRDFAAYRSRVKFSRSADAPAYQQGQNQ

LYNELNLGRREEYDVLDKRRGRDPEMGGKPRRKNPQEGLFNELQKDKMA

EAFSEIGMKGERRRGKGHDGLFQGLSTATKDTFDALHMQALPPR
```

An exemplary nucleic acid sequence encoding the amino acid sequence of SEQ ID NO: 52 is set forth in SEQ ID NO: 53, which is provided below.

[SEQ ID NO: 53]
```
atggaattcggcttgtcatgggtgttcctcgtcgcgctgctgcgcggcg ttcagtgccaggtgcagctggtagaatctggcggagggggtcgttcaacc agggaggtcattgcggttgagctgcgcagcgagtggttttaccttcagc agttatggaatgcattgggtgagacaagcaccaggaaaaggtctggagt gggtggctttgatttggtacgacggcagtaataaatactacgccgattc tgttaagggcagatttactatttctcgcgacaacagcaagaacacgctg tacctgcagatgaactctctgagagccgaagatacagcagtgtactatt gtgctaagcccgtagaagggctcctgaggggattcgattattggggcca gggtacgcttgtgacagtgtctagtggaggcggaggaagtggaggagga gggagcggtggaggagggtcagaaatcgtgctcacccagtccccgggaa cactgagtctctctccaggggaaagagcaacattgtcctgcagagcatc ccagagcgtgagctccagctacctcgcctggtatcagcagaaaccaggc caggcacccgcctgcttatctacggtgcatccaggagagccactggga tccccgatcgattctctggatcagggtctggcactgactttacattgac gatctcacggctggaacccgaggatttcgccgtgtattactgccaacag gccggaattccaccgtataccttcggaggaggtactaaagtagagatta aacggcggccgcaattgaagttatgtatcctcctccttacctagacaa tgagaagagcaatggaaccattatccatgtgaaagggaaacacctttgt ccaagtccctatttcccggaccttctaagcccttttgggtgctggtgg tggttggtggagtcctggcttgctatagcttgctagtaacagtggcctt tattattttctgggtgaggagtaagaggagcaggctcctgcacagtgac tacatgaacatgactccccgccgcccgggcccaccccgcaagcattacc agccctatgccccaccacgcgacttcgcagcctatcgctccagagtgaa gttcagcaggagcgcagacgcccccgcgtaccagcagggccagaaccag ctctataacgagctcaatctaggacgaagagaggagtacgatgtttttgg acaagagacgtggccgggaccctgagatggggggaaagccgagaaggaa gaaccctcaggaaggcctgttcaatgaactgcagaaagataagatggcg gaggccttcagtgagattgggatgaaaggcgagcgccggaggggcaagg ggcacgatggccttttccaggggctcagtacagccaccaaggacacctt cgacgcccttcacatgcaggccctgcccctcgc
```

5.4. Cells

The presently disclosed subject matter provides cells comprising a presently disclosed CD19-targeted CAR (e.g., one disclosed in Section 5.3). In certain embodiments, the cell is selected from the group consisting of cells of lymphoid lineage and cells of myeloid lineage. In certain embodiments, the cell is an immunoresponsive cell. In certain embodiments, the immunoresponsive cell is a cell of lymphoid lineage.

In certain embodiments, the cell is a cell of the lymphoid lineage. Cells of the lymphoid lineage can provide production of antibodies, regulation of cellular immune system, detection of foreign agents in the blood, detection of cells foreign to the host, and the like. Non-limiting examples of cells of the lymphoid lineage include T-cells, Natural Killer (NK) cells, B cells, dendritic cells, and stem cells from which lymphoid cells may be differentiated. In certain embodiments, the stem cell is a pluripotent stem cell (e.g., embryonic stem cell or an induced pluripotent stem cell).

In certain embodiments, the cell is a T cell. T cells can be lymphocytes that mature in the thymus and are chiefly responsible for cell-mediated immunity. T cells are involved in the adaptive immune system. The T cells of the presently disclosed subject matter can be any type of T cells, including, but not limited to, helper T cells, cytotoxic T cells, memory T cells (including central memory T cells, stem-cell-like memory T cells (or stem-like memory T cells), and two types of effector memory T cells: e.g., TEM cells and TEMRA cells), Regulatory T cells (also known as suppressor T cells), tumor-infiltrating lymphocyte (TIL), Natural killer T cells, Mucosal associated invariant T cells, and γδ T cells. Cytotoxic T-cells (CTL or killer T cells) are a subset of T lymphocytes capable of inducing the death of infected somatic or tumor cells. A patient's own T cells may be genetically modified to target specific antigens through the introduction of a CAR. In certain embodiments, the immunoresponsive cell is a T cell. The T cell can be a CD4$^+$ T-cell or a CD8$^+$ T cell. In certain embodiments, the T cell is a CD4$^+$ T cell. In certain embodiments, the T cell is a CD8$^+$ T cell. In certain embodiments, the cell is a T cell, and the presently disclosed CD19-targeted CAR is integrated at a locus within the genome of the T cell. Non-limiting examples of the loci include a TRAC locus, a TRBC locus, a TRDC locus, and a TRGC locus. In certain embodiments, the locus is a TRAC locus or a TRBC locus. Methods of targeting a CAR to a site within the genome of T cell are disclosed in WO2017180989 and Eyquem et al., *Nature*. (2017 Mar. 2); 543(7643): 113-117, both of which are incorporated by reference in their entireties.

In certain embodiments, the cell is a NK cell. Natural killer (NK) cells can be lymphocytes that are part of cell-mediated immunity and act during the innate immune response. NK cells do not require prior activation in order to perform their cytotoxic effect on target cells. In certain embodiments, the cell is a genetically modified NK cell. In certain embodiments, the cell is an edited NK cell. In certain embodiments, the cell is a NK cell derived from a stem cell. In certain embodiments, the cell is a NK cell derived from a pluripotent stem cell. In certain embodiments, the cell is an induced pluripotent stem cell (iPSC)-derived NK cell.

The cells (e.g., T cells or NK cells) can be autologous, non-autologous (e.g., allogeneic), or derived in vitro from engineered progenitor or stem cells.

The cells of the presently disclosed subject matter can be cells of the myeloid lineage. Non-limiting examples of cells of the myeloid lineage include monocytes, macrophages, neutrophils, dendritic cells, basophils, neutrophils, eosinophils, megakaryocytes, mast cell, erythrocyte, thrombocytes, and stem cells from which myeloid cells may be differentiated. In certain embodiments, the stem cell is a pluripotent stem cell (e.g., an embryonic stem cell or an induced pluripotent stem cell).

In certain embodiments, the cells can be transduced with the presently disclosed CD19-targeted CAR such that the cells express the CD19-targeted CAR.

5.5. Nucleic Acid Molecules and Vectors

The presently disclosed subject matter provides nucleic acid molecules encoding the presently disclosed CD19- targeted CARs (e.g., those disclosed in Section 5.3). Also provided are cells comprising such nucleic acid molecules.

In certain embodiments, the nucleic acid molecule further comprises a promoter that is operably linked to the presently disclosed CD19-targeted CAR.

In certain embodiments, the promoter is endogenous or exogenous. In certain embodiments, the exogenous promoter is selected from the group consisting of an elongation factor (EF)-1 promoter, a cytomegalovirus immediate-early promoter (CMV) promoter, a simian virus 40 early promoter (SV40) promoter, a phosphoglycerate kinase (PGK) promoter, a metallothionein promoter, and Ubiquitin C promoter. In certain embodiments, the endogenous promoter is selected from a TCR alpha promoter, a TCR beta promoter, and a beta 2-microglobulin promoter. In certain embodiments, the promoter is an inducible promoter. In certain embodiment, the inducible promoter is selected from the group consisting of a NFAT transcriptional response element (TRE) promoter, a CD69 promoter, a CD25 promoter, an IL-2 promoter, a 4-1BB promoter, a PD1 promoter, and a LAG3 promoter.

The presently disclosed subject matter also provides vectors comprising the presently disclosed nucleic acid molecules.

The nucleic acid molecules can be delivered into cells by art-known methods or as described herein. Genetic modification of a cell can be accomplished by transducing a substantially homogeneous cell composition with a recombinant DNA construct. In certain embodiments, a retroviral vector (e.g., gammaretroviral vector or lentiviral vector) is employed for the introduction of the DNA construct into the cell. For example, a polynucleotide encoding a CAR can be cloned into a retroviral vector and expression can be driven from its endogenous promoter, from the retroviral long terminal repeat, or from a promoter specific for a target cell type of interest. Non-viral vectors may be used as well.

For initial genetic modification of a cell to include a presently disclosed CD19-targeted CAR, a retroviral vector can be employed for transduction, however any other suitable viral vector or non-viral delivery system can be used. The CAR can be constructed in a single, multicistronic expression cassette, in multiple expression cassettes of a single vector, or in multiple vectors. Examples of elements that create polycistronic expression cassette include, but is not limited to, various viral and non-viral Internal Ribosome Entry Sites (IRES, e.g., FGF-1 IRES, FGF-2 IRES, VEGF IRES, IGF-II IRES, NF-κB IRES, RUNX1 IRES, p53 IRES, hepatitis A IRES, hepatitis C IRES, pestivirus IRES, aphthovirus IRES, picornavirus IRES, poliovirus IRES and encephalomyocarditis virus IRES) and cleavable linkers (e.g., 2A peptides, e.g., P2A, T2A, E2A and F2A peptides). Combinations of retroviral vector and an appropriate packaging line are also suitable, where the capsid proteins will be functional for infecting human cells. Various amphotropic virus-producing cell lines are known, including, but not limited to, PA12 (Miller et al., (1985) *Mol Cell Biol* (1985); 5:431-437); PA317 (Miller., et al., *Mol Cell Biol* (1986); 6:2895-2902); and CRIP (Danos et al., *Proc Natl Acad Sci* USA (1988); 85:6460-6464). Non-amphotropic particles are suitable too, e.g., particles pseudotyped with VSVG, RD114 or GALV envelope and any other known in the art.

Possible methods of transduction also include direct co-culture of the cells with producer cells (Bregni et al., *Blood* (1992); 80:1418-1422), or culturing with viral supernatant alone or concentrated vector stocks with or without appropriate growth factors and polycations (Xu et al., *Exp Hemat* (1994); 22:223-230; and Hughes et al. *J Clin Invest* (1992); 89:1817).

Other transducing viral vectors can be used to modify a cell. In certain embodiments, the chosen vector exhibits high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). Other viral vectors that can be used include, for example, adeno-viral, lentiviral, and adena-associated viral vectors, vaccinia virus, a bovine papilloma virus, or a herpes virus, such as Epstein-Barr Virus (also see, for example, the vectors of Miller, *Human Gene Thera* (1990); 15-14; Friedman, Science 244:1275-1281, 1989; Eglitis et al., *BioTechniques* (1988); 6:608-614; Tolstoshev et al., *Cur Opin Biotechnol* (1990); 1:55-61; Sharp, *The Lancet* (1991); 337:1277-78; Cornetta et al., Nucleic Acid Research and Molecular Biology 36:311-22, 1987; Anderson, *Science* (1984); 226:401-409; Moen, Blood Cells 17:407-16, 1991; Miller et al., *Biotechnol* (1989); 7:980-90; LeGal La Salle et al., *Science* (1993); 259:988-90; and Johnson, *Chest* (1995)107:77S-83S). Retroviral vectors are particularly well developed and have been used in clinical settings (Rosenberg et al., *N Engl J Med* (1990); 323:370, 1990; Anderson et al., U.S. Pat. No. 5,399,346).

Non-viral approaches can also be employed for genetic modification of a cell. For example, a nucleic acid molecule can be introduced into a cell by administering the nucleic acid in the presence of lipofection (Feigner et al., *Proc Natl Acad Sci* U.S.A. (1987); 84:7413; Ono et al., *Neurosci Lett* (1990); 17:259; Brigham et al., *Am J Med Sci* (1989); 298:278; Staubinger et al., *Methods in Enzymol* (1983); 101:512, Wu et al., *J Biol Chem* (1988); 263:14621; Wu et al., *J Biol Chem* (1989); 264:16985), or by micro-injection under surgical conditions (Wolff et al., *Science* (1990); 247:1465). Other non-viral means for gene transfer include transfection in vitro using calcium phosphate, DEAE dextran, electroporation, and protoplast fusion. Liposomes can also be potentially beneficial for delivery of DNA into a cell. Transplantation of normal genes into the affected tissues of a subject can also be accomplished by transferring a normal nucleic acid into a cultivatable cell type ex vivo (e.g., an autologous or heterologous primary cell or progeny thereof), after which the cell (or its descendants) are injected into a targeted tissue or are injected systemically. Recombinant receptors can also be derived or obtained using transposases or targeted nucleases (e.g. Zinc finger nucleases, meganucle-ases, or TALEN, CRISPR). Transient expression may be obtained by RNA electroporation.

Any targeted genome editing methods can also be used to deliver a presently disclosed CD19-targeted CAR to a cell. In certain embodiments, a CRISPR system is used to deliver a presently disclosed CD19-targeted CAR. In certain embodiments, zinc-finger nucleases are used to deliver a presently disclosed CD19-targeted CAR. In certain embodiments, a TALEN system is used to deliver a presently disclosed CD19-targeted CAR.

Clustered regularly-interspaced short palindromic repeats (CRISPR) system is a genome editing tool discovered in prokaryotic cells. When utilized for genome editing, the system includes Cas9 (a protein able to modify DNA utilizing crRNA as its guide), CRISPR RNA (crRNA, con-tains the RNA used by Cas9 to guide it to the correct section of host DNA along with a region that binds to tracrRNA (generally in a hairpin loop form) forming an active complex with Cas9), trans-activating crRNA (tracrRNA, binds to crRNA and forms an active complex with Cas9), and an optional section of DNA repair template (DNA that guides the cellular repair process allowing insertion of a specific DNA sequence). CRISPR/Cas9 often employs a plasmid to transfect the target cells. The crRNA needs to be designed for each application as this is the sequence that Cas9 uses to identify and directly bind to the target DNA in a cell. The repair template carrying CAR expression cassette need also be designed for each application, as it must overlap with the sequences on either side of the cut and code for the insertion sequence. Multiple crRNA's and the tracrRNA can be packaged together to form a single-guide RNA (sgRNA). This sgRNA can be joined together with the Cas9 gene and made into a plasmid in order to be transfected into cells.

A zinc-finger nuclease (ZFN) is an artificial restriction enzyme, which is generated by combining a zinc finger DNA-binding domain with a DNA-cleavage domain. A zinc finger domain can be engineered to target specific DNA sequences which allows a zinc-finger nuclease to target desired sequences within genomes. The DNA-binding domains of individual ZFNs typically contain a plurality of individual zinc finger repeats and can each recognize a plurality of base pairs. The most common method to gen-erate new zinc-finger domain is to combine smaller zinc-finger "modules" of known specificity. The most common cleavage domain in ZFNs is the non-specific cleavage domain from the type IIs restriction endonuclease FokI. Using the endogenous homologous recombination (HR) machinery and a homologous DNA template carrying CAR expression cassette, ZFNs can be used to insert the CAR expression cassette into genome. When the targeted sequence is cleaved by ZFNs, the HR machinery searches for homology between the damaged chromosome and the homologous DNA template, and then copies the sequence of the template between the two broken ends of the chromo-some, whereby the homologous DNA template is integrated into the genome.

Transcription activator-like effector nucleases (TALEN) are restriction enzymes that can be engineered to cut specific sequences of DNA. TALEN system operates on almost the same principle as ZFNs. They are generated by combining a transcription activator-like effectors DNA-binding domain with a DNA cleavage domain. Transcription activator-like effectors (TALEs) are composed of 33-34 amino acid repeat-ing motifs with two variable positions that have a strong recognition for specific nucleotides. By assembling arrays of these TALEs, the TALE DNA-binding domain can be engi-neered to bind desired DNA sequence, and thereby guide the nuclease to cut at specific locations in genome. cDNA expression for use in polynucleotide therapy methods can be directed from any suitable promoter (e.g., the human cyto-megalovirus (CMV), simian virus 40 (SV40), metallothio-nein promoters, or Ubiquitin C promoter), and regulated by any appropriate mammalian regulatory element or intron (e.g. the elongation factor 1a enhancer/promoter/intron structure). For example, if desired, enhancers known to preferentially direct gene expression in specific cell types can be used to direct the expression of a nucleic acid. The enhancers used can include, without limitation, those that are characterized as tissue- or cell-specific enhancers. Alter-natively, if a genomic clone is used as a therapeutic con-struct, regulation can be mediated by the cognate regulatory sequences or, if desired, by regulatory sequences derived from a heterologous source, including any of the promoters or regulatory elements described above.

Methods for delivering the genome editing agents/systems can vary depending on the need. In certain embodiments, the components of a selected genome editing method are delivered as DNA constructs in one or more plasmids. In certain embodiments, the components are delivered via viral vectors. Common delivery methods include but is not limited to, electroporation, microinjection, gene gun, impalefection, hydrostatic pressure, continuous infusion, sonication, magnetofection, adeno-associated viruses, envelope protein pseudotyping of viral vectors, replication-competent vectors cis and trans-acting elements, herpes simplex virus, and chemical vehicles (e.g., oligonucleotides, lipoplexes, polymersomes, polyplexes, dendrimers, inorganic Nanoparticles, and cell-penetrating peptides).

5.6. Formulations and Administration

The presently disclosed subject matter also provides compositions comprising the presently disclosed cells comprising a presently disclosed CD19-targeted CAR. In certain embodiments, the composition is a pharmaceutical composition that further comprises a pharmaceutically acceptable carrier.

Compositions comprising the presently disclosed cells can be conveniently provided as sterile liquid preparations, e.g., isotonic aqueous solutions, suspensions, emulsions, dispersions, or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol, and the like) and suitable mixtures thereof.

Compositions comprising the presently disclosed cells can be provided systemically or directly to a subject for inducing and/or enhancing an immune response to an antigen and/or treating and/or preventing a neoplasm. In certain embodiments, the presently disclosed cells or compositions comprising thereof are directly injected into an organ of interest (e.g., an organ affected by a neoplasm). Alternatively, the presently disclosed cells or compositions comprising thereof are provided indirectly to the organ of interest, for example, by administration into the circulatory system (e.g., the tumor vasculature). Expansion and differentiation agents can be provided prior to, during or after administration of the cells or compositions to increase production of cells in vitro or in vivo.

The quantity of cells to be administered can vary for the subject being treated. In certain embodiments, between about $10^4$ and about $10^{10}$, between about $10^4$ and about $10^7$, between about $10^5$ and about $10^7$, between about $10^5$ and about $10^9$, or between about $10^6$ and about $10^8$ of the presently disclosed cells are administered to a subject. In certain embodiments, between about $1\times10^6$ and about $5\times10^8$ of the presently disclosed cells are administered to a subject. More effective cells may be administered in even smaller numbers. Usually, at least about $1\times10^5$ cells will be administered, eventually reaching about $1\times10^{10}$ or more. In certain embodiments, at least about $1\times10^5$, $5\times10^5$, $1\times10^6$, about $5\times10^6$, about $1\times10^7$, about $2.5\times10^7$, about $5\times10^7$, about $1\times10^8$, about $1.5\times10^8$, about $2\times10^8$, or about $5\times10^8$ of the presently disclosed cells are administered to a subject. In certain embodiments, about $1\times10^6$ of the presently disclosed cells are administered to a subject. The precise determination of what would be considered an effective dose can be based on factors individual to each subject, including their size, age, sex, weight, and condition of the particular subject. Dosages can be readily ascertained by those skilled in the art from this disclosure and the knowledge in the art.

The presently disclosed cells and compositions can be administered by any method known in the art including, but not limited to, intravenous administration, subcutaneous administration, intranodal administration, intratumoral administration, intrathecal administration, intrapleural administration, intraosseous administration, intraperitoneal administration, pleural administration, and direct administration to the subject. The presently disclosed cells can be administered in any physiologically acceptable vehicle, normally intravascularly, although they may also be introduced into bone or other convenient site where the cells may find an appropriate site for regeneration and differentiation (e.g., thymus).

5.7. Methods of Treatment

The presently disclosed subject matter provides various methods of using the presently disclosed cells or compositions comprising thereof. The presently disclosed cells and compositions comprising thereof can be used in a therapy or medicament. For example, the presently disclosed subject matter provides methods for inducing and/or increasing an immune response in a subject in need thereof. The presently disclosed cells and compositions comprising thereof can be used for reducing tumor burden in a subject. The presently disclosed cells and compositions comprising thereof can reduce the number of tumor cells, reduce tumor size, and/or eradicate the tumor in the subject. The presently disclosed cells and compositions comprising thereof can be used for treating and/or preventing a neoplasm in a subject. The presently disclosed cells and compositions comprising thereof can be used for prolonging the survival of a subject suffering from a neoplasm. In certain embodiments, each of the above-noted method comprises administering the presently disclosed cells or a composition (e.g., a pharmaceutical composition) comprising thereof to achieve the desired effect, e.g., palliation of an existing condition or prevention of recurrence. For treatment, the amount administered is an amount effective in producing the desired effect. An effective amount can be provided in one or a series of administrations. An effective amount can be provided in a bolus or by continuous perfusion.

In certain embodiments, the tumor and/or neoplasm is associated with CD19. In certain embodiments, the tumor and/or neoplasm expresses CD19. In certain embodiments, the tumor and/or neoplasm overexpresses CD19. In certain embodiments, the tumor and/or neoplasm that can be treated by the presently disclosed cells and compositions is a blood cancer. Non-limiting examples of blood cancer include multiple myeloma, leukemia, and lymphomas. Non-limiting examples of leukemia include acute myeloid leukemia (AML), chronic myeloid leukemia (CIVIL), acute lymphocytic leukemia (ALL), chronic lymphocytic leukemia (CLL), acute promyelocytic leukemia (APL), mixed-phenotype acute leukemia (MLL), hairy cell leukemia, and B cell prolymphocytic leukemia. The lymphoma can be Hodgkin's lymphoma or non-Hodgkin's lymphoma. In certain embodiments, the lymphoma is B cell lymphoma (BCL).

In certain embodiments, the tumor and/or neoplasm is a B cell malignancy. Non-limiting examples of B cell malignancy include B cell lymphoma (BCL), B cell acute lymphocytic leukemia (ALL), B cell chronic lymphocytic leukemia (CLL), multiple myeloma (MM), CLL with Richter's transformation, and CNS lymphoma. B cell lymphoma includes B cell non-Hodgkin lymphoma (NHL) and B cell Hodgkin's lymphoma. In certain embodiments, the tumor and/or neoplasm is B cell lymphoma. In certain embodiments, the B cell lymphoma is relapsed or refractory (R/R) B cell lymphoma.

In certain embodiments, the subject is a human subject. The subjects can have an advanced form of disease, in which case the treatment objective can include mitigation or reversal of disease progression, and/or amelioration of side effects. The subjects can have a history of the condition, for which they have already been treated, in which case the therapeutic objective will typically include a decrease or delay in the risk of recurrence.

As a consequence of surface expression of a presently disclosed CD19-targeted CAR, adoptively transferred cells are endowed with augmented and selective cytolytic activity at the tumor site. Furthermore, subsequent to their localization to tumor and their proliferation, the cells turn the tumor site into a highly conductive environment for a wide range of cells involved in the physiological anti-tumor response.

Further modification can be introduced to the presently disclosed cells to avert or minimize the risks of immunological complications (known as "malignant T-cell transformation"), e.g., graft versus-host disease (GvHD), or when healthy tissues express the same target antigens as the tumor cells, leading to outcomes similar to GvHD. A potential solution to this problem is engineering a suicide gene into the presently disclosed cells. Suitable suicide genes include, but are not limited to, Herpes simplex virus thymidine kinase (hsv-tk), inducible Caspase 9 Suicide gene (iCasp-9), and a truncated human epidermal growth factor receptor (EGFRt) polypeptide. In certain embodiments, the suicide gene is an EGFRt polypeptide. The EGFRt polypeptide can enable T-cell elimination by administering anti-EGFR monoclonal antibody (e.g., cetuximab). EGFRt can be covalently joined to the upstream of the CD19-targeted CAR. The suicide gene can be included within the vector comprising nucleic acids encoding a presently disclosed CD19-targeted CAR. In this way, administration of a prodrug designed to activate the suicide gene (e.g., a prodrug (e.g., AP1903 that can activate iCasp-9) during malignant T-cell transformation (e.g., GVHD) triggers apoptosis in the suicide gene-activated cells expressing the CD19-targeted CAR. The incorporation of a suicide gene into the a presently disclosed CD19-targeted CAR gives an added level of safety with the ability to eliminate the majority of receptor-expressing cells within a very short time period. A presently disclosed cell incorporated with a suicide gene can be pre-emptively eliminated at a given timepoint post the cell infusion, or eradicated at the earliest signs of toxicity.

7. EXAMPLE

The presently disclosed subject matter will be better understood by reference to the following Example, which is provided as exemplary of the presently disclosed subject matter, and not by way of limitation.

Example 1—Identification and Characterization of Anti-CD19 Antibodies

This Example demonstrates characterization of anti-CD19 antibodies comprising the $V_H$ and $V_L$ of the scFvs disclosed herein. Human anti-CD19 antibodies were derived from and produced in Adimab yeast. Antigens were biotinylated using the EZ-Link Sulfo-NHS-Biotinylation Kit (Thermo Scientific, Cat #21425). The antigens were concentrated to about 1 mg/mL and buffer exchanged into PBS before addition of 1:7.5 molar ratio of biotinylation reagent. The mixture was held at 4C overnight prior to another buffer exchange to remove free biotin in the solution. Biotinylation was confirmed through streptavidin sensor binding of the labeled proteins on a ForteBio.

Eight naïve human synthetic yeast libraries each of ~$10^9$ diversity were propagated as previously described (see, e.g., Y. Xu et al, PEDS 26(10), 663-70 (2013); WO2009036379; WO2010105256; and WO2012009568.)

For the first two rounds of selection, a magnetic bead sorting technique utilizing the Miltenyi MACS system was performed, as previously described (see, e.g., Siegel et al, J Immunol Methods 286(1-2), 141-153 (2004).) Briefly, yeast cells (~1010 cells/library) were incubated with biotinylated antigen for 30 min at 30° C. in wash buffer (phosphate-buffered saline (PB S)/0.1% bovine serum albumin (BSA)). After washing once with 40 mL ice-cold wash buffer, the cell pellet was resuspended in 20 mL wash buffer, and Streptavidin MicroBeads (500 µl) were added to the yeast and incubated for 15 min at 4° C. Next the yeast were pelleted, resuspended in 5 mL wash buffer, and loaded onto a Miltenyi LS column. After the 5 mL were loaded, the column was washed 3 times with 3 mL wash buffer. The column was then removed from the magnetic field, and the yeast were eluted with 5 mL of growth media and then grown overnight.

The third round of selection was performed using flow cytometry (FACS). Approximately $2\times10^7$ yeast were pelleted, washed three times with wash buffer, and incubated at 30° C. with 100-200 nM biotinylated antigen under equilibrium conditions. The fourth and fifth rounds of selections were performed by incubating biotinylated NALM-6 and Raji cells with the selected yeast output from the round 3 FACS. After incubation, pre-washed M-280 Strepavidin Dynabeads (Cat #60210) were added to the yeast/mammalian cell complexes and incubated. Next, the complexes were separated using a DynaMag-2 magnet and the non-binding supernatants were removed. The bead/cell complexes were washed three times with 1 mL of selection buffer. The captured complexes were then transferred into flasks containing yeast growth media for propagation. In the sixth round of selection, propagated yeast were subjected to either and additional round of NALM-6/Raji cell selection, selection with 100 nM recombinant CD19 antigen, or negative selection with a polyspecificity reagent (PSR) to remove non-specific antibodies.

For the PSR depletion, the libraries were incubated with a 1:10 dilution of biotinylated PSR reagent as previously described (see, e.g., Y. Xu et al, PEDS 26(10), 663-70 (2013).) Yeast were then washed twice with wash buffer and stained with goat F(ab')2 anti-human kappa-FITC (LC-FITC) diluted 1:100 (Southern Biotech, Cat #2062-02) and either Streptavidin-AF633 (SA-633) diluted 1:500 (Life Technologies, Cat #S21375) or Extravidin-phycoerthyrin (EA-PE) diluted 1:50 (Sigma-Aldrich, Cat #E4011), secondary reagents for 15 min at 4° C. After washing twice with ice-cold wash buffer, the cell pellets were resuspended in 0.3 mL wash buffer and transferred to strainer-capped sort tubes. Sorting was performed using a FACS ARIA sorter (BD Biosciences) and sort gates were determined to select for antibodies with desired characteristics. Selection rounds were repeated until a population with all of the desired characteristics was obtained. After the final round of sorting, yeast were plated and individual colonies were picked for characterization.

Light Chain Diversification

Heavy chains from the naïve output were used to prepare light chain diversification libraries used for additional selection rounds. Heavy chain plasmids were extracted from the yeast, propagated in and subsequently purified from *E. coli*, and transformed into a light chain library with a diversity of $5 \times 10^6$. Selections were performed on these libraries as described above, i.e., with one round of MACS, two rounds of cell selection with either Raji or NALM-6 cells, followed by a fourth round FACS selection using recombinant CD19 antigen. Specific to the light chain diversification, the Raji and NALM-6 cells selections incorporated an initial negative selection with engineered Raji and NALM-6 cells that had undergone targeted genetic knockout of the CD19 gene. Following the depletion with the CD19 knockout cells, a positive selection was performed using engineered Raji and NALM-6 cells that expressed both endogenous CD19 and overexpressed. In the different FACS selection rounds, the libraries were evaluated for (Poly-Specificity Reagent) PSR binding, species cross-reactivity, and affinity pressure by antigen titration. Sorting was performed in order to obtain a population with the desired characteristics. Individual colonies from each FACS selection round described above were picked for sequencing and characterization.

Antibody Production and Purification

Yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0.

ForteBio $K_D$ Measurements

These anti-CD19 antibodies were tested for their binding affinity on soluble CD19 in a ForteBio Octet system (Octet RED384 generally as previously described (see, e.g., Estep et al, Mabs 5(2), 270-278 (2013)). Briefly, ForteBio affinity measurements were performed by loading IgGs on-line onto AHC sensors. The antibodies were immobilized on anti-human IgG pins and bound to soluble CD19-HSA fusion protein (CD19 extracellular domains fused to human serum albumin). Sensors were equilibrated off-line in assay buffer for 30 min and then monitored on-line for 60 seconds for baseline establishment. Sensors with loaded IgGs were exposed to 100 nM soluble CD19-HSA fusion protein antigen for 3 minutes, and afterwards were transferred to assay buffer for 3 min for off-rate measurement. All kinetics were analyzed using the 1:1 binding model. A summary of the binding kinetics are provided in Table 1. The affinities of exemplary antibodies ranged between 8 nM and 20 nM. All the anti-CD19 antibodies shown in Table 1 comprise a $V_H$ comprising the amino acid sequence set forth in SEQ ID NO: 10.

TABLE 1

Binding kinetics of anti-CD19 antibodies

| CD19 Antibody | SEQ ID NO. of the $V_L$ amino acid sequence | IgG $K_D$ (M) monovalent | kon (1/Ms) | koff (1/s) |
|---|---|---|---|---|
| Antibody 2 | 14 | 9.01E−09 | 6.15E+04 | 5.54E−04 |
| Antibody 4 | 58 | 9.27E−09 | 2.35E+04 | 2.18E−04 |
| Antibody 5 | 60 | 1.04E−08 | 7.56E+04 | 7.85E−04 |
| Antibody 8 | 18 | 8.22E−09 | 5.52E+04 | 4.54E−04 |
| Antibody 6 | 62 | 6.40E−09 | 7.56E+04 | 4.84E−04 |

TABLE 1-continued

Binding kinetics of anti-CD19 antibodies

| CD19 Antibody | SEQ ID NO. of the $V_L$ amino acid sequence | IgG $K_D$ (M) monovalent | kon (1/Ms) | koff (1/s) |
|---|---|---|---|---|
| Antibody 7 | 64 | 1.49E−08 | 7.00E+04 | 1.05E−03 |
| Antibody 1 | 67 | 3.29E−08 | 5.34E+04 | 1.76E−03 |
| Antibody 15 | 22 | 2.08E−08 | 6.98E+04 | 1.45E−03 |

Example 2—Generation of CD19-Targeted CARs and CAR Expression

Three CD19-targeted CARs "CAR #2", "CAR #8", and "CAR #15" were generated. The expression of CAR molecules on the cell surface was examined using PE conjugated anti-human LNGFR antibody followed by flow cytometry analysis. LNGFR was co-expressed with CAR through via a self-cleaving linker 2A sequence, thus the expression of LNGFR were used as indication of CAR expression. The results are shown in Table 2.

TABLE 2

| CAR-T # | LNGFR+ % |
|---|---|
| CAR #2 | 53.7% |
| CAR #8 | 64.1% |
| CAR #15 | 18.5% |
| Positive control | 31.6% |
| UTD | 0.35% |

UTD: un-transduced T cells

Positive control is a CD19-targeted CAR comprising a murine scFv SJ25c1 and CD3ζ1XX, termed "1928z1XX CAR".

Example 3—In Vitro Activities of CD19-Targeted CARs

Figure 1A:
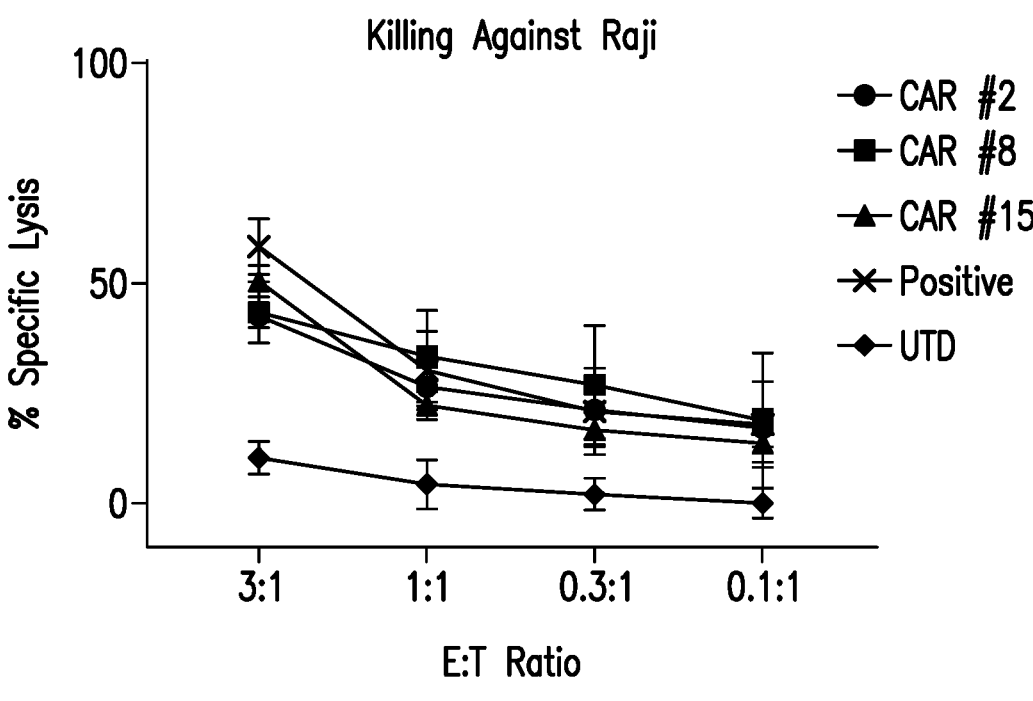
Figure 1B:
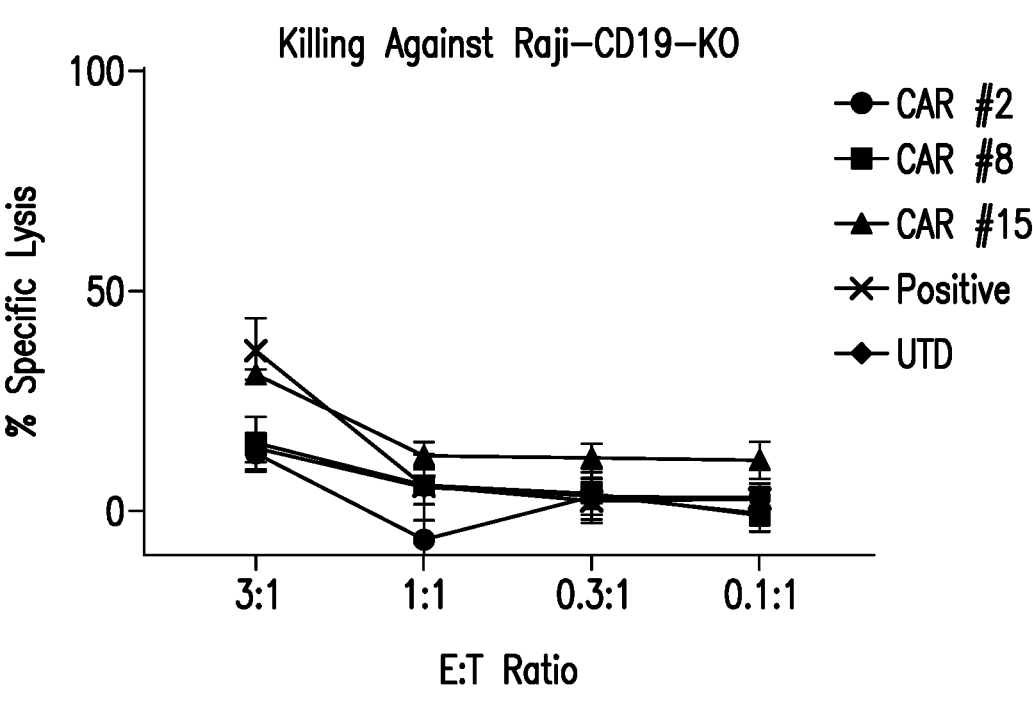

The cytotoxicity of these CD19-targeted CARs against CD19-expressing Raji cancer cell lines and CD19 knock-out Raji cells was examined. Each target cell line was seeded in a 384-well plate, and CD19 CAR-T or untransduced T cells (UTD) were added at 4 effector-to-target (E:T) ratios. Wells with target cells only and wells with effector cells only were included as controls. After 24 hours, cell viability was measured using CellTiter-Glo® One Solution Assay (Promega, G8462). Percent viability of target cells was calculated from the luminescence signals of the co-culture wells, after first subtracting the signals of the effector-cells-only wells, then dividing by the signals of the target-cell-only wells. Percent killing was calculated by subtracting the percent viability of target cells from 100%. As shown in FIGS. 1A and 1B, T cells comprising CAR #2, T cells comprising CAR #8, and T cells comprising CAR #15 all demonstrated cell killing activity against Raji cells, in contrast to CD19 knock-out Raji cells, indicating the killing activity of T cells comprising these CD19-targeted CARs was antigen-dependent.

To confirm antigen dependent cytotoxicity, T cells comprising these CD19-targeted CARs were co-cultured with CD19-expressing Raji cancer cell lines or CD19 knock-out Raji cells. Each target cell line was labelled with cell trace violet dye and then seeded in a 96 well plate, and CD19 CAR-T or untransduced T cells (UTD) were added at 2 effector-to-target (E:T) ratios. Wells with target cells only and wells with effector cells only were included as controls.

Figure 2A:
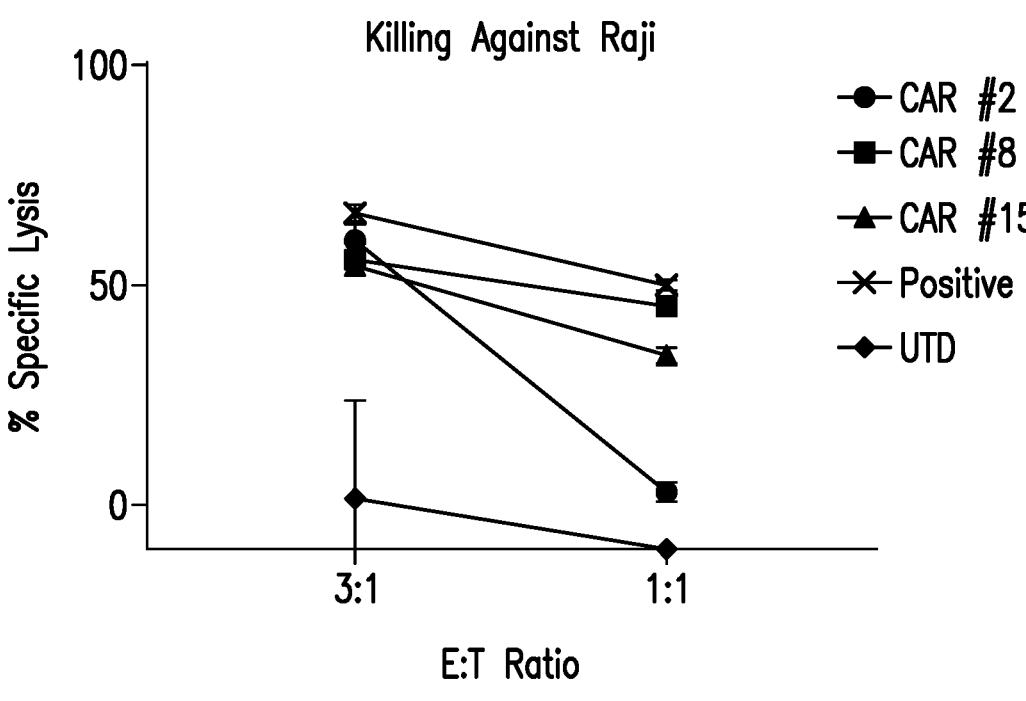
Figure 2B:
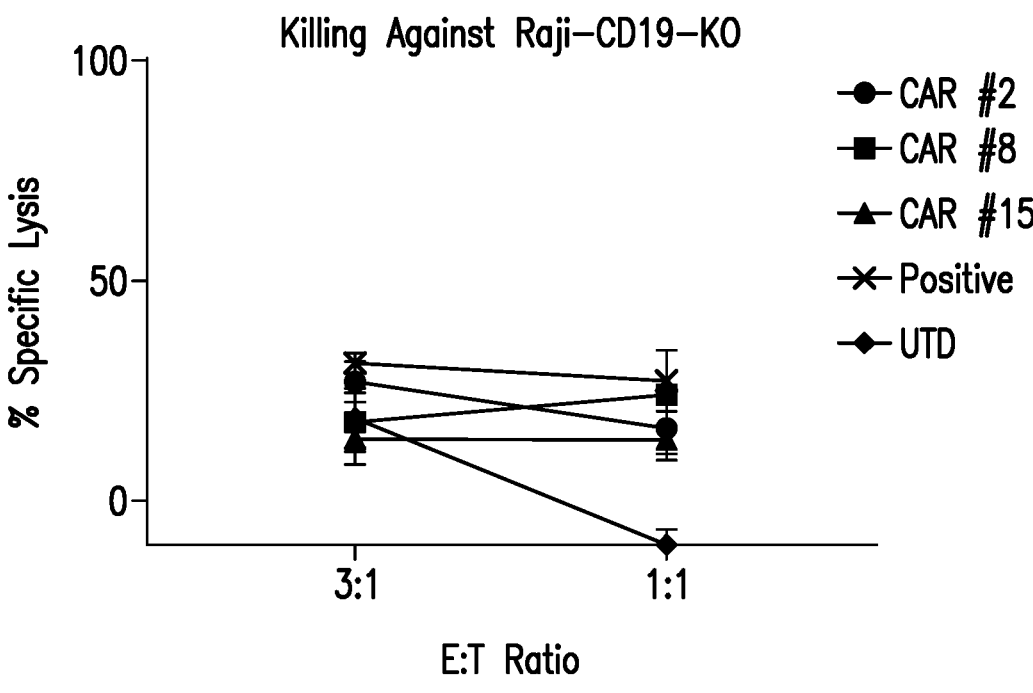

After 20 hours, cell viability was measured using live/dead dye staining followed by flow cytometry analysis. Percent viability of target cells was calculated from live cells measured by flow cytometry, then dividing by the signals of the target-cell-only wells. Percent killing was calculated by subtracting the percent viability of target cells from 100%. As shown in FIGS. 2A and 2B, T cells comprising CAR #2, T cells comprising CAR #8, and T cells comprising CAR #15 all demonstrated cell killing activity against Raji cells, in contrast to CD19 knock-out Raji cells, confirming the killing activity of T cells comprising these CD19-targeted CARs was antigen-dependent.

Figure 3A:
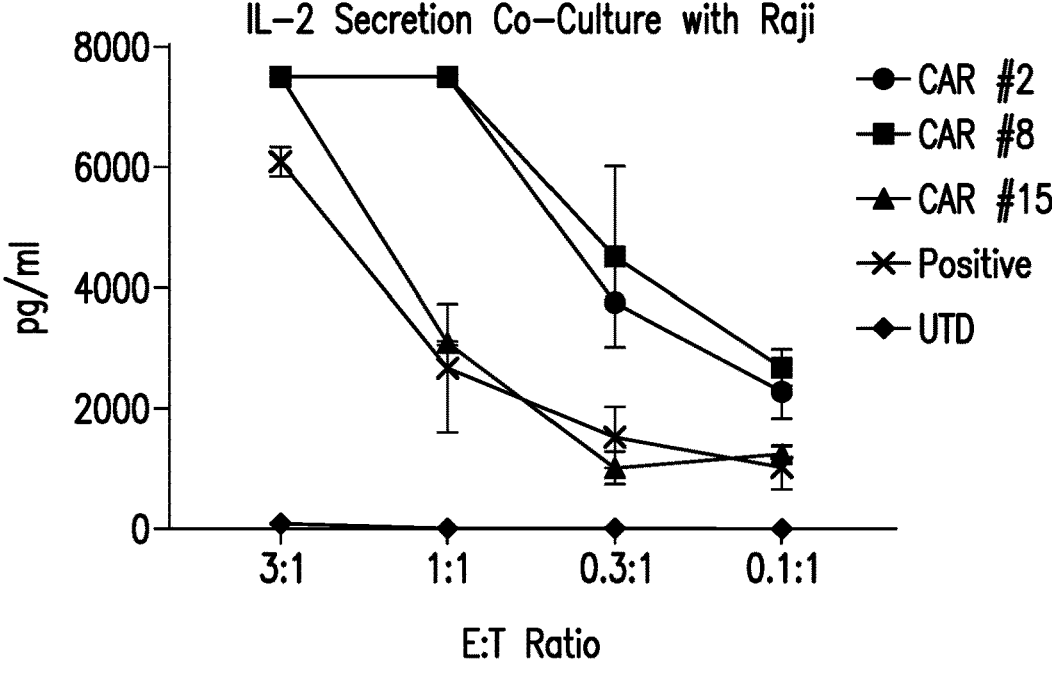
Figure 3B:
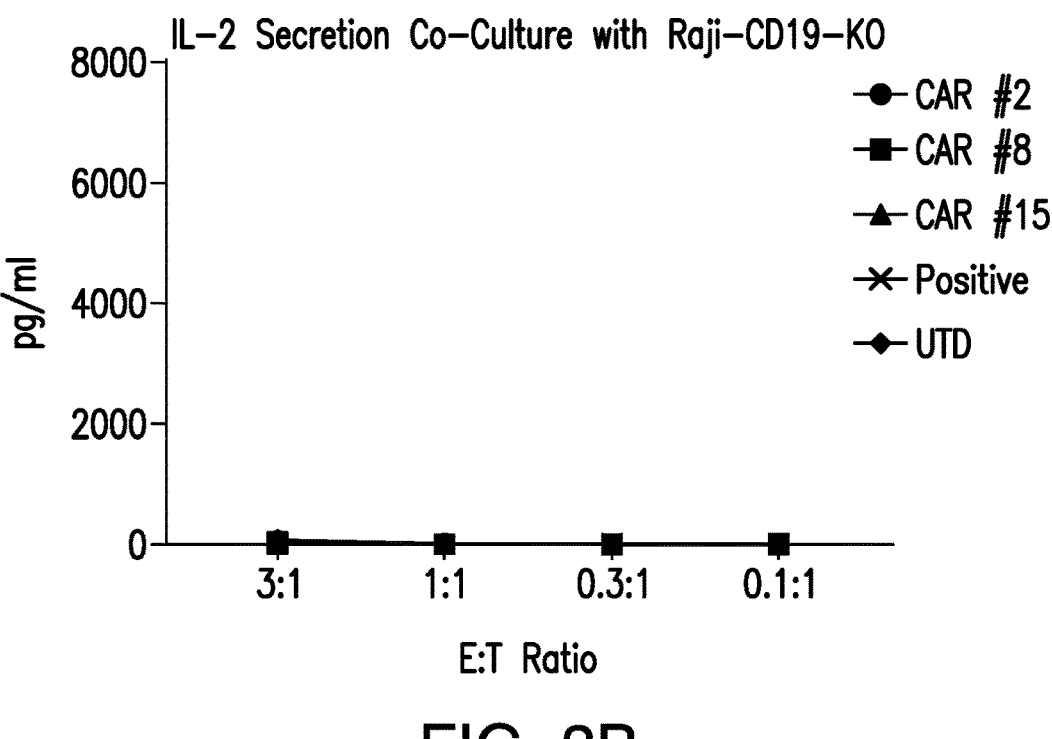
Figure 4A:
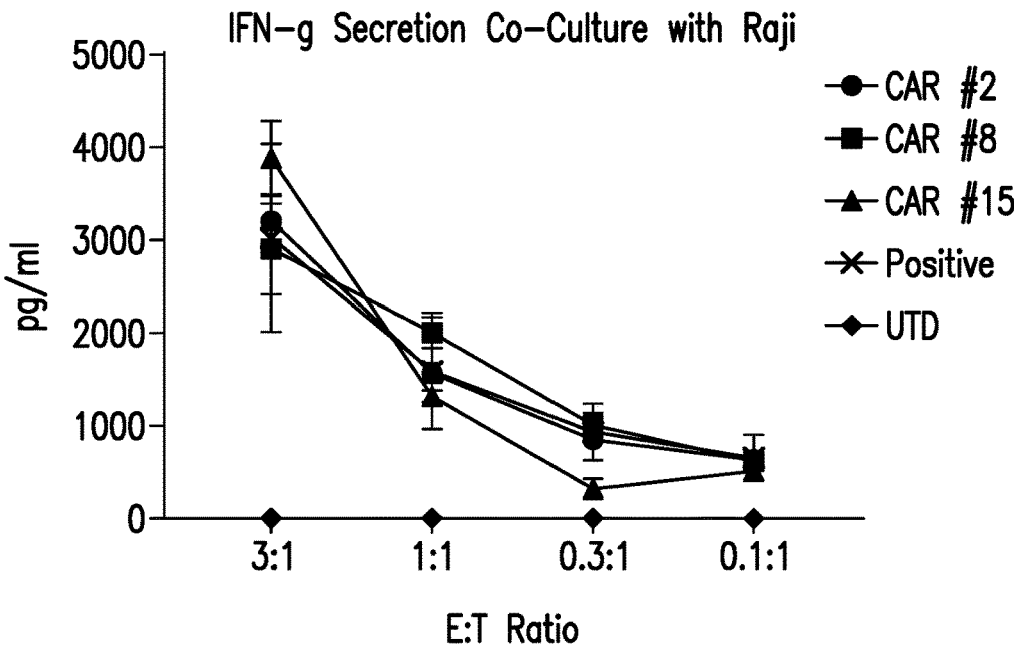
Figure 4B:
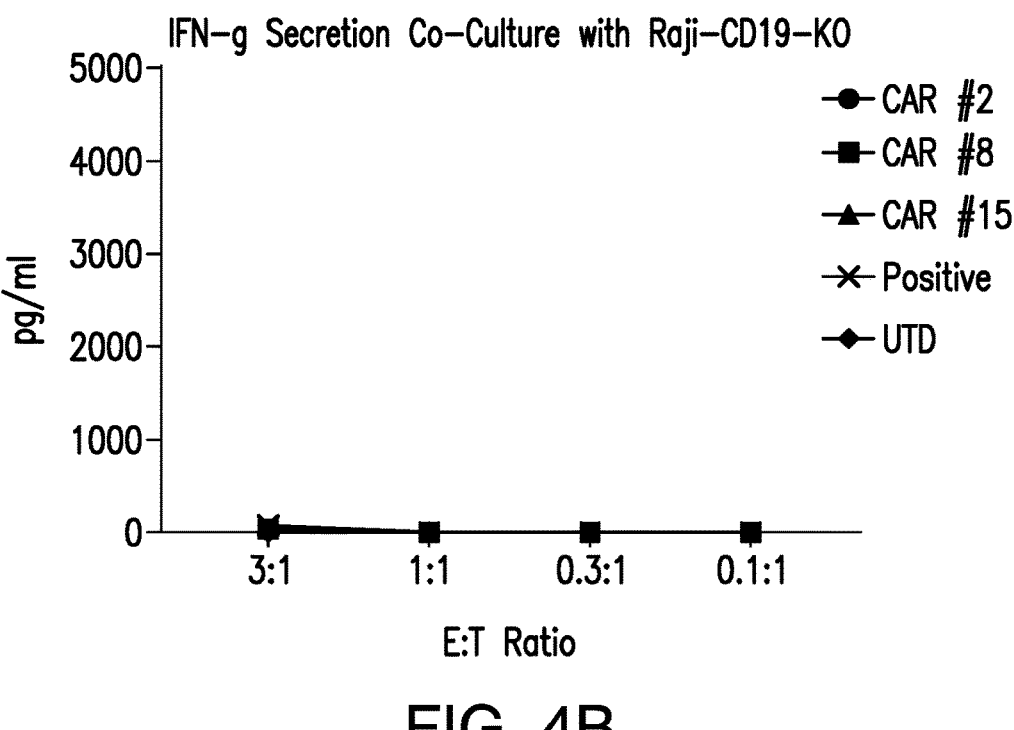

Antigen independent cytokines (IL-2 and IFN-γ) secretion was evaluated with T cells comprising CAR #2, T cells comprising CAR #8, and T cells comprising CAR #15 co-culture with CD19-expressing Raji cancer cell lines and CD19 knock-out Raji cells. Each target cell line was seeded in a 384-well plate, and CD19 CAR-T or untransduced T cells (UTD) were added at 4 effector-to-target (E:T) ratios. Wells with target cells only and wells with effector cells only were included as controls. After 24 hours, supernatant was and secreted IFN-γ and IL2 in the supernatant were detected using the Intellicyt QBeads Human PlexScreen kit (Sartorius, 90702). The IL-2 secretion results are shown in FIGS. 3A and 3B, and the IFN-γ secretion results are shown in FIGS. 4A and 4B. T cells comprising these CD19-targeted CARs showed IL-2 and IFN-γ secretion when co-culture with Raji cells, in contrast to CD19 knock-out Raji cells, indicating antigen-dependent cytokine release of T cells comprising these CD19-targeted CARs.

Example 4—In Vivo Activities of CD19-Targeted CARs

The in vivo activity of T cells comprising these CD19-targeted CARs was next investigated.

Figure 5:
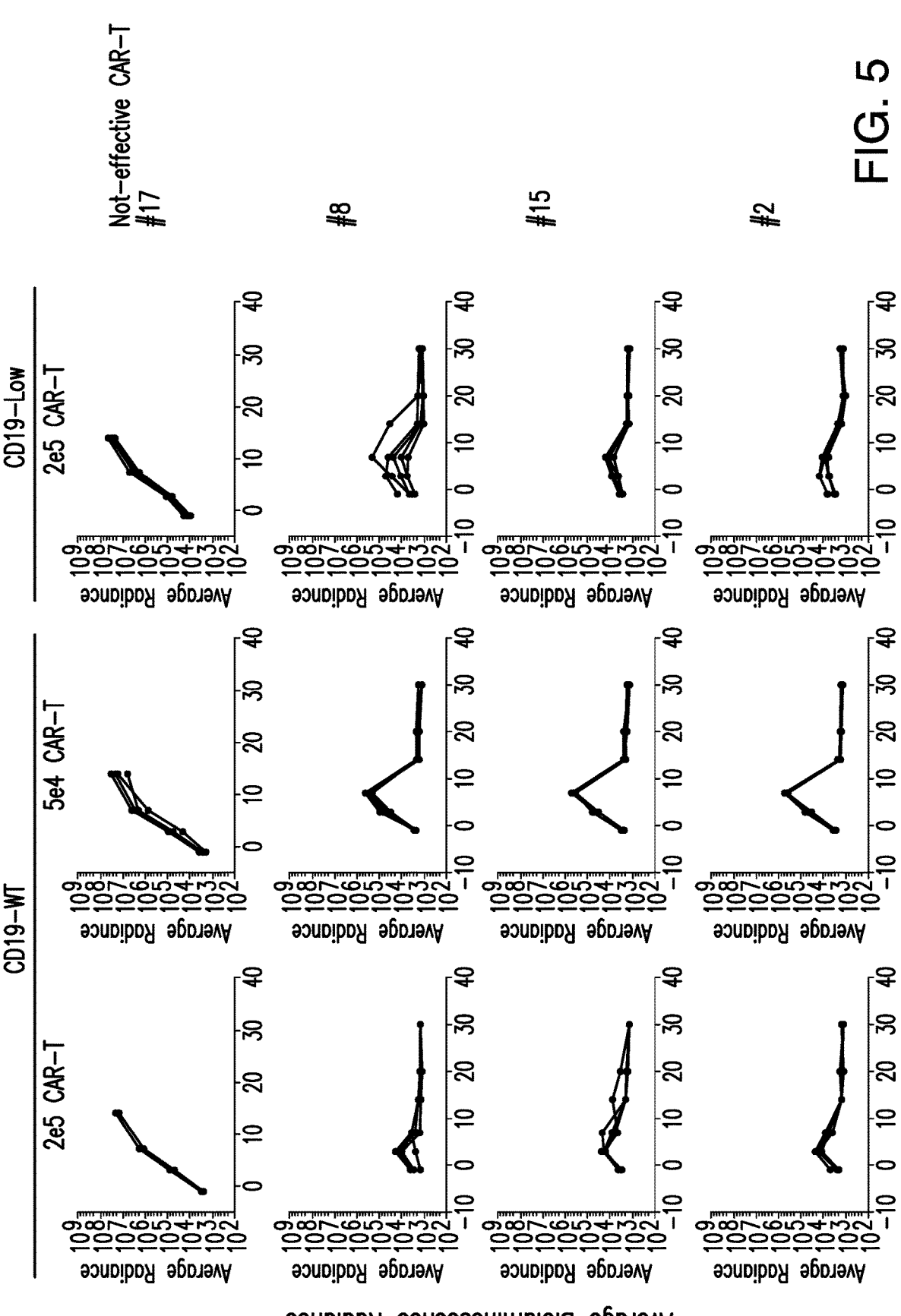
FIG. 5 shows in vivo anti-tumor activity of T cells comprising CD19-targeted CARs. #17 is a negative control, which is a CD19-targeted CAR having no detectable in vivo activity.

NOD-scid IL2Rg$^{null}$ (NSG) mice were intravenously (iv) injected with $0.5 \times 10^6$ firefly luciferase expressing NALM6 cells (B-ALL cell line) with either wild type CD19 levels (CD19-WT) or reduced CD19 levels (CD19-Low, a Nalm6 clone generated by CRISPR-Cas9-editing of the CD19 gene, followed by CD19 re-expression using a lentiviral vector). CD19-WT (blue, red) and CD19⁻Low (green) NALM6 bearing mice were treated with a single intravenous injection of fresh $5 \times 10^4$ (red) or $2 \times 10^5$ (blue, green) #17, #8, #15 or #2 CAR T cells 4 days later. CAR T cell treated-mice were imaged repeatedly over 60-100 days to assess tumor response and potential relapse for a rigorous assessment of CAR T cell potency. Tumor burden was analyzed by bioluminescence imaging until day 30 post T cell infusions and is demonstrated for each mouse at indicated time points in FIG. 5. #2 CAR T cells demonstrated rapid and effective antitumor activity, resulting in complete tumor eradication of NALM6 WT and NALM6 CD19-Low cells at all tested T cell doses. #17 showed insufficient tumor control, leading to rapid tumor progression and served as control.

Example 5—Binding Epitope of #2 scFv

Anti-CD19 antibody binding to CD19 expressing NALM6 cell lines was determined by serial dilution and flow cytometry. CD19-T2 binder, SJ25c1 (from the 19-28z CAR), and FMC63 (from the Kymriah's "Tisagenlecleucel" and Yescarta's "Axicabtagene ciloleucel") scFvs competitive binding to CD19 was evaluated by Biacore SPR. A mixture of 100 nM CD19-HSA-His (Takeda, Cambridge) and increasing concentration of soluble CD19-T2 SJ25c1 or FMC63 scFv (0, 50 nM, 100 nM, 200 nM, 400 nM, and 800 nM) were flowed through a Biacore CMS chip with immobilized CD19-T2 scFv for 3 minutes. The dissociation of the complexes bound on the chip was evaluated by flowing HBS-EP buffer (300 mM NaCl) for 5 minutes. The CD19-HSA-His was purified from HEK293 that was transiently transfected with a pcDNA3.4 plasmid (ThermoFisher) comprising a gene expressing the CD19 extracellular domain fused to 10 decahistine tag, TEV cleavage site, GS linker, and HSA. The recombinant CD19-HSA-His10 was purified by using a nickel-affinity chromatography. The amino sequence of the CD19-HSA-His10 is shown in FIG. 6.

The epitope binding data of SJ25c, FMC63, and #2 scFv are shown in FIG. 7. As shown in FIG. 7, #2 scFv competed for binding to CD19 with FMC63 and SJ25C1. These findings establish that the #2 scFv, FMC63, and SJ25C1 scFv's bind to an overlapping epitope on CD19. An unrelated antibody (anti-CTLA4 VHH), which does not bind to CD19, failed to compete with #2 scFv for binding to CD19.

Example 6—Pharmacology Studies

Summary

In support of a first-in-human clinical trial, a series of studies were conducted to demonstrate the improved efficacy of #2 CAR T cells (represented as "19(T2)28z1XX CAR" in this Example) relative to 1928z CAR T cells (which have been extensively administered in prior clinical trials), as measured by increased anti-tumor potency at low T cell doses and increased durability of response. CAR T cells engineered to express either CAR displayed comparable cytolytic activity, cytokine secretion, and proliferation in vitro, but the #2 CAR T cells achieved greater potency in vivo owing to their greater functional persistence (Feucht, et al. *Nature Medicine* (2019); 25(1):82-88).

Results

The in vitro cytotoxic activity of #2 CAR T cells and 1928z-1XX CAR T cells were measured using an 18-h bioluminescence assay. These two CARs are identical, but for the different scFv (#2 vs. SJ25c1). The retroviral vector comprising the #2 CAR is shown in FIG. 8. Recombinant retroviral particles were generated from HEK293 GalV9 packaging cells, as previously described (Przybylowski et al., (2006); 13(1):95-100). Firefly luciferase (FFL)-expressing NALM6 cells were used as target cells. The T cells were isolated by negative selection from human PMBCs, activated with CD3/CD28 antibodies bound to magnetic beads for 48 hrs, and after bead removal, was transduced with γ-retroviral vectors expressing the CARs. CAR+ population was determined by LNGFR detection, which was co-expressed with the CAR gene. The CAR+ T cells were incubated with target NALM6 cells at different effector (E) to target (T) ratios for 18h, followed by quantification of FFL activity. The cytotoxic activity of the #2 CAR T cells was compared to that of the 1928z-1xx CAR T cells, which were previously shown to kill CD19⁺ NALM6 cells in vitro effectively (Feucht et al., *Nature Medicine* (2019); 25(1): 82-88). Untransduced (UT) T cells were used as negative controls. NALM6-CD19KO is a cell line generated by CRISPR-Cas9-editing of the CD19 gene (Hamieh et al., *Nature* (2019); 568(7750):112-116) and was used to demonstrate the specificity of the CAR T cells cytotoxic activity. A representative experiment is shown (n=2 independent experiments on 2 healthy donors). As shown in FIG. 10, the #2 CAR T cells and 1928z-1XX CAR T cells showed comparable cytotoxicity.

Next, the in vivo activities of #2 CAR T cells (represented as "19(T2)28z1XX CAR") and 1928z-1XX CAR T cells were measured. NALM6, a pre-B acute lymphoblastic leukemia human tumor cell line expressing normal (wt) or low (low) levels of CD19 antigen, were transduced with firefly luciferase and green fluorescent protein (GFP) (Zhao et al., *Cancer Cell* (2015); 28:415-428). CD19$^+$ wt (blue) and CD19$^+$ low (red) NALM6 bearing mice were treated with a single intravenous injection of fresh $2\times10^5$ untransduced T cells, #2 CAR T cells, or 1928z-1XX CAR T cells. The tumor burden in each mouse was monitored by bioluminescence imaging (BLI) for 85 days. There were five mice in each group, and the response of each mouse is shown in FIG. 11. As shown in FIG. 11, #2 CART cells and 1928z1XX CART cells had similar tumor eradication kinetics. The CAR cDNA was co-expressed with the LNGFR reporter (to monitor T cell transduction). "19(T2)28z1XX CAR" represents "#2 CAR".

The activities of #2 CAR T cells and 1928z CAR T cells were studied and compared. First, CAR expression and phenotypes of 1928z CAR T cells and #2 CAR T cells (represented as "19(T2)28z1XX CAR T cells") were measured. A vector comprising 1928z CAR is shown in FIG. 12. CD4$^+$ and CD8$^+$ T cells were transduced with γ-retroviral vectors, which express the 1928z CAR or #2 CAR (represented as "19(T2)28z1XX CAR") and produced using a process representative of the clinical manufacturing. Because the SJ25c1 scFv in the SGF-1928z is derived from mouse and the #2 scFv (represented as "19(T2) scFv") is humanized, two different goat antibodies specific to either mouse (GAM) or human (GAH) Fc portion of the IgG heavy chain were used to detect CAR surface expression. As shown in FIG. 13, more than 50% of the CD4$^+$ and CD8$^+$ T cells expressed the CARs.

Next, the phenotypes of CAR T cells were determined by flow cytometry using antibodies that recognize markers for naïve, central memory, effector memory, and effector T cells as well as for exhaustion markers (LAG3, PD1, and Tim3). "SFG-T2-1XX-GAH" refers to CD4/CD8 T cells transduced with γ-retroviral vector expressing the 19(T2)28z1XX CAR (representing "#2 CAR"), while "SFG-1928z-GAM" were from T cells transduced with γ-retroviral vector expressing the 1928z CAR. As shown in FIG. 14, the phenotypes of the 1928z CAR T cells and #2 CART cells were similar. The ratio of CD4/CD8 T cells was similar in 1928z and #2 CAR T cells, and T cell differentiation states were comparable between both CAR groups (for CD4 and CD8 T cells) as determined by CD62L/CD45RA and CD45RA/CCR7 staining. Expression of exhaustion markers PD1, LAG3, and TIM3 did not reveal major differences between both CAR T cell groups.

Subsequently, the in vivo activities of #2 CAR T cells and 1928z CAR T Cells were assessed and compared. Four days after $5\times10^5$ CD19$^+$ NALM6-FFLuc/GFP cells were injected in the tail vein of the mice, thawed cryopreserved untransduced or CAR T cells were given. As shown in FIG. 15, #2 CAR T cells (represented as "19(T2)28z1XX CAR T cells") provided superior tumor control relative to 1928z CAR T cells. The survival of the CD19$^+$ NALM6 bearing mice that were treated with untransduced or CAR T cells is plotted in a Kaplan-Meier curve plot as shown in FIG. 16. As shown in FIG. 16, CD19$^+$ NALM6 bearing mice treated with #2 CAR T cells (represented as "19(T2)28z1XX CAR T cells") survived longer than mice treated with 1928z CAR T cells at all CAR T cell doses below $1\times10^6$ cells per mouse. All 1928z CAR T cell recipients died by day 25 while only one mouse died in the study groups that received #2 CAR T cells (represented as "19(T2)28z1XX CAR T cells"). At the highest dose ($1\times10^6$), one mouse died in both control and test groups.

In vivo persistence of #2 CAR T cells (represented as "19(T2)28z1XX CART cells") and 1928z CAR T cells in the CD19$^+$ NALM6 leukemia mouse model was also measured. Persistence of CART cells after 17 days post-treatment, and the numbers of CART cells in the bone marrow (n=5 per group) are shown in FIG. 17. PD1, LAG3, and TIM3 expression percentage of CART cells, and $T_n$, $T_{cm}$, $T_{eff}$, and $T_{em}$ percentages of CART cells are presented in FIG. 17.

As shown in FIG. 17, #2 CART cells (represented as "19(T2)28z1XX CAR T cells") were readily detected in bone marrow by day 17, comprising both CD4$^+$ and CD8$^+$ CAR T cells. 1928z CAR T cells were few, consistent with their limited persistence (Zhao et al., *Cancer Cell* (2015); 28:415-428). The respective phenotypes of persisting T cells detected on day 17 were overall similar (Tn, Tcm, and Tem), showing a slightly higher fraction of effector T cells (Teff) in the #2 CAR (represented as "19(T2)28z1XX CAR") group. The latter expressed more PD1 and comparable levels of LAG3 and TIM3. This observation corroborates the greater persistence of CAR T cells expressing the CD28/CD3z-1XX signaling motif (Feucht et al., *Nature Medicine* (2019); 25(1):82-88).

These results confirm the greater potency of #2 CAR T cells (represented as "19(T2)28z1XX CAR T cells") relative to 1928z CAR T cells (higher tumor eradication at 4 dose levels). This study further establishes that the phenotype of #2 CAR T cells (represented as "19(T2)28z1XX CAR T cells") is overall similar to that of 1928z CAR T cells and is consistent with #2 CAR T cells (represented as "19(T2) 28z1XX CAR T cells") achieving better tumor control owing to their greater persistence relative to the shorter-lived 1928z CART cells.

Methods and Materials

Cytolytic Assay

Luciferase-based assays were used to measure the cytotoxicity of T cells transduced with different CAR constructs. NALM6-expressing FFLuc-GFP served as the target cells. The effector and tumor target cells were co-cultured in triplicates at the indicated effector/target ratio in black-walled 96-well plate. $5\times10^4$ target cells were seeded in a total volume of 100 μL per well with X-VIVO15 supplemented with 5% of human AB Serum (Gemini), 10 U/ml IL7, and 10 U/mL IL15 (PeproTech, Inc). Target cell alone plated at the same cell density was used to determine maximum luciferase expression (relative light units (RLU)). 100 μL luciferase substrate (Bright-Glo; Promega) was directly added to each well 18 hrs post-co-culture. Emitted light was determined using a luminescence plate reader. Tumor cell lysis was calculated as (1−(RLUsample)/(RLU-max))×100.

Isolation, Transduction, and Expansion of Genetically Modified Human T Cells

Buffy coats from de-identified healthy donors were purchased from the New York Blood Center (exempted from Institutional Review Board). All blood samples were handled in compliance with the required ethical and safety procedures. Isolation of peripheral blood mononuclear cells was carried out by density gradient centrifugation and activated with Dynabeads® ClinExVivo™ CD3/CD28 antibodies beads before transduction with γ-retroviral vector by centrifugation on RetroNectin-coated plates (Takara) as described previously (Zhao et al., *Cancer Cell* (2015); 28:415-428). After two days, the activated T cells were debeaded and transduced by spinoculation, as previously described (Hollyman et al., J. Immunotherapy (2009); 32(2): 160-180). Then, the transduced cells were expanded in a G-Rex 6M-well plate as per the manufacture's instruction (Wilson Wolf Corporation). Transduction efficiency was determined 5 days posttransduction. The CAR-T cells were used fresh or thawed from cryopreserved in 50% CS10 and 5% HSA in Plasmalyte.

Mouse Systemic Tumor Model 6- to 12-week-old NOD/SCID/IL-2Rγnull male mice were used under a protocol approved by the Memorial Sloan Kettering Cancer Center (MSKCC) Institutional Animal Care and Use Committee. All relevant animal use guidelines and ethical regulations were followed. In general, mice were inoculated with $0.5 \times 10^6$ NALM6 (CD19$^+$ wt or low expression)-FFLuc-GFP tumor cells through tail vein injection, followed by treatment of a specific dose CAR-T cells per mouse 4 days after tumor injection. NALM6 cells provided even tumor burdens, and no mice were excluded prior to CAR-T cell treatment. No randomization or blinding methods were used.

Bioluminescent Imaging

Tumor burden was evaluated as previously described (Gade et al., Cancer Research (2005); 65(16):9080-9088). Briefly, mice that were under 2% isoflurane anesthesia for 10 minutes were intraperitoneally injected with D-luciferin (Xenogen, 3 mg per mouse) resuspended in PBS and imaged. IVIS Imaging System (PerkinElmer) was used to image the bioluminescence of the injected tumor. Data were analyzed using the Living Image software (PerkinElmer).

Antibodies Used in Flow Cytometry

The expression of the surface markers from CAR T cells generated ex vivo or isolated from mouse bone marrow and spleen after 17 days of $1 \times 10^6$ CAR T treatments were detected using the following fluorophore-conjugated antibodies: APC-Cy7 anti-human CD8 (SK1), APC-Cy7 mouse anti-human CD45 (2D1), BUV395 mouse anti-human CD4 (SK3), BV421 mouse anti-human CD62L (DREG-56), BV650 mouse anti-human CD45RA (HI100), BV480 or BV510 mouse anti-human PD-1 (EH12.1) and BUV737 mouse anti-human CD19 (SJ25C1) (BD Bioscience); PE-Cy7 anti-human CD8 (SK1) and PerCP-eFluor 710 anti-human LAG-3 (3DS223H) (eBioscience); PerCP anti-human CD45RA (HI100), Brilliant Violet 785 anti-human Tim-3 (F38-2E2) and PE anti-human CD127 (IL7Ra) (Biolegend). The expression of the 1928z CAR was detected by using Alexa Fluor 647 goat anti-mouse AffiniPure IgG, F(ab')$_2$ fragment. To detect #2 CAR (represented as "19(T2) 28z1XX CAR"), Alexa Fluor 647-goat anti-human IgG, F(ab')2 fragment was used. 7-AAD (Beckman Coulter) was used as a viability dye. Flow cytometry was performed on a Cytek Aurora instrument (Cytek Biosciences). Data were analyzed with FlowJo software v.10.1 (FlowJo LLC).

Statistical Analyses

All statistical analyses were performed using Prism 8 (GraphPad) software. Statistical comparisons between two groups were determined by two-tailed unpaired t-test. For in vivo studies, the overall survival was presented using a Kaplan-Meier curve. Statistical significance is defined as a p-value <0.05.

Example 7—Toxicity Assessment

Summary

The toxicity of #2 CAR T cells (represented as "19(T2) 28z1XX CAR T cells") was assessed in vivo in NSG mice bearing NALM6 leukemia. Mice injected i.v. with 1928z CAR T cells at the same doses served as controls. The recorded parameters included whole body weight, tumor burden, and survival for all mice. More extensive toxicology investigation focused on mice treated at the highest dose ($1 \times 10^6$ CAR T cells/recipient), a dose that exceeds the minimum therapeutic (curative) dose in this mouse model (10x) and also exceeds the CAR T cell doses used clinically in proportion to recipient body weight (10-100x). These studies included enumeration and phenotyping of T cells at the main tumor site (bone marrow), serum cytokine measurements (both human, i.e., T cell-derived, and murine, i.e., host-derived), basic serum biochemistry including liver enzymes, peripheral blood cell counts and organ weights and comprehensive tissue immuno-histochemistry at the end of study (Days 27-28). The infused CAR T cells were produced in clinically relevant fashion and comparable between the two CAR T cell products.

Whole-body weights and survival did not significantly differ between the test and control group. Serum cytokine levels were also comparable and did not suggest the occurrence of CRS in either group. ALT and AST enzyme levels were comparable between both study groups on day10. The enzyme levels of mice treated with #2 CAR T cells (represented as "19(T2)28z1XX CAR T cells") were lower than mice treated with 1928z CAR T cells on day 27/28.

As anticipated, #2 CAR T cells (represented as "19(T2) 28z1XX CAR T cells") outlasted 1928z CAR T cells. Mice in the #2 CAR T cells (represented as "19(T2)28z1XX CAR T cells") treated group had higher lymphocytes and reticulocyte counts than the 1928z CAR T cell group. Mice that received 1928z CAR T cells showed diffuse tumor infiltrates but not recipients of #2 CAR T cells (represented as "19 (T2)28z1XX CAR T cells"). Mice with persisting #2 CAR T cells (represented as "19(T2)28z1XX CAR T cells") showed mild to moderate xenogeneic GVHD and hepatocellular necrosis.

Whereas the GVHD is to be expected in NSG mice treated with a high dose of human CAR T cells, the latter's mechanism is uncertain. Given the xenogeneic nature of the study (prone to xenoreactivity of human T cells against mouse tissues) and its conduct using a single donor (unknown underlying T cell receptor repertoire), the significance of this adverse event for an autologous therapy in humans is uncertain.

Justification of Animal Model

The NALM6 model in NSG mice has been extensively used to assess the activity of CD19-specific CAR T cells in the Sadelain laboratory (Zhao et al., Cancer Cell (2015); 28:415-428, Feucht, et al. Nature Medicine (2019); 25(1): 82-88, Hamieh et al., Nature (2019); 568(7750):112-116, Eyquem et al., Nature (2017); 543(7643):113-117) and others. NALM6 is a human pre-B acute lymphocytic leukemia (ALL) that expresses CD19, but neither CD80, CD86, 4-1BBL, or other major costimulatory ligands.

Justification of Dose and Schedule

A single intravenous injection of $1 \times 10^6$ viable CAR T cells, which was based on transduction efficiency and total viable cells, was the selected dose given that it corresponds to 10x the minimum effective treatment ($1 \times 10^5$ CAR T cells) in this animal model (see FIG. 15). The CAR T cell dosage is approximately 10-100x higher than the approved CD19 CAR T cell doses for adults (e.g., approved dose of 0.1-$1.5 \times 10^8$ viable CART cells) when converted by bodyweight from mouse to human. The proposed starting flat-dose in the human clinical trial protocol for #2 CAR T cells is $25 \times 10^6$ CAR T cells.

Methods

Test Article and Vehicle

The test article is 1928z CAR T cells, #2 CAR T cells (represented as "19(T2)28z1XX CAR T cells" in this Example), and untransduced T cells prepared by Cell Therapy and Cell Engineering Facility (CTCEF) at MSKCC. The cells were frozen in liquid nitrogen until the start of the study. On the day of T cell injection, cells were thawed at 37° C. and washed with 1% HSA in Plasmalyte. Cells were then formulated into doses of $1\times10^6$, $5\times10^5$, $2\times10^5$, and $1\times10^5$ CAR-T cells in a volume of 200 μL per mice using 1% HSA in Plasmalyte. The numbers of CAR T cells were determined by multiplying the total cell numbers by the CAR' percentage, which has been predetermined using flow cytometry.

Test System

Experiments were conducted using 6- to 12-week-old NOD/SCID/IL-2Rγnull male mice injected with $0.5\times10^6$ FFLuc-GFP NALM6 cancer cells. Thawed cryopreserved $1\times10^6$ CD4/CD8 selected T cells transduced a γ-retroviral vector for either 1928z CAR or #2 CAR (represented as "19(T2)28z1XX CAR") were infused into the mice four days after the injection of the tumor cells. Untreated mice were expected to develop hindlimb paralysis due to bone marrow-infiltrating leukemia by Day 16-18.

Wild type NALM6 human tumor cell line is a well-characterized model for pre-B acute lymphoblastic leukemia, which the Sadelain laboratory has used in numerous peer-reviewed publications (Zhao et al., *Cancer Cell* (2015); 28:415-428, Feucht, et al. *Nature Medicine* (2019); 25(1): 82-88, Hamieh et al., *Nature* (2019); 568(7750):112-116, Eyquem et al., *Nature* (2017); 543(7643):113-117).

Study Design

115 Mice were divided into 1928z CAR, #2 CAR (represented as "19(T2)28z1XX CAR"), and untransduced groups. All mice received $0.5\times10^6$ FFLuc-GFP NALM6 tumor cells via tail vein injection 4 days prior to T cell treatment. On Study Day 0, mice were assigned into treatment groups. Each group received one single dose (200 μl) of the test article via intravenous administration. The group assignments are outlined in Table 3.

TABLE 3

| | | | | | | | |
|---|---|---|---|---|---|---|---|
| Experimental design and group assignments | | | | | | | |
| Group number | CAR T dose (×10⁶) | Number of mice/ Group | Sex | Mice ID# | BLI* | Blood/Tissue Collection | Complete Necropsy |
| Blood Collection at Day 10 and Day 27 (or 28) and Final Sacrifice at Day 27 (or 28) | | | | | | | |
| 1. NALM6 + 1928z CAR T cells | 1.0 | 10 | M | 6-15 | Imaged | Whole Blood (day 10 and day 27/28) CBC/Chem | Day 27/28 |
| 2. NALM6 + 19(T2)28z1XX CAR T cells | 1.0 | 10 | M | 66-75 | Imaged | Whole Blood (day 10 and day 27/28) CBC/Chem | Day 27/28 |
| Interim Sacrifice at Day 17 | | | | | | | |
| 3. NALM6 + 1928z CAR T cells | 1.0 | 5 | M | 21-25 | Imaged | Bone Marrow | No |
| 4. NALM6 + 19(T2)28z1XX CAR T cells | 1.0 | 5 | M | 76-80 | Imaged | Bone Marrow | No |
| Imaging every 7 days | | | | | | | |
| 5. NALM6 + UNTRANSDUCED T cells | 1.0‡ | 5 | M | 1-5 | Imaged | None | No |
| 6. NALM6 + 1928z CAR T cells | 1.0 | 10 | M | 16-20 26-30 | Imaged | None | No |
| 7. NALM6 + 1928z CAR T cells | 0.5 | 10 | M | 31-40 | Imaged | None | No |
| 8. NALM6 + 1928z CAR T cells | 0.2 | 10 | M | 41-50 | Imaged | None | No |
| 9. NALM6 + 1928z CAR T cells | 0.1 | 10 | M | 51-60 | Imaged | None | No |
| 10. NALM6 + 19(T)28z1XX CAR T cells | 1.0 | 10 | M | 61-65 81-85 | Imaged | None | No |
| 11. NALM6 + 19(T)28z1XX CAR T cells | 0.5 | 10 | M | 86-95 | Imaged | None | No |
| 12. NALM6 + 19(T)28z1XX CAR T cells | 0.2 | 10 | M | 96-105 | Imaged | None | No |
| 13. NALM6 + 19(T)28z1XX CAR T cells | 0.1 | 10 | M | 106-115 | Imaged | None | No |

*BLI—bioluminescence imaging once every week starting at Day 0 (infusion of the CAR T cells)
‡Untransduced CD4/CD8 T cells.
‡‡ All mice were weighed on day 7, day 11, day 21, and day 27 until the animal's interim or final sacrifice.

Toxicology Parameters

Toxicity was monitored by changes in body weights following test article administration. After 10 days and 28 days of test article administration, blood samples from the $1\times10^6$ dose groups of 1928z CART cells and #2 CART cells (represented as "19(T2)28z1XX CAR T cells") were collected from the orbital venous plexus following anesthesia under 2% isoflurane. Blood samples were collected into tubes containing a serum separator and were used for measuring the levels of cytokines and liver enzymes. On day 27 and day 28, mice from the $1\times10^6$ dose groups of 1928z CAR and #2 CAR (represented as "19(T2)28z1XX CAR") were submitted for full necropsy analyses on each indicated day.

Cytokine Analysis

Sera were collected from mice on day 10 and day 28 post CAR T treatment from both 1928z CAR and #2 CAR (represented as "19(T2)28z1XX CAR") groups that received the $1\times10^6$ CAR T cells dose. The samples were stored at $-80°$ C. until analysis. ProcartaPlex assay was used to quantify the levels of mouse cytokines (MCP-1, IL-6, and G-CSF) and human cytokines (IL2, IL3, IFN-g, GM-CSF, Granzyme B, and TNF-a). All ProcartaPlex related reagents in this study were purchased from ThermoFisher Scientific. Serum collected from a mouse model with severe cytokine release syndrome were used as positive controls (Giavridis et al., Nature Medicine (2018); 24(6):731-738). 60 μL of beads from the simplex kits of individual cytokines were pooled, and 50 μL of bead mixtures were dispensed into each well of a 96-well plate according to manufacturer's protocol. Standards, quality controls, and samples diluted 1:4 using Universal Assay Buffer were added to the wells. The plates were sealed, shaken at 500 rpm for 30 minutes at room temperature, and transferred to 4° C. After overnight incubation, the plates were shaken for an additional 30 minutes at room temperature at 500 rpm. Plates were washed, and the detection antibody was added to each well. The plates were sealed and shaken at 500 rpm for 30 minutes at room temperature. After washing, a Streptavidin RPE solution was added to each well. The plates were sealed and shaken at 500 rpm for 30 minutes at room temperature. After a final wash step, the beads were resuspended in reading buffer and the assay signals acquired on a Luminex 200 instrument. Standard curves for individual cytokines were generated using a 5-parameter logistic equation, and the concentration of individual cytokines in each sample was calculated by the xPONENT software (version 4.2.1509.0).

Statistics

All statistical analyses were done using Prism 8 (GraphPad) software. Statistical comparisons between two groups were determined by two-tailed unpaired t-test. Statistical significance was defined as a p-value <0.05.

Results

Changes in mice bodyweight during 1928z CAR T cells and #2 CAR T cells (represented as "19(T2)28z1XX CAR T cells") treatments were measured. NALM6 tumor-bearing mice were treated with $1\times10^6$, $5\times10^5$, $2\times10^5$, or $1\times10^5$ of 1928z CART cells or #2 CART cells (represented as "19(T2)28z1XX CAR T cells") (n=10 per group), whereas untransduced T cell treatment served as the control group (n=5). The results are shown in FIG. 18. As shown in FIG. 18, the change of body weight between the two CAR T cell treatments was similar.

Next, liver enzymes in serum of mice treated with #2 CAR T cells (represented as "19(T2)28z1XX CAR T cells") and 1928z CAR T cells were measured. Quantification of liver enzyme levels from the two CAR T treated mice on day 10 and day 27/28 (dose level=$1\times10^6$ CAR T, n=10 per group) is presented in FIG. 19. NALM6 tumor-bearing mice were treated with $1\times10^6$ of 1928z CAR T cells or #2 CAR T cells (represented as "19(T2)28z1XX CAR T cells") were evaluated for ALT and AST levels on Day 10 and Day 27/28. As shown in FIG. 19, ALT and AST enzyme levels were comparable between both study groups on day10. The enzyme levels of mice treated with #2 CAR T cells (represented as "19(T2)28z1XX CAR T cells") were lower than mice treated with 1928z CAR T cells on day 27/28.

Human and mouse cytokine levels in mice treated with $1\times10^{6\ \#2}$ CAR T cells (represented as "19(T2)28z1XX CAR T cells") or 1928z CART cells on day 10 and day 27/29 post-infusion were measured. FIG. 20 shows the quantification of human cytokine levels from sera obtained from two groups of different CAR T treated mice on day 10 and day 27/28 (dose level=1×106 CAR T, n=10 per group). Sera collected from a mouse model with severe cytokine release syndrome were used as positive controls (n=2) (Giavridis et al., Nature Medicine (2018); 24(6):731-738). IL2, IL3, GM-CSF, Granzyme B, and TNF alpha levels are comparable between two CAR T cell groups on day10 and day 27/28. IFN-γ level from 19(T2)28z1XX CAR T treated group was higher than the levels in mice that received 1928z CAR T cells on day 27/28.

FIG. 21 shows the results of the quantification of mouse cytokine levels from mice sera treated with either 1928z CAR T cells or #2 CAR T cells (represented as "19(T2)28z1XX CAR T cells") (dose level=$1\times10^6$ CAR T, n=10 per group) on day 10 and day 27/28. Sera collected from a mouse model with severe cytokine release syndrome was used as positive controls (n=2) (Giavridis et al., Nature Medicine (2018); 24(6):731-738). On day10, mice treated with #2 CAR T cells (represented as "19(T2)28z1XX CAR T cells") had slightly higher levels of MCP-1 and G-CSF than mice infused with 1928z CAR T cells, whereas IL6 level was comparable for both CAR T cell groups. On day27/28, mice treated with #2 CAR T cells (represented as "19(T2)28z1XX CAR T cells") had similar levels of MCP-1, IL-6, and G-CSF as the levels in the 1928z CAR T group. These observations suggest that there was no evidence of cytokine release syndrome (CRS) in either group.

Blood cell counts of mice treated with #2 CAR T cells (represented as "19(T2)28z1XX CAR T cells") and 1928z CAR T cells at day 27/28 post-infusion were measured. Quantification of essential blood cells from two different CAR T treatment groups on day 27/28 (dose level=$1\times10^6$ CAR T, n=10 per group) is presented in FIG. 22. Comparisons of neutrophil, lymphocyte, and monocyte counts, and reticulocyte counts are shown. As shown in FIG. 22, neutrophil and monocytes were comparable between the two CAR T groups ($1\times10^6$ dose level). The mice in the 19(T2)28z1XX CAR T cell treated group had higher lymphocytes and reticulocyte counts than the 1928z CAR T cell group.

In addition, body and organ weights of mice treated with #2 CAR T cells (represented as "19(T2)28z1XX CAR T cells") and 1928z CAR T cells at necropsy were measured. Comparison of body and essential organ weights from two different CAR T treatment groups on day 27/28 (dose level=$1\times10^6$ CAR T). The results are shown in FIG. 23. As shown in FIG. 23, bodyweight, spleen, and kidney weights were comparable between the two treatment Groups 1 and 2. The mice in 19(T2)28z1XX CAR T treated group (labeled "SFG-19(T2)28z-1XX") had lighter liver weight than the mice in the 1928z CAR T group (labeled "SFG-1928z"). The differences in the heart weight were ascribed to uneven technical handling.

CD3$^+$ and CD19$^+$ immunohistochemistry of liver, bone marrow, and spleen of mice treated with #2 CAR T cells (represented as "19(T2)28z1XX CAR T cells") and 1928z CAR T cells was measured. Evaluations of lymphocytes and tumor infiltration levels in liver, spleen, and bone marrow from mice on 27/28 days post CAR T treatment (dose level=1×10$^6$CAR T, n=6) are presented in FIG. 24. As shown in FIG. 24, the mice in 19(T2)28z1XX CAR T treatment group (labeled "SFG-19(T2)28z-1XX") had a higher level of CD3$^+$ cells in all evaluated organs than the animals treated with 1928z CAR T cells (labeled "SFG-1928z"). Tumor infiltration was observed in all tested organs from 1928z CAR T group, but not in 19(T2)28z1XX CAR T group.

Conclusions

The toxicity profile of #2 CAR T cells (represented as "19(T2)28z1XX CAR T cells") was compared to that of 1928z CAR T cells at the high dose of 1×10$^6$ CAR T cells per recipient. No difference in whole-body weight or survival was found. Serum cytokine levels measured on day 10 were comparable between the two groups, suggesting that #2 CAR T cells (represented as "19(T2)28z1XX CAR T cells") were not more likely than 1928z CAR T cells to induce a cytokine release syndrome (CRS). Hepatic enzymes were elevated in both groups on days and 17, but less so in recipients of #2 CAR T cells (represented as "19(T2)28z1XX CAR T cells") than in those given 1928z CAR T cells. Peripheral blood cell counts showed higher lymphocyte counts in recipients of #2 CAR T cells (represented as "19(T2)28z1XX CAR T cells"), consistent with the latter's greater persistence documented by FACs analysis (Day 17) and tissue IHC (Days 27/28). An isolated reticulocytosis was observed, without anemia, polycythemia or erythroid hyperplasia, which is therefore not regarded as an adverse event.

Organ weights were similar between the two groups, except for liver, which was heavier in mice treated with 1928z CAR T cells, owing to substantial tumor progression (BLI and IHC). In contrast, mice treated with #2 CAR T cells (represented as "19(T2)28z1XX CAR T cells") showed the absence of tumors by IHC, corroborating the BLI findings in these same mice. Multi-organ lymphocytic infiltrates were observed in the #2 CAR T cells (represented as "19(T2)28z1XX CAR T cells") recipient mice, consistent with xenogeneic GVHD. The latter was corroborated by the finding of epithelial necrosis in those tissues. Mild to moderate hepatocellular necrosis was also observed in #2 CAR T cells (represented as "19(T2)28z1XX CART cells") infused mice. This microscopic finding is not typically associated with GVHD and thus represents a possible adverse event. Its impact on liver function is limited given the modest elevation of liver enzymes (AST only, not ALT) and the normal bilirubin values. Other pathology findings were minor, equally represented between the two treatment groups, and thus were not deemed to represent significant findings. T cell flow cytometry profiles were similar between the two treatment groups, consistent with the expected finding that #2 CAR T cells (represented as "19(T2)28z1XX CAR T cells") show increased therapeutic potency owing to the greater persistence of CAR T cells.

The toxicity studies, assessing #2 CAR T cells (represented as "19(T2)28z1XX CAR T cells") in comparison to the clinically tested 1928z CAR T cells (Park et al., N. Engl. J. Med. (2018); 378(5):449-459), uncovered mild to moderate GVHD as well as mild to moderate hepatocellular necrosis in mice treated with #2 CAR T cells (represented as "19(T2)28z1XX CAR T cells").

It is concluded from the data shown in this Example and Example 6 that #2 CAR T cells (represented as "19(T2)28z1XX CAR T cells") are more potent, owing to their greater persistence relative to 1928z CAR T cells, but without posing greater risks. The relatively increased potency of #2 CAR T cells (represented as "19(T2)28z1XX CAR T cells") supports a human clinical trial design starting with the dose of 25×10$^6$ CAR T cells, a relatively low dose in comparison to most CAR T cell trials targeting CD19.

Example 8—Pharmacology Studies

On-Cell Binding of Anti-CD19 Antibodies

The on-cell binding for the anti-CD19 antibodies comprising the $V_H$ and $V_L$ of the presently disclosed scFvs were assessed by flow cytometry on the endogenous CD19 expressing Raji and NALM-6 cell lines. Each antibody was tested on both the CD19 positive parental lines and corresponding CD19 knock-out Raji and NALM-6 lines to confirm on-cell target specific binding. The flow cytometry chromatograms shown in FIG. 25 demonstrate 1-2 log shifts on the CD19 positive lines over the background binding on the corresponding knockout cell lines.

The serial dilution flow cytometry results shown in FIG. 26A-26C demonstrate saturation binding on NALM-6 cells. The EC50 values calculated from the curves, are provided in Table 4. Exemplary anti-CD19 antibodies bind CD19 positive NALM-6 cells at high affinities from of at least 0.2 nM. The higher affinities observed on CD19 positive cells versus the soluble protein suggests that these antibodies bind an epitope that may be more natively presented on cells than in the CD19-HSA fusion protein. All the anti-CD19 antibodies shown in Table 4 comprise a $V_H$ comprising the amino acid sequence set forth in SEQ ID NO: 10.

TABLE 4

| EC50 of anti-CD19 antibodies on NALM6 cells | | |
|---|---|---|
| CD19 Antibody | SEQ ID NO. of the $V_L$ amino acid sequence | NALM-6 on-cell binding affinity EC50 (nM) |
| Antibody 2 | 14 | 0.3136 |
| Antibody 4 | 58 | 0.5195 |
| Antibody 5 | 60 | 0.2192 |
| Antibody 8 | 18 | 0.2097 |
| Antibody 6 | 62 | 0.1798 |
| Antibody 7 | 64 | 0.2104 |
| Antibody 1 | 67 | 0.5879 |
| Antibody 15 | 1 | 0.2698 |

Example 9—Phase I Study of CD19-Targeted 19(T2)28z1XX CAR T Cells in Adult Patients with Relapsed or Refractory B-Cell Malignancies This Example describes a Phase I Study of CD19-Targeted 19(T2)28z1XX CAR T Cells in Adult Patients with Relapsed or Refractory B-Cell Malignancies. "19(T2) 28z1XX" and "19(T2)28z1XX" are used Interchangeably herein. Autologous CAR T cell therapy targeting the B-cell specific surface antigen CD19 has demonstrated favorable clinical responses in relapsed or refractory (R/R) B-cell lymphomas (BCL). However, despite 40-60% initial complete response (CR) rates, only a subset of patients experiences durable remissions, and there is a need to further improve the efficacy of CAR therapies by preventing relapse and attaining a deeper clinical response (CR).

Study Design and Methods: This study is a single center Phase I clinical trial of 19(T2)28z1XX in patients with R/R B-cell malignancies. Key disease eligibility criteria include R/R diffuse large B cell lymphoma (DLBCL), high grade BCL, primary mediastinal BCL, indolent BCL and chronic lymphocytic leukemia (CLL). Patients with prior CD19 CAR therapies are eligible as long as expression of CD19 is confirmed. Key exclusion criteria include ongoing immunosuppression such as systemic GvHD therapy and active CNS disease.

The study uses a 3+3 dose-escalation design to identify the maximum tolerated dose for BCL. There are 5 planned flat-dose levels: $25\times10^6$, $50\times10^6$, $100\times10^6$, $150\times10^6$, and $200\times10^6$ CAR T cells. Patients receive conditioning chemotherapy consisting of 3 days of fludarabine and cyclophosphamide followed by a single infusion of 19(T2)28z1XX CAR T cells. In the dose-escalation phase, patients with DLBCL, high grade BCL, and primary mediastinal BCL are eligible to participate. Once the recommended phase 2 dose (RP2D) is determined, the study is open to dose expansion phase with two cohorts. Cohort 1 includes DLBCL, high grade BCL and primary mediastinal BCL (i.e. same eligibility criteria as the dose-escalation phase). Cohort 2 includes patients with indolent BCL, CLL, and Richter's transformation. The dose-expansion part of the trial is designed to further characterize the safety, efficacy, and pharmacokinetics of 19(T2)28z1XX CAR in multiple indications. Up to a maximum of 60 patients are enrolled.

The primary objective of the trial is to evaluate safety and tolerability and determine the recommended Phase 2 dose of 19(T2)28z1XX. Key secondary objectives include evaluation of the efficacy and pharmacokinetics of 19(T2)28z1XX. Exploratory objectives include assessment of B cell aplasia and measurable residual disease (MRD), characterization of 19(T2)28z1XX CAR T cell phenotypes pre- and post-infusion, and analysis of serum cytokines.

Although the presently disclosed subject matter and certain of its advantages have been described in detail, it should be understood that various changes, substitutions and alterations can be made herein without departing from the spirit and scope of the disclosure. Moreover, the scope of the present application is not intended to be limited to the particular embodiments of the process, machine, manufacture, and composition of matter, and methods described in the specification. As one of ordinary skill in the art will readily appreciate from the disclosure of the presently disclosed subject matter, processes, machines, manufacture, compositions of matter, or methods, presently existing or later to be developed that perform substantially the same function or achieve substantially the same result as the corresponding embodiments described herein may be utilized according to the presently disclosed subject matter. Accordingly, the appended claims are intended to include within their scope such processes, machines, manufacture, compositions of matter, or methods.

Various patents, patent applications, publications, product descriptions, protocols, and sequence accession numbers are cited throughout this application, the disclosure of which are incorporated herein by reference in their entireties for all purposes.

What is claimed is:

1. A chimeric antigen receptor (CAR), comprising an extracellular antigen-binding domain that specifically binds to CD19, a transmembrane domain, and an intracellular signaling domain, wherein the extracellular antigen-binding domain comprises:
   a) a heavy chain variable region comprising a CDR1 comprising the amino acid sequence set forth in SEQ ID NO: 7, a CDR2 comprising the amino acid sequence set forth in SEQ ID NO: 8, and a CDR3 comprising the amino acid sequence set forth in SEQ ID NO: 9; and
   b) a light chain variable region comprising:
      i) a CDR1 comprising the amino acid sequence set forth in SEQ ID NO: 11, a CDR2 comprising the amino acid sequence set forth in SEQ ID NO: 12, and a CDR3 comprising the amino acid sequence set forth in SEQ ID NO: 13.

2. The CAR of claim 1, wherein the extracellular antigen-binding domain comprises a single-chain variable fragment (scFv), a Fab, or a F(ab)2.

3. The CAR of claim 1, wherein the heavy chain variable region comprises an amino acid sequence that is at least about 80% identical to the amino acid sequence set forth in SEQ ID NO: 10.

4. The CAR of claim 1, wherein the heavy chain variable region comprises the amino acid sequence set forth in SEQ ID NO: 10.

5. The CAR of claim 1, wherein the light chain variable region comprises an amino acid sequence that is at least about 80% identical to the amino acid sequence set forth in SEQ ID NO: 14.

6. The CAR of claim 1, wherein the light chain variable region comprises the amino acid sequence set forth in SEQ ID NO: 14.

7. The CAR of claim 1, wherein the heavy chain variable region comprises the amino acid sequence set forth in SEQ ID NO: 10; and the light chain variable region comprises the amino acid sequence set forth in SEQ ID NO: 14.

8. The CAR of claim 1, wherein the extracellular antigen-binding domain comprises a linker between the heavy chain variable region and the light chain variable region.

9. The CAR of claim 8, wherein the linker consists of the amino acid sequence set forth in SEQ ID NO: 1, SEQ ID NO: 2, SEQ ID NO: 3, or SEQ ID NO: 4.

10. The CAR of claim 1, wherein the extracellular antigen-binding domain comprises or is a scFv, which comprises or consists of the amino acid sequence set forth in SEQ ID NO: 15.

11. The CAR of claim 1, wherein the transmembrane domain comprises a CD8 polypeptide, a CD28 polypeptide, a CD3ζ polypeptide, a CD4 polypeptide, a 4-1BB polypeptide, an OX40 polypeptide, an ICOS polypeptide, a CTLA-4 polypeptide, a PD-1 polypeptide, a LAG-3 polypeptide, a 2B4 polypeptide, or a BTLA polypeptide.

12. The CAR of claim 1, wherein the intracellular signaling domain comprises a CD3ζ polypeptide or a modified CD3ζ polypeptide.

13. The CAR of claim 12, wherein the modified CD3ζ polypeptide comprises a native ITAM1, an ITAM2 variant consisting of two loss-of-function mutations, and an ITAM3 consisting of two loss-of-function mutations.

14. The CAR of claim 13, wherein
   a) the native ITAM1 consists of the amino acid sequence set forth in SEQ ID NO: 31;
   b) the ITAM2 variant consists of the amino acid sequence set forth in SEQ ID NO: 37;
   c) the ITAM3 variant consists of the amino acid sequence set forth in SEQ ID NO: 41.

15. The CAR of claim 12, wherein the modified CD3ζ polypeptide comprises or consists of the amino acid sequence set forth in SEQ ID NO: 43.

16. The CAR of claim 1, wherein the intracellular signaling domain further comprises at least one co-stimulatory signaling region.

17. The CAR of claim 16, wherein the at least one co-stimulatory signaling region comprises a CD28 polypeptide, a 4-1BB polypeptide, an OX40 polypeptide, an ICOS polypeptide, a DAP-10 polypeptide, or a combination thereof.

18. A cell comprising the CAR of claim 1.

19. The cell of claim 18, wherein the cell is transduced with the CAR.

20. The cell of claim 18, wherein the CAR is constitutively expressed on the surface of the cell.

21. The cell of claim 18, wherein the cell is an immuno-responsive cell.

22. The cell of claim 18, wherein the cell is a cell of the lymphoid lineage or a cell of the myeloid lineage.

23. The cell of claim 18, wherein the cell is selected from the group consisting of a T cell, a Natural Killer (NK) cell, a stem cell from which lymphoid cells may be differentiated, and a stem cell from which myeloid cells may be differentiated.

24. The cell of claim 23, wherein the NK cell is derived from a stem cell.

25. The cell of claim 24, wherein the stem cell is an embryoid stem cell or an induced pluripotent stem cell.

26. The cell of claim 18, wherein the cell is a T cell.

27. The cell of claim 26, wherein the T cell is selected from the group consisting of helper T cells, cytotoxic T cells, memory T cells, regulatory T cells, tumor-infiltrating lymphocyte (TIL), Natural Killer T cells, mucosal associated invariant T cells, and γδ T cells.

28. A composition comprising the cell of claim 18.

29. The composition of claim 28, which is a pharmaceutical composition further comprising a pharmaceutically acceptable carrier.

30. The composition of claim 28, comprising
   a) between about 1×10⁶ and about 5×10⁸ cells;
   b) between about 1×10⁶ and about 1×10⁸ cells;
   c) between about 1×10⁶ and about 5×10⁷ cells; or
   d) about 2.5×10⁷ cells.

31. A kit for reducing tumor burden in a subject, treating a neoplasm in a subject, and/or increasing or lengthening survival of a subject having a neoplasm, comprising the cell of claim 18.

32. A nucleic acid molecule encoding the CAR of claim 1.

33. The nucleic acid molecule of claim 32, further comprising a promoter that is operably linked to the CAR.

34. The nucleic acid molecule of claim 33, wherein the promoter is an endogenous promoter, an exogenous promoter, or an inducible promoter.

35. The nucleic acid molecule of claim 34, wherein a) the exogenous promoter is selected from the group consisting of an elongation factor (EF)-1 promoter, a cytomegalovirus immediate-early promoter (CMV) promoter, a simian virus 40 early promoter (SV40) promoter, a phosphoglycerate kinase (PGK) promoter, a metallothionein promoter, and Ubiquitin C promoter;

b) the inducible promoter is selected from the group consisting of a NFAT transcriptional response element (TRE) promoter, a CD69 promoter, a CD25 promoter, an IL-2 promoter, a 4-1BB promoter, a PD1 promoter, and a LAG3 promoter; and/or c) the endogenous promoter is selected from a TCR alpha promoter, a TCR beta promoter, and a beta 2-microglobulin promoter.

36. A vector comprising the nucleic acid molecule of claim 32.

37. A cell expressing the nucleic acid molecule of claim 32.

38. The cell of claim 37, wherein the cell is a T cell or a Natural Killer (NK) cell.

39. A method of reducing tumor burden in a subject, increasing or lengthening survival of a subject having a neoplasm, and/or treating a neoplasm in a subject, wherein the tumor and/or neoplasm is associated with CD19, the method comprising administering to the subject the cell of claim 18.

40. The method of claim 39, wherein the tumor and/or neoplasm is a blood cancer, a B cell malignancy, or a B cell lymphoma.

41. The method of claim 40, wherein the blood cancer is selected from the group consisting of multiple myeloma, leukemia, and lymphomas.

42. The method of claim 41, wherein a) the leukemia is selected from the group consisting of acute myeloid leukemia (AML), chronic myeloid leukemia (CML), acute lymphocytic leukemia (ALL), chronic lymphocytic leukemia (CLL), acute promyelocytic leukemia (APL), mixed-phenotype acute leukemia (MLL), hairy cell leukemia, and B cell prolymphocytic leukemia; or b) the lymphoma is Hodgkin's lymphoma or non-Hodgkin's lymphoma.

43. The method of claim 40, wherein the B cell malignancy is selected from the group consisting of B cell non-Hodgkin lymphomas (NHL), B cell Hodgkin's lymphomas, B cell acute lymphocytic leukemia (ALL), B cell chronic lymphocytic leukemia (CLL), multiple myeloma (MM), CLL with Richter's transformation, and CNS lymphoma.

44. The method of claim 40, wherein the B cell lymphoma is relapsed or refractory (R/R) B cell lymphoma.

45. The method of claim 39, wherein the subject is a human subject.

46. A method for producing a cell comprising the CAR of claim 1, comprising introducing into the cell a nucleic acid molecule that encodes the CAR of claim 1.

* * * * *

SEQUENCE LISTING

```
Sequence total quantity: 77
SEQ ID NO: 1            moltype = AA  length = 15
FEATURE                 Location/Qualifiers
REGION                  1..15
                        note = Synthetic
source                  1..15
                        mol_type = protein
                        organism = synthetic construct
SEQUENCE: 1
GGGGSGGGGS GGGGS                                                15

SEQ ID NO: 2            moltype = AA  length = 19
FEATURE                 Location/Qualifiers
REGION                  1..19
                        note = Synthetic
source                  1..19
                        mol_type = protein
                        organism = synthetic construct
SEQUENCE: 2
GGGGSGGGGS GGGSGGGGS                                            19

SEQ ID NO: 3            moltype = AA  length = 24
FEATURE                 Location/Qualifiers
REGION                  1..24
                        note = Synthetic
source                  1..24
                        mol_type = protein
                        organism = synthetic construct
SEQUENCE: 3
GGGGSGGGGS GGGGSGGGSG GGGS                                      24

SEQ ID NO: 4            moltype = AA  length = 29
FEATURE                 Location/Qualifiers
REGION                  1..29
                        note = Synthetic
source                  1..29
                        mol_type = protein
                        organism = synthetic construct
SEQUENCE: 4
GGGGSGGGGS GGGGSGGGGS GGGSGGGGS                                 29
```

```
SEQ ID NO: 5                 moltype = AA   length = 557
FEATURE                      Location/Qualifiers
source                       1..557
                             mol_type = protein
                             organism = Homo sapiens
SEQUENCE: 5
MPPPRLLFFL LFLTPMEVRP EEPLVVKVEE GDNAVLQCLK GTSDGPTQQL TWSRESPLKP    60
FLKLSLGLPG LGIHMRPLAI WLFIFNVSQQ MGGFYLCQPG PPSEKAWQPG WTVNVEGSGE   120
LFRWNVSDLG GLGCGLKNRS SEGPSSPSGK LMSPKLYVWA KDRPEIWEGE PPCLPPRDSL   180
NQSLSQDLTM APGSTWLSC GVPPDSVSRG PLSWTHVHPK GPKSLLSLEL KDDRPARDMW    240
VMETGLLLPR ATAQDAGKYY CHRGNLTMSF HLEITARPVL WHWLLRTGGW KVSAVTLAYL   300
IFCLCSLVGI LHLQRALVLR RKRKRMTDPT RRFFKVTPPP GSGPQNQYGN VLSLPTPTSG   360
LGRAQRWAAG LGGTAPSYGN PSSDVQADGA LGSRSPPGVG PEEEEGEGYE EPDSEEDSEF   420
YENDSNLGQD QLSQDGSGYE NPEDEPLGPE DEDSFSNAES YENEDEELTQ PVARTMDFLS   480
PHGSAWDPSR EATSLAGSQS YEDMRGILYA APQLRSIRGQ PGPNHEEDAD SYENMDNPDG   540
PDPAWGGGGR MGTWSTR                                                 557

SEQ ID NO: 6                 moltype = AA   length = 556
FEATURE                      Location/Qualifiers
source                       1..556
                             mol_type = protein
                             organism = Homo sapiens
SEQUENCE: 6
MPPPRLLFFL LFLTPMEVRP EEPLVVKVEE GDNAVLQCLK GTSDGPTQQL TWSRESPLKP    60
FLKLSLGLPG LGIHMRPLAI WLFIFNVSQQ MGGFYLCQPG PPSEKAWQPG WTVNVEGSGE   120
LFRWNVSDLG GLGCGLKNRS SEGPSSPSGK LMSPKLYVWA KDRPEIWEGE PPCLPPRDSL   180
NQSLSQDLTM APGSTWLSC GVPPDSVSRG PLSWTHVHPK GPKSLLSLEL KDDRPARDMW    240
VMETGLLLPR ATAQDAGKYY CHRGNLTMSF HLEITARPVL WHWLLRTGGW KVSAVTLAYL   300
IFCLCSLVGI LHLQRALVLR RKRKRMTDPT RRFFKVTPPP GSGPQNQYGN VLSLPTPTSG   360
LGRAQRWAAG LGGTAPSYGN PSSDVQADGA LGSRSPPGVG PEEEEGEGYE EPDSEEDSEF   420
YENDSNLGQD QLSQDGSGYE NPEDEPLGPE DEDSFSNAES YENEDEELTQ PVARTMDFLS   480
PHGSAWDPSR EATSLGSQSY EDMRGILYAA PQLRSIRGQP GPNHEEDADS YENMDNPDGP   540
DPAWGGGGRM GTWSTR                                                  556

SEQ ID NO: 7                 moltype = AA   length = 5
FEATURE                      Location/Qualifiers
REGION                       1..5
                             note = Synthetic
source                       1..5
                             mol_type = protein
                             organism = synthetic construct
SEQUENCE: 7
SYGMH                                                                5

SEQ ID NO: 8                 moltype = AA   length = 17
FEATURE                      Location/Qualifiers
REGION                       1..17
                             note = Synthetic
source                       1..17
                             mol_type = protein
                             organism = synthetic construct
SEQUENCE: 8
LIWYDGSNKY YADSVKG                                                  17

SEQ ID NO: 9                 moltype = AA   length = 11
FEATURE                      Location/Qualifiers
REGION                       1..11
                             note = Synthetic
source                       1..11
                             mol_type = protein
                             organism = synthetic construct
SEQUENCE: 9
PVEGLLRGFD Y                                                        11

SEQ ID NO: 10                moltype = AA   length = 120
FEATURE                      Location/Qualifiers
REGION                       1..120
                             note = Synthetic
source                       1..120
                             mol_type = protein
                             organism = synthetic construct
SEQUENCE: 10
QVQLVESGGG VVQPGRSLRL SCAASGFTFS SYGMHWVRQA PGKGLEWVAL IWYDGSNKYY    60
ADSVKGRFTI SRDNSKNTLY LQMNSLRAED TAVYYCAKPV EGLLRGFDYW GQGTLVTVSS   120

SEQ ID NO: 11                moltype = AA   length = 12
FEATURE                      Location/Qualifiers
REGION                       1..12
```

```
                                note = Synthetic
source                          1..12
                                mol_type = protein
                                organism = synthetic construct
SEQUENCE: 11
RASQSVSSSY LA                                                                  12

SEQ ID NO: 12        moltype = AA   length = 7
FEATURE              Location/Qualifiers
REGION               1..7
                     note = Synthetic
source               1..7
                     mol_type = protein
                     organism = synthetic construct
SEQUENCE: 12
GASSRAT                                                                        7

SEQ ID NO: 13        moltype = AA   length = 9
FEATURE              Location/Qualifiers
REGION               1..9
                     note = Synthetic
source               1..9
                     mol_type = protein
                     organism = synthetic construct
SEQUENCE: 13
QQAGAVPIT                                                                      9

SEQ ID NO: 14        moltype = AA   length = 108
FEATURE              Location/Qualifiers
REGION               1..108
                     note = Synthetic
source               1..108
                     mol_type = protein
                     organism = synthetic construct
SEQUENCE: 14
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QAGAVPITFG GGTKVEIK                108

SEQ ID NO: 15        moltype = AA   length = 243
FEATURE              Location/Qualifiers
REGION               1..243
                     note = Synthetic
source               1..243
                     mol_type = protein
                     organism = synthetic construct
SEQUENCE: 15
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QAGAVPITFG GGTKVEIKGG GGSGGGGSGG   120
GGSQVQLVES GGGVVQPGRS LRLSCAASGF TFSSYGMHWV RQAPGKGLEW VALIWYDGSN   180
KYYADSVKGR FTISRDNSKN TLYLQMNSLR AEDTAVYYCA KPVEGLLRGF DYWGQGTLVT   240
VSS                                                                243

SEQ ID NO: 16        moltype = AA   length = 12
FEATURE              Location/Qualifiers
REGION               1..12
                     note = Synthetic
source               1..12
                     mol_type = protein
                     organism = synthetic construct
SEQUENCE: 16
RASQSVRSSY LA                                                                  12

SEQ ID NO: 17        moltype = AA   length = 9
FEATURE              Location/Qualifiers
REGION               1..9
                     note = Synthetic
source               1..9
                     mol_type = protein
                     organism = synthetic construct
SEQUENCE: 17
QQLFDSPYT                                                                      9

SEQ ID NO: 18        moltype = AA   length = 108
FEATURE              Location/Qualifiers
REGION               1..108
                     note = Synthetic
source               1..108
                     mol_type = protein
                     organism = synthetic construct
```

```
SEQUENCE: 18
EIVLTQSPGT LSLSPGERAT LSCRASQSVR SSYLAWYQQK PGQAPRLLIY GASSRATGIP  60
DRFSGSGSGT DFTLTISRLE PEDFAVYYCQ QLFDSPYTFG GGTKVEIK               108

SEQ ID NO: 19            moltype = AA  length = 242
FEATURE                  Location/Qualifiers
REGION                   1..242
                         note = Synthetic
source                   1..242
                         mol_type = protein
                         organism = synthetic construct
SEQUENCE: 19
IVLTQSPGTL SLSPGERATL SCRASQSVRS SYLAWYQQKP GQAPRLLIYG ASSRATGIPD  60
RFSGSGSGTD FTLTISRLEP EDFAVYYCQQ LFDSPYTFGG GTKVEIKGGG GSGGGGSGGG  120
GSQVQLVESG GGVVQPGRSL RLSCAASGFT FSSYGMHWVR QAPGKGLEWV ALIWYDGSNK  180
YYADSVKGRF TISRDNSKNT LYLQMNSLRA EDTAVYYCAK PVEGLLRGFD YWGQGTLVTV  240
SS                                                                242

SEQ ID NO: 20            moltype = AA  length = 7
FEATURE                  Location/Qualifiers
REGION                   1..7
                         note = Synthetic
source                   1..7
                         mol_type = protein
                         organism = synthetic construct
SEQUENCE: 20
GASRRAT                                                           7

SEQ ID NO: 21            moltype = AA  length = 9
FEATURE                  Location/Qualifiers
REGION                   1..9
                         note = Synthetic
source                   1..9
                         mol_type = protein
                         organism = synthetic construct
SEQUENCE: 21
QQAGIPPYT                                                         9

SEQ ID NO: 22            moltype = AA  length = 108
FEATURE                  Location/Qualifiers
REGION                   1..108
                         note = Sythetic
source                   1..108
                         mol_type = protein
                         organism = synthetic construct
SEQUENCE: 22
EIVLTQSPGT LSLSPGERAT LSCRASQSVS SSYLAWYQQK PGQAPRLLIY GASRRATGIP  60
DRFSGSGSGT DFTLTISRLE PEDFAVYYCQ QAGIPPYTFG GGTKVEIK               108

SEQ ID NO: 23            moltype = AA  length = 243
FEATURE                  Location/Qualifiers
REGION                   1..243
                         note = Synthetic
source                   1..243
                         mol_type = protein
                         organism = synthetic construct
SEQUENCE: 23
QVQLVESGGG VVQPGRSLRL SCAASGFTFS SYGMHWVRQA PGKGLEWVAL IWYDGSNKYY  60
ADSVKGRFTI SRDNSKNTLY LQMNSLRAED TAVYYCAKPV EGLLRGFDYW GQGTLVTVSS  120
GGGGSGGGGS GGGGSEIVLT QSPGTLSLSP GERATLSCRA SQSVSSSYLA WYQQKPGQAP  180
RLLIYGASRR ATGIPDRFSG SGSGTDFTLT ISRLEPEDFA VYYCQQAGIP PYTFGGGTKV  240
EIK                                                               243

SEQ ID NO: 24            moltype = AA  length = 220
FEATURE                  Location/Qualifiers
source                   1..220
                         mol_type = protein
                         organism = Homo sapiens
SEQUENCE: 24
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                       220

SEQ ID NO: 25            moltype = DNA  length = 78
FEATURE                  Location/Qualifiers
misc_feature             1..78
                         note = Synthetic
source                   1..78
```

```
                         mol_type = other DNA
                         organism = synthetic construct
SEQUENCE: 25
tgggtgctgg tggtggttgg tggagtcctg gcttgctata gcttgctagt aacagtggcc    60
tttattattt tctgggtg                                                  78

SEQ ID NO: 26              moltype = AA   length = 218
FEATURE                    Location/Qualifiers
source                     1..218
                           mol_type = protein
                           organism = Mus musculus
SEQUENCE: 26
MTLRLLFLAL NFFSVQVTEN KILVKQSPLL VVDSNEVSLS CRYSYNLLAK EFRASLYKGV     60
NSDVEVCVGN GNFTYQPQFR SNAEFNCDGD FDNETVTFRL WNLHVNHTDI YFCKIEFMYP    120
PPYLDNERSN GTIIHIKEKH LCHTQSSPKL FWALVVVAGV LFCYGLLVTV ALCVIWTNSR    180
RNRLLQSDYM NMTPRRPGLT RKPYQPYAPA RDFAAYRP                            218

SEQ ID NO: 27              moltype = AA   length = 235
FEATURE                    Location/Qualifiers
source                     1..235
                           mol_type = protein
                           organism = Homo sapiens
SEQUENCE: 27
MALPVTALLL PLALLLHAAR PSQFRVSPLD RTWNLGETVE LKCQVLLSNP TSGCSWLFQP     60
RGAAASPTFL LYLSQNKPKA AEGLDTQRFS GKRLGDTFVL TLSDFRRENE GYYFCSALSN    120
SIMYFSHFVP VFLPAKPTTT PAPRPPTPAP TIASQPLSLR PEACRPAAGG AVHTRGLDFA    180
CDIYIWAPLA GTCGVLLLSL VITLYCNHRN RRRVCKCPRP VVKSGDKPSL SARYV         235

SEQ ID NO: 28              moltype = AA   length = 247
FEATURE                    Location/Qualifiers
source                     1..247
                           mol_type = protein
                           organism = Mus musculus
SEQUENCE: 28
MASPLTRFLS LNLLLMGESI ILGSGEAKPQ APELRIFPKK MDAELGQKVD LVCEVLGSVS     60
QGCSWLFQNS SSKLPQPTFV VYMASSHNKI TWDEKLNSSK LFSAVRDTNN KYVLTLNKFS    120
KENEGYYFCS VISNSVMYFS SVVPVLQKVN STTTKPVLRT PSPVHPTGTS QPQRPEDCRP    180
RGSVKGTGLD FACDIYIWAP LAGICVAPLL SLIITLICYH RSRKRVCKCP RPLVRQEGKP    240
RPSEKIV                                                             247

SEQ ID NO: 29              moltype = AA   length = 164
FEATURE                    Location/Qualifiers
source                     1..164
                           mol_type = protein
                           organism = Homo sapiens
SEQUENCE: 29
MKWKALFTAA ILQAQLPITE AQSFGLLDPK LCYLLDGILF IYGVILTALF LRVKFSRSAD     60
APAYQQGQNQ LYNELNLGRR EEYDVLDKRR GRDPEMGGKP QRRKNPQEGL YNELQKDKMA    120
EAYSEIGMKG ERRRGKGHDG LYQGLSTATK DTYDALHMQA LPPR                     164

SEQ ID NO: 30              moltype = AA   length = 112
FEATURE                    Location/Qualifiers
REGION                     1..112
                           note = Synthetic
source                     1..112
                           mol_type = protein
                           organism = synthetic construct
SEQUENCE: 30
RVKFSRSADA PAYQQGQNQL YNELNLGRRE EYDVLDKRRG RDPEMGGKPR RKNPQEGLYN     60
ELQKDKMAEA YSEIGMKGER RRGKGHDGLY QGLSTATKDT YDALHMQALP PR            112

SEQ ID NO: 31              moltype = AA   length = 22
FEATURE                    Location/Qualifiers
REGION                     1..22
                           note = Synthetic
source                     1..22
                           mol_type = protein
                           organism = synthetic construct
SEQUENCE: 31
QNQLYNELNL GRREEYDVLD KR                                             22

SEQ ID NO: 32              moltype = DNA   length = 66
FEATURE                    Location/Qualifiers
misc_feature               1..66
                           note = Synthetic
source                     1..66
                           mol_type = other DNA
                           organism = synthetic construct
SEQUENCE: 32
```

-continued

```
cagaaccagc tctataacga gctcaatcta ggacgaagag aggagtacga tgttttggac    60
aagaga                                                               66

SEQ ID NO: 33          moltype = AA  length = 22
FEATURE                Location/Qualifiers
REGION                 1..22
                       note = Synthetic
source                 1..22
                       mol_type = protein
                       organism = synthetic construct
SEQUENCE: 33
QNQLFNELNL GRREEFDVLD KR                                             22

SEQ ID NO: 34          moltype = DNA  length = 66
FEATURE                Location/Qualifiers
misc_feature           1..66
                       note = Synthetic
source                 1..66
                       mol_type = other DNA
                       organism = synthetic construct
SEQUENCE: 34
cagaaccagc tctttaacga gctcaatcta ggacgaagag aggagttcga tgttttggac    60
aagaga                                                               66

SEQ ID NO: 35          moltype = AA  length = 23
FEATURE                Location/Qualifiers
REGION                 1..23
                       note = Synthetic
source                 1..23
                       mol_type = protein
                       organism = synthetic construct
SEQUENCE: 35
QEGLYNELQK DKMAEAYSEI GMK                                            23

SEQ ID NO: 36          moltype = DNA  length = 69
FEATURE                Location/Qualifiers
misc_feature           1..69
                       note = Synthetic
source                 1..69
                       mol_type = other DNA
                       organism = synthetic construct
SEQUENCE: 36
caggaaggcc tgtacaatga actgcagaaa gataagatgg cggaggccta cagtgagatt    60
gggatgaaa                                                            69

SEQ ID NO: 37          moltype = AA  length = 23
FEATURE                Location/Qualifiers
REGION                 1..23
                       note = Synthetic
source                 1..23
                       mol_type = protein
                       organism = synthetic construct
SEQUENCE: 37
QEGLFNELQK DKMAEAFSEI GMK                                            23

SEQ ID NO: 38          moltype = DNA  length = 69
FEATURE                Location/Qualifiers
misc_feature           1..69
                       note = Synthetic
source                 1..69
                       mol_type = other DNA
                       organism = synthetic construct
SEQUENCE: 38
caggaaggcc tgttcaatga actgcagaaa gataagatgg cggaggcctt cagtgagatt    60
gggatgaaa                                                            69

SEQ ID NO: 39          moltype = AA  length = 22
FEATURE                Location/Qualifiers
REGION                 1..22
                       note = Synthetic
source                 1..22
                       mol_type = protein
                       organism = synthetic construct
SEQUENCE: 39
HDGLYQGLST ATKDTYDALH MQ                                             22

SEQ ID NO: 40          moltype = DNA  length = 66
FEATURE                Location/Qualifiers
misc_feature           1..66
```

-continued

```
                          note = Synthetic
source                    1..66
                          mol_type = other DNA
                          organism = synthetic construct
SEQUENCE: 40
cacgatggcc tttaccaggg tctcagtaca gccaccaagg acacctacga cgcccttcac  60
atgcag                                                             66

SEQ ID NO: 41             moltype = AA  length = 22
FEATURE                   Location/Qualifiers
REGION                    1..22
                          note = Synthetic
source                    1..22
                          mol_type = protein
                          organism = synthetic construct
SEQUENCE: 41
HDGLFQGLST ATKDTFDALH MQ                                            22

SEQ ID NO: 42             moltype = DNA  length = 66
FEATURE                   Location/Qualifiers
misc_feature              1..66
                          note = Synthetic
source                    1..66
                          mol_type = other DNA
                          organism = synthetic construct
SEQUENCE: 42
cacgatggcc ttttccaggg gctcagtaca gccaccaagg acaccttcga cgcccttcac  60
atgcag                                                             66

SEQ ID NO: 43             moltype = AA  length = 112
FEATURE                   Location/Qualifiers
REGION                    1..112
                          note = Synthetic
source                    1..112
                          mol_type = protein
                          organism = synthetic construct
SEQUENCE: 43
RVKFSRSADA PAYQQGQNQL YNELNLGRRE EYDVLDKRRG RDPEMGGKPR RKNPQEGLFN  60
ELQKDKMAEA FSEIGMKGER RRGKGHDGLF QGLSTATKDT FDALHMQALP PR         112

SEQ ID NO: 44             moltype = DNA  length = 336
FEATURE                   Location/Qualifiers
misc_feature              1..336
                          note = Synthetic
source                    1..336
                          mol_type = other DNA
                          organism = synthetic construct
SEQUENCE: 44
agagtgaagt tcagcaggag cgcagacgcc cccgcgtacc agcagggcca gaaccagctc  60
tataacgagc tcaatctagg acgaagagag gagtacgatg ttttggacaa gagacgtggc 120
cgggaccctg agatgggggg aaagccgaga aggaagaacc ctcaggaagg cctgttcaat 180
gaactgcaga aagataagat ggcggaggcc ttcagtgaga ttgggatgaa aggcgagcgc 240
cggagggggca aggggcacga tggcctttc cagggggctca gtacagccac caaggacacc 300
ttcgacgccc ttcacatgca ggccctgccc cctcgc                          336

SEQ ID NO: 45             moltype = DNA  length = 336
FEATURE                   Location/Qualifiers
misc_feature              1..336
                          note = Synthetic
source                    1..336
                          mol_type = other DNA
                          organism = synthetic construct
SEQUENCE: 45
agagtgaagt tcagcaggag cgcagacgcc cccgcgtacc agcagggcca gaaccagctc  60
tataacgagc tcaatctagg acgaagagag gagtacgatg ttttggacaa gagacgtggc 120
cgggaccctg agatgggggg aaagccgaga aggaagaacc ctcaggaagg cctgttcaat 180
gaactgcaga aagataagat ggcggaggcc ttcagtgaga ttgggatgaa aggcgagcgc 240
cggagggggca aggggcacga tggcctttc cagggtctca gtacagccac caaggacacc 300
ttcgacgccc ttcacatgca ggccctgccc cctcgc                          336

SEQ ID NO: 46             moltype = DNA  length = 123
FEATURE                   Location/Qualifiers
misc_feature              1..123
                          note = Synthetic
source                    1..123
                          mol_type = other DNA
                          organism = synthetic construct
SEQUENCE: 46
aggagtaaga ggagcaggct cctgcacagt gactacatga acatgactcc ccgccgcccc  60
```

```
gggcccaccc gcaagcatta ccagccctat gccccaccac gcgacttcgc agcctatcgc   120
tcc                                                                  123

SEQ ID NO: 47          moltype = AA  length = 255
FEATURE                Location/Qualifiers
source                 1..255
                       mol_type = protein
                       organism = Homo sapiens
SEQUENCE: 47
MGNSCYNIVA TLLLVLNFER TRSLQDPCSN CPAGTFCDNN RNQICSPCPP NSFSSAGGQR   60
TCDICRQCKG VFRTRKECSS TSNAECDCTP GFHCLGAGCS MCEQDCKQGQ ELTKKGCKDC   120
CFGTFNDQKR GICRPWTNCS LDGKSVLVNG TKERDVVCGP SPADLSPGAS SVTPPAPARE   180
PGHSPQIISF FLALTSTALL FLLFFLTLRF SVVKRGRKKL LYIFKQPFMR PVQTTQEEDG   240
CSCRFPEEEE GGCEL                                                    255

SEQ ID NO: 48          moltype = AA  length = 488
FEATURE                Location/Qualifiers
REGION                 1..488
                       note = Synthetic
source                 1..488
                       mol_type = protein
                       organism = synthetic construct
SEQUENCE: 48
MDMRVPAQLL GLLLLWLPDT RCEIVLTQSP GTLSLSPGER ATLSCRASQS VSSSYLAWYQ   60
QKPGQAPRLL IYGASSRATG IPDRFSGSGS GTDFTLTISR LEPEDFAVYY CQQAGAVPIT   120
FGGGTKVEIK GGGGSGGGGS GGGGSQVQLV ESGGGVVQPG RSLRLSCAAS GFTFSSYGMH   180
WVRQAPGKGL EWVALIWYDG SNKYYADSVK GRFTISRDNS KNTLYLQMNS LRAEDTAVYY   240
CAKPVEGLLR GFDYWGQGTL VTVSSRAAAI EVMYPPPYLD NEKSNGTIIH VKGKHLCPSP   300
LFPGPSKPFW VLVVVGGVLA CYSLLVTVAF IIFWVRSKRS RLLHSDYMNM TPRRPGPTRK   360
HYQPYAPPRD FAAYRSRVKF SRSADAPAYQ QGQNQLYNEL NLGRREEYDV LDKRRGRDPE   420
MGGKPRRKNP QEGLFNELQK DKMAEAFSEI GMKGERRRGK GHDGLFQGLS TATKDTFDAL   480
HMQALPPR                                                            488

SEQ ID NO: 49          moltype = DNA  length = 1464
FEATURE                Location/Qualifiers
misc_feature           1..1464
                       note = Synthetic
source                 1..1464
                       mol_type = other DNA
                       organism = synthetic construct
SEQUENCE: 49
atggatatga gagtaccagc tcagctgctg ggcctgctgc ttttgtggtt gccggacaca   60
cgctgtgaga ttgtcctgac tcagtctccc gggactcgtg ccctcagccc cggtgaacgc   120
gctacccttt catgcagagc ctctcagtct gtgtccagca gctacctcgc atggtatcag   180
cagaagcccg gacaggctcc caggctgttg atctatggag ctagtagtcg agcaacaggc   240
atcccagatc gcttctcagg gagcggttca ggtacagact tcacgctgac gatttcaagg   300
ctggaacccg aagattttgc cgtctattat tgtcaacagg caggggctgt gccaatcact   360
ttcgggggcg ggaccaaggt ggaaatcaaa ggaggcggag gaagtggagg aggaggggagc   420
ggtggaggag ggtcacaggt gcagctggta gaatctggcg gaggggtcgt tcaaccaggg   480
aggtcattgc ggttgagctg cgcagcgagt ggttttacct tcagcagtta tggaatgcat   540
tgggtgagac aagcaccagg aaaaggtctg gagtgggtgg ctttgatttg gtacgacggc   600
agtaataaat actacgccga ttctgttaag ggcagattta ctatttctcg cgacaacagc   660
aagaacacgc tgtacctgca gatgaactct ctgagagccg aagatacagc agtgtactat   720
tgtgctaagc ccgtagaagg gctcctgagg ggattcgatt attgggggcca gggtacgctt   780
gtgacagtgt ctagtcgggc ggccgcaatt gaagttatgt atcctcctcc ttacctagac   840
aatgagaaga gcaatggaac cattatccat gtgaaaggga aacacctttg tccaagtccc   900
ctatttcccg gaccttctaa gcccttttgg gtgctggtgg tggttggtgg agtcctggct   960
tgctatagct tgctagtaac agtggccttt attattttct gggtgaggag taagaggagc   1020
aggctcctgc acagtgacta catgaacatg actcccccgcc gccccgggcc cacccgcaag   1080
cattaccagc cctatgcccc accacgcgac ttcgcagcct atcgctccag agtgaagttc   1140
agcaggagcg cagacgcccc cgcgtaccag cagggccaga accagctcta taacgagctc   1200
aatctaggac gaagagagga gtacgatgtt ttggacaaga cgtggccg ggaccctgag    1260
atggggggaa agccgagaag gaagaaccct caggaaggc tgttcaatga actgcagaaa   1320
gataagatgg cggaggcctt cagtgagatt gggatgaaag cgagcgccg gaggggcaag    1380
gggcacgatg gcccttttcca gggtctcagt acagccacca aggacaccctt cgacgcccctt   1440
cacatgcagg ccctgccccc tcgc                                          1464

SEQ ID NO: 50          moltype = AA  length = 488
FEATURE                Location/Qualifiers
REGION                 1..488
                       note = Synthetic
source                 1..488
                       mol_type = protein
                       organism = synthetic construct
SEQUENCE: 50
MDMRVPAQLL GLLLLWLPDT RCEIVLTQSP GTLSLSPGER ATLSCRASQS VRSSYLAWYQ   60
QKPGQAPRLL IYGASSRATG IPDRFSGSGS GTDFTLTISR LEPEDFAVYY CQQLFDSPYT   120
FGGGTKVEIK GGGGSGGGGS GGGGSQVQLV ESGGGVVQPG RSLRLSCAAS GFTFSSYGMH   180
WVRQAPGKGL EWVALIWYDG SNKYYADSVK GRFTISRDNS KNTLYLQMNS LRAEDTAVYY   240
```

-continued

```
CAKPVEGLLR GFDYWGQGTL VTVSSRAAAI EVMYPPPYLD NEKSNGTIIH VKGKHLCPSP  300
LFPGPSKPFW VLVVVGGVLA CYSLLVTVAF IIFWVRSKRS RLLHSDYMNM TPRRPGPTRK  360
HYQPYAPPRD FAAYRSRVKF SRSADAPAYQ QGQNQLYNEL NLGRREEYDV LDKRRGRDPE  420
MGGKPRRKNP QEGLFNELQK DKMAEAFSEI GMKGERRRGK GHDGLFQGLS TATKDTFDAL  480
HMQALPPR                                                            488

SEQ ID NO: 51              moltype = DNA   length = 1464
FEATURE                    Location/Qualifiers
misc_feature               1..1464
                           note = Synthetic
source                     1..1464
                           mol_type = other DNA
                           organism = synthetic construct
SEQUENCE: 51
atggatatga gagtaccagc tcagctgctg ggcctgctgc ttttgtggtt gccggacaca   60
cgctgtgaga ttgtgctgac acagtctcca ggcacactct cccttagccc gggcgagagg  120
gccactctga gctgtcgggc tagtcagtca gtaaggagct cttatctggc ctggtatcag  180
cagaaaccag ggcaggctcc aaggctgctt atctacggtg caagttcccg gccaacaggc  240
atcccagatc gctttagcgg tagcgggagt gggaccgatt tcactctgac catctcccgc  300
cttgagcccg aggatttcgc tgtctattat tgccagcaac tgtttgactc accctatacg  360
ttcggtggag ggaccaaagt ggagatcaag ggaggcggag gaagtggagg aggagggagc  420
ggtggaggag ggtcacaggt gcagctggta gaatctgggc gagggggtcg tcaaccaggg  480
aggtcattgc ggttgagctg cgcagcgagt ggttttacct tcagcagtta tggaatgcat  540
tgggtgagac aagcaccagg aaaaggtctg gagtgggtgg ctttgatttg gtacgacggc  600
agtaataaat actacgccga ttctgttaag ggcagattta ctatttctcg cgacaacagc  660
aagaacagca tgtacctgca gatgaactct ctgagagccg aagatacagc agtgtactat  720
tgtgctaagc ccgtagaagg gctcctgagg ggattcgatt attggggcca gggtacgctt  780
gtgacagtgt ctagtcgggc ggccgcaatt gaagttatgt atcctcctcc ttacctagac  840
aatgagaaga gcaatggaac cattatccat gtgaaaggga aacacctttg tccaagtccc  900
ctatttcccg gaccttctaa gcccttttgg gtgctggtgg tggttggtgg agtcctggct  960
tgctatagct tgctagtaac agtggccttt attattttct gggtgaggag taagaggagc 1020
aggctcctgc acagtgacta catgaacatg actccccgcc gccccgggcc cacccgcaag 1080
cattaccagc cctatgcccc accacgcgac ttcgcagcct atcgctccag agtgaagttc 1140
agcaggagcg cagacgcccc cgcgtaccag cagggccaga accagctcta taacgagctc 1200
aatctaggac gaagagagga gtacgatgtt ttggacaaga acgtggccg ggaccctgag 1260
atggggggaa agccgagaag gaagaaccct caggaaggcc tgttcaatga actgcagaaa 1320
gataagatgg cggaggcctt cagtgagatt gggatgaaag cgagcgccg gagggggcaag 1380
gggcacgatg gcctttttcca ggggctcagt acagccacca aggacacctt cgacgccctt 1440
cacatgcagg ccctgccccc tcgc                                        1464

SEQ ID NO: 52              moltype = AA   length = 485
FEATURE                    Location/Qualifiers
REGION                     1..485
                           note = Synthetic
source                     1..485
                           mol_type = protein
                           organism = synthetic construct
SEQUENCE: 52
MEFGLSWVFL VALLRGVQCQ VQLVESGGGV VQPGRSLRLS CAASGFTFSS YGMHWVRQAP   60
GKGLEWVALI WYDGSNKYYA DSVKGRFTIS RDNSKNTLYL QMNSLRAEDT AVYYCAKPVE  120
GLLRGFDYWG QGTLVTVSSG GGSGGGGSG GGGSEIVLTQ SPGTLSLSPG ERATLSCRAS  180
QSVSSSYLAW YQQKPGQAPR LLIYGASRRA TGIPDRFSGS GSGTDFTLTI SRLEPEDFAV  240
YYCQQAGIPP YTFGGGTKVE IKRAAAIEVM YPPPYLDNEK SNGTIIHVKG KHLCPSPLFP  300
GPSKPFWVLV VVGGVLACYS LLVTVAFIIF WVRSKRSRLL HSDYMNMTPR RPGPTRKHYQ  360
PYAPPRDFAA YRSRVKFSRS ADAPAYQQGQ NQLYNELNLG RREEYDVLDK RRGRDPEMGG  420
KPRRKNPQEG LFNELQKDKM AEAFSEIGMK GERRRGKGHD GLFQGLSTAT KDTFDALHMQ  480
ALPPR                                                               485

SEQ ID NO: 53              moltype = DNA   length = 1455
FEATURE                    Location/Qualifiers
misc_feature               1..1455
                           note = Synthetic
source                     1..1455
                           mol_type = other DNA
                           organism = synthetic construct
SEQUENCE: 53
atggaattcg gcttgtcatg ggtgttcctc gtcgcgctgc tgcgcggcgt tcagtgccag   60
gtgcagctgg tagaatctgg cggagggggtc gttcaaccag gaggtcatt gcggttgagc  120
tgcgcagcga gtggttttac cttcagcagt tatggaatgc actgggtgag acaagcacca  180
ggaaaaggtc tggagtgggt ggctttgatt tggtacgacg gcagtaataa atactacgcc  240
gattctgtta agggcagatt tactatttct cgcgacaaca gcaagaacac gctgtacctg  300
cagatgaact ctctgagagc cgaagataca gcagtgtact attgtgctaa gcccgtagaa  360
gggctcctga ggggattcga ttattggggc cagggtacgc ttgtgacagt gtctagtgga  420
ggcggaggaa gtggaggagg aggagcggt gaggaggtct gctcacccag  480
tccccgggaa cactgagtct ctctccaggg gaaagagcaa cattgtcctg cagagcatcc  540
cagagcgtga gctccagcta cctgcctgg tatcagcaga aaccaggcca ggcaccccgc  600
ctgcttatct acggtgcatc caggagagcc actgggatcc ccgatcgatt ctctggatca  660
gggtctggca ctgactttac attgacgatc tcacggctgg aacccgagga tttcgccgtg  720
tattactgcc aacaggccgg aattccaccg tatacctcg gaggaggtac taaagtagag  780
```

```
attaaacggg cggccgcaat tgaagttatg tatcctcctc cttacctaga caatgagaag  840
agcaatggaa ccattatcca tgtgaaaggg aaacacctt gtccaagtcc cctatttccc  900
ggaccttcta agccctttg ggtgctggtg gtggttggtg gagtcctggc ttgctatagc  960
ttgctagtaa cagtggcctt tattattttc tgggtgagga gtaagaggag caggctcctg  1020
cacagtgact acatgaacat gactccccgc cgcccgggc ccacccgcaa gcattaccag  1080
ccctatgccc caccacgcga cttcgcagcc tatcgctcca gagtgaagtt cagcaggagc  1140
gcagacgccc ccgcgtacca gcagggccag aaccagctct ataacgagct caatctagga  1200
cgaagagagg agtacgatgt tttggacaag agacgtggcc gggaccctga gatggggga  1260
aagccgagaa ggaagaaccc tcaggaaggc ctgttcaatg aactgcagaa agataagatg  1320
gcggaggcct tcagtgagat tgggatgaaa ggcgagcgcc gaggggcaa ggggcacgat  1380
ggccttttcc aggggctcag tacagccacc aaggacacct tcgacgccct tcacatgcag  1440
gccctgcccc ctcgc                                                  1455

SEQ ID NO: 54           moltype = AA  length = 22
FEATURE                 Location/Qualifiers
REGION                  1..22
                        note = Synthetic
source                  1..22
                        mol_type = protein
                        organism = synthetic construct
SEQUENCE: 54
MDMRVPAQLL GLLLLWLPDT RC                                            22

SEQ ID NO: 55           moltype = AA  length = 19
FEATURE                 Location/Qualifiers
REGION                  1..19
                        note = Synthetic
source                  1..19
                        mol_type = protein
                        organism = synthetic construct
SEQUENCE: 55
MEFGLSWVFL VALLRGVQC                                                19

SEQ ID NO: 56           moltype = DNA  length = 120
FEATURE                 Location/Qualifiers
misc_feature            1..120
                        note = Synthetic
source                  1..120
                        mol_type = other DNA
                        organism = synthetic construct
SEQUENCE: 56
attgaagtta tgtatcctcc tccttaccta gacaatgaga agagcaatgg aaccattatc  60
catgtgaaag ggaaacacct ttgtccaagt ccctatttc ccggaccttc taagcccttt  120

SEQ ID NO: 57           moltype = AA  length = 10
FEATURE                 Location/Qualifiers
REGION                  1..10
                        note = Synthetic
source                  1..10
                        mol_type = protein
                        organism = synthetic construct
SEQUENCE: 57
QQVDSLHPFT                                                          10

SEQ ID NO: 58           moltype = AA  length = 109
FEATURE                 Location/Qualifiers
REGION                  1..109
                        note = Synthetic
source                  1..109
                        mol_type = protein
                        organism = synthetic construct
SEQUENCE: 58
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QVDSLHPFTF GGGTKVEIK              109

SEQ ID NO: 59           moltype = AA  length = 10
FEATURE                 Location/Qualifiers
REGION                  1..10
                        note = Synthetic
source                  1..10
                        mol_type = protein
                        organism = synthetic construct
SEQUENCE: 59
QQAGGVPPLT                                                          10

SEQ ID NO: 60           moltype = AA  length = 109
FEATURE                 Location/Qualifiers
REGION                  1..109
                        note = Synthetic
```

```
source                  1..109
                        mol_type = protein
                        organism = synthetic construct
SEQUENCE: 60
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QAGGVPPLTF GGGTKVEIK                109

SEQ ID NO: 61           moltype = AA  length = 9
FEATURE                 Location/Qualifiers
REGION                  1..9
                        note = Synthetic
source                  1..9
                        mol_type = protein
                        organism = synthetic construct
SEQUENCE: 61
QQAGVPPLT                                                             9

SEQ ID NO: 62           moltype = AA  length = 108
FEATURE                 Location/Qualifiers
REGION                  1..108
                        note = Synthetic
source                  1..108
                        mol_type = protein
                        organism = synthetic construct
SEQUENCE: 62
EIVLTQSPGT LSLSPGERAT LSCRASQSVR SSYLAWYQQK PGQAPRLLIY GASSRATGIP    60
DRFSGSGSGT DFTLTISRLE PEDFAVYYCQ QAGVPPLTFG GGTKVEIK                 108

SEQ ID NO: 63           moltype = AA  length = 10
FEATURE                 Location/Qualifiers
REGION                  1..10
                        note = Synthetic
source                  1..10
                        mol_type = protein
                        organism = synthetic construct
SEQUENCE: 63
QQAGGVPPFT                                                           10

SEQ ID NO: 64           moltype = AA  length = 109
FEATURE                 Location/Qualifiers
REGION                  1..109
                        note = Synthetic
source                  1..109
                        mol_type = protein
                        organism = synthetic construct
SEQUENCE: 64
EIVMTQSPGT LSLSPGERAT LSCRASQSVS SSYLAWYQQK PGQAPRLLIY GASSRATGIP    60
DRFSGSGSGT DFTLTISRLE PEDFAVYYCQ QAGGVPPFTF GGGTKVEIK                109

SEQ ID NO: 65           moltype = AA  length = 7
FEATURE                 Location/Qualifiers
REGION                  1..7
                        note = Synthetic
source                  1..7
                        mol_type = protein
                        organism = synthetic construct
SEQUENCE: 65
GASNRAT                                                              7

SEQ ID NO: 66           moltype = AA  length = 9
FEATURE                 Location/Qualifiers
REGION                  1..9
                        note = Synthetic
source                  1..9
                        mol_type = protein
                        organism = synthetic construct
SEQUENCE: 66
QQAGVFPFT                                                            9

SEQ ID NO: 67           moltype = AA  length = 108
FEATURE                 Location/Qualifiers
REGION                  1..108
                        note = Synthetic
source                  1..108
                        mol_type = protein
                        organism = synthetic construct
SEQUENCE: 67
EIVMTQSPGT LSLSPGERAT LSCRASQSVS SSYLAWYQQK PGQAPRLLIY GASNRATGIP    60
DRFSGSGSGT DFTLTISRLE PEDFAVYYCQ QAGVFPFTFG GGTKVEIK                 108
```

-continued

```
SEQ ID NO: 68              moltype = DNA   length = 360
FEATURE                    Location/Qualifiers
misc_feature               1..360
                           note = Synthetic
source                     1..360
                           mol_type = other DNA
                           organism = synthetic construct
SEQUENCE: 68
caggtgcagc tggtggagtc tggggggaggc gtggtccagc ctgggaggtc cctgagactc     60
tcctgtgcag cgtctggatt caccttcagt agctatggca tgcactgggt ccgccaggct    120
ccaggcaagg ggctggagtg ggtggcactg atatggtatg atggaagtaa taaatactat    180
gcagactccg tgaagggccg attcaccatc tccagagaca attccaagaa cacgctgtat    240
ctgcaaatga acagcctgag agccgaggac acggcggtgt actactgcgc caagccagtg    300
gaaggactat taagaggatt cgattactgg ggacagggta cattggtcac cgtctcctca    360

SEQ ID NO: 69              moltype = DNA   length = 324
FEATURE                    Location/Qualifiers
misc_feature               1..324
                           note = Synthetic
source                     1..324
                           mol_type = other DNA
                           organism = synthetic construct
SEQUENCE: 69
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caggccggag ccgtccctat cacttttggc    300
ggagggacca aggttgagat caaa                                           324

SEQ ID NO: 70              moltype = DNA   length = 324
FEATURE                    Location/Qualifiers
misc_feature               1..324
                           note = Synthetic
source                     1..324
                           mol_type = other DNA
                           organism = synthetic construct
SEQUENCE: 70
gaaattgtgt tgacgcagtc tccaggcacc ctgtctttgt ctccagggga aagagccacc     60
ctctcctgca gggccagtca gagtgttagg agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagctcttcg acagtcctta cacttttggc    300
ggagggacca aggttgagat caaa                                           324

SEQ ID NO: 71              moltype = DNA   length = 324
FEATURE                    Location/Qualifiers
misc_feature               1..324
                           note = Synthetic
source                     1..324
                           mol_type = other DNA
                           organism = synthetic construct
SEQUENCE: 71
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gaaggccac tggcatccca     180
gacaggttca gtggcagtgg gtctgggaca gacttcactc tcaccatcag cagactggag    240
cctgaagatt ttgcagtgta ttactgtcag caggccggca tccccccctta cacttttggc    300
ggagggacca aggttgagat caaa                                           324

SEQ ID NO: 72              moltype = DNA   length = 327
FEATURE                    Location/Qualifiers
misc_feature               1..327
                           note = Synthetic
source                     1..327
                           mol_type = other DNA
                           organism = synthetic construct
SEQUENCE: 72
gaaattgtgt tgacgcagtc tccaggcacc ctgtctttgt ctccagggga aagagccacc     60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag caggtcgaca gtctccatcc tttcactttt    300
ggcggaggga ccaaggttga gatcaaa                                        327

SEQ ID NO: 73              moltype = DNA   length = 327
FEATURE                    Location/Qualifiers
misc_feature               1..327
```

-continued

```
                      note = Synthetic
source                1..327
                      mol_type = other DNA
                      organism = synthetic construct
SEQUENCE: 73
gaaattgtgt tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag caggccggag gcgtccctcc tctcactttt  300
ggcggaggga ccaaggttga gatcaaa                                      327

SEQ ID NO: 74            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 74
gaaattgtgt tgacgcagtc tccaggcacc ctgtctttgt ctccagggga aagagccacc   60
ctctcctgca gggccagtca gagtgttagg agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag caggccggag tccccctct cactttggc  300
ggagggacca aggttgagat caaa                                        324

SEQ ID NO: 75            moltype = DNA  length = 327
FEATURE                  Location/Qualifiers
misc_feature             1..327
                         note = Synthetic
source                   1..327
                         mol_type = other DNA
                         organism = synthetic construct
SEQUENCE: 75
gaaattgtga tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag caggccggag gcgtccctcc tttcactttt  300
ggcggaggga ccaaggttga gatcaaa                                      327

SEQ ID NO: 76            moltype = DNA  length = 324
FEATURE                  Location/Qualifiers
misc_feature             1..324
                         note = Synthetic
source                   1..324
                         mol_type = other DNA
                         organism = synthetic construct
SEQUENCE: 76
gaaattgtga tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca acagggccac tggcatccca  180
gacaggttca gtggcagtgg gtctgggaca gacttcactc tcaccatcag cagactggag  240
cctgaagatt ttgcagtgta ttactgtcag caggccggag tcttcccttt cactttggc  300
ggagggacca aggttgagat caaa                                        324

SEQ ID NO: 77            moltype = AA  length = 920
FEATURE                  Location/Qualifiers
REGION                   1..920
                         note = Synthetic
source                   1..920
                         mol_type = protein
                         organism = synthetic construct
SEQUENCE: 77
MPPPRLLFFL LFLTPMEVRP EEPLVVKVEE GDNAVLQCLK GTSDGPTQQL TWSRESPLKP   60
FLKLSLGLPG LGIHMRPLAI WLFIFNVSQQ MGGFYLCQPG PPSEKAWQPG WTVNVEGSGE  120
LFRWNVSDLG GLGCGLKNRS SEGPSSPSGK LMSPKLYVWA KDRPEIWEGE PPCLPPRDSL  180
NQSLSQDLTM APGSTLWLSC GVPPDSVSRG PLSWTHVHPK GPKSLLSLEL KDDRPARDMW  240
VMETGLLLPR ATAQDAGKYY CHRGNLTMSF HLEITARPVL WHWLLRTGGW KHHHHHHHH   300
HDYDIPTTEN LYFQGGGGGS GGGGSGGGGS GGGGSDAHKS EVAHRFKDLG EENFKALVLI  360
AFAQYLQQCP FEDHVKLVNE VTEFAKTCVA DESAENCDKS LHTLFGDKLC TVATLRETYG  420
EMADCCAKQE PERNECFLQH KDDNPNLPRL VRPEVDVMCT AFHDNEETFL KKYLYEIARR  480
HPYFYAPELL FFAKRYKAAF TECCQAADKA ACLLPKLDEL RDEGKASSAK QRLKCASLQK  540
FGERAFKAWA VARLSQRFPK AEFAEVSKLV TDLTKVHTEC CHGDLLECAD DRADLAKYIC  600
ENQDSISSKL KECCEKPLLE KSHCIAEVEN DEMPADLPSL AADFVESKDV CKNYAEAKDV  660
FLGMFLYEYA RRHPDYSVVL LLRLAKTYET TLEKCCAAAD PHECYAKVFD EFKPLVEEPQ  720
NLIKQNCELF EQLGEYKFQN ALLVRYTKKV PQVSTPTLVE VSRNLGKVGS KCCKHPEAKR  780
MPCAEDYLSV VLNQLCVLHE KTPVSDRVTK CCTESLVNRR PCFSALEVDE TYVPKEFNAE  840
```

TFTFHADICT LSEKERQIKK QTALVELVKH KPKATKEQLK AVMDDFAAFV EKCCKADDKE   900
TCFAEEGKKL VAASQAALGL                                              920